US012734181B2

(12) United States Patent
Tardi et al.

(10) Patent No.: US 12,734,181 B2
(45) Date of Patent: Sep. 15, 2026

(54) METHODS FOR PREPARING LIPOSOMAL FORMULATIONS

(71) Applicant: Jazz Pharmaceuticals Therapeutics, Inc., Palo Alto, CA (US)

(72) Inventors: Paul Tardi, Surrey (CA); Leon Wan, Vancouver (CA); Shyam Madhusudan Garg, Richmond (CA); Jun Gao, Coquitlam (CA); Philippe Legros, Burnaby (CA)

(73) Assignee: Jazz Pharmaceuticals Therapeutics, Inc., Palo Alto, CA (US)

( * ) Notice: Subject to any disclaimer, the term of this patent is extended or adjusted under 35 U.S.C. 154(b) by 288 days.

(21) Appl. No.: 18/579,824

(22) PCT Filed: Jul. 15, 2022

(86) PCT No.: PCT/US2022/037374

§ 371 (c)(1),
(2) Date: Jan. 16, 2024

(87) PCT Pub. No.: WO2023/288103

PCT Pub. Date: Jan. 19, 2023

(65) Prior Publication Data

US 2024/0350411 A1 Oct. 24, 2024

Related U.S. Application Data

(60) Provisional application No. 63/222,887, filed on Jul. 16, 2021.

(51) Int. Cl.

| | |
|---|---|
| ***A61K 31/635*** | (2006.01) |
| ***A61K 9/127*** | (2006.01) |
| ***A61K 9/1271*** | (2025.01) |
| ***A61K 9/1272*** | (2025.01) |
| ***A61K 9/1277*** | (2025.01) |
| ***A61K 45/06*** | (2006.01) |
| ***A61K 47/18*** | (2017.01) |
| ***A61K 47/20*** | (2006.01) |
| ***A61K 47/26*** | (2006.01) |
| ***A61K 47/28*** | (2006.01) |
| ***A61P 7/04*** | (2006.01) |

(52) U.S. Cl.

CPC ............ *A61K 31/635* (2013.01); *A61K 9/127* (2013.01); *A61K 9/1271* (2013.01); *A61K 9/1272* (2013.01); *A61K 9/1277* (2013.01); *A61K 45/06* (2013.01); *A61K 47/186* (2013.01); *A61K 47/20* (2013.01); *A61K 47/26* (2013.01); *A61K 47/28* (2013.01); *A61P 7/04* (2018.01)

(58) Field of Classification Search

None

See application file for complete search history.

(56) References Cited

U.S. PATENT DOCUMENTS

| | | | |
|---|---|---|---|
| 3,993,754 | A | 11/1976 | Rahman et al. |
| 4,145,410 | A | 3/1979 | Sears |
| 4,224,179 | A | 9/1980 | Schneider |
| 4,235,871 | A | 11/1980 | Papahadjopoulos et al. |
| 4,522,803 | A | 6/1985 | Lenk et al. |
| 4,588,578 | A | 5/1986 | Fountain et al. |
| 5,616,341 | A | 4/1997 | Mayer et al. |
| 5,736,155 | A | 4/1998 | Bally et al. |
| 5,785,987 | A | 7/1998 | Hope et al. |
| 5,837,282 | A | 11/1998 | Fenske et al. |
| 9,737,485 | B2 | 8/2017 | Hayes et al. |
| 10,507,182 | B2 | 12/2019 | Hayes et al. |
| 10,722,467 | B2 | 7/2020 | Hayes et al. |
| 2009/0028931 | A1 | 1/2009 | Wasan et al. |
| 2015/0272980 | A1 | 10/2015 | Rodrigueza et al. |
| 2015/0328232 | A1 | 11/2015 | Malinin et al. |
| 2017/0056421 | A1 | 3/2017 | Zhou et al. |
| 2018/0028495 | A1 | 2/2018 | Lannutti et al. |

FOREIGN PATENT DOCUMENTS

| | | | |
|---|---|---|---|
| TW | 201804987 | A | 2/2018 |
| WO | WO 1990/014105 | A1 | 11/1990 |
| WO | WO 2014/121211 | A2 | 8/2014 |
| WO | WO 2017/123616 | A1 | 7/2017 |

OTHER PUBLICATIONS

Danial, N. et al., "Cell Death: Critical Control Points," Cell, Jan. 23, 2004, 116:205-219.

International Search Report and Written Opinion received for International Application No. PCT/US22/37371, mailed Oct. 19, 2022.

Bangham, A. et al., "Diffusion of Univalent Ions across the Lamellae of Swollen Phospholipids," J. Mol. Biol., 1965, 13:238-252.

Berge, S. et al., "Pharmaceutical Salts," Journal of Pharmaceutical Sciences, Jan. 1977, 66(1):1-19.

Cullis, P. et al., "influence of pH gradients on the transbilayer transport of drugs, lipids, peptides and metal ions into large unilamellar vesicles," Biochimica et Biophysica Acta, 1997, 1331:187-211.

Deamer, D. et al., "Large Volume Liposomes by an Ether Vaporization Method," Biochimica et Biophysica Acta, 1976, 443:629-634.

Jin, L. et al., "Preparation, Purification, and Use of Fatty Acid-containing Liposomes," Journal of Visualized Experiments, Feb. 9, 2018, 132(e57324), pp. 1-7.

Liu, X. et al., "Irinotecan Delivery by Lipid-Coated Mesoporous Silica Nanoparticles Shows Improved Efficacy and Safety over Liposomes for Pancreatic Cancer," ACS Nano, Feb. 23, 2016, 10(2):2702-2715.

Pauli, G. et al., "Development and characterization of the Solvent-Assisted Active Loading Technology (SALT) for Liposomal Loading of Poorly Water-Soluble Compounds," Pharmaceutics, 2019, 11(465):1-12.

(Continued)

*Primary Examiner* — Nannette Holloman

(74) *Attorney, Agent, or Firm* — Morgan, Lewis & Bockius LLP

(57) ABSTRACT

Provided herein are methods of purifying liposomal formulations by washing with acidic aqueous solutions.

22 Claims, 4 Drawing Sheets

(56) References Cited

OTHER PUBLICATIONS

Szoka, Jr., F. et al., "Procedure for preparation of liposomes with large internal aqueous space and high capture by reverse-phase evaporation," Proc. Natl. Acad. Sci. USA, Sep. 1978, 75(9):4194-4198.

Zucker, D. et al., "Liposome drugs' loading efficiency: A working model based on loading conditions and drug's physicochemical properties," Journal of Controlled Release, 2009, 139:73-80.

METHODS FOR PREPARING LIPOSOMAL FORMULATIONS

CROSS REFERENCE TO RELATED APPLICATIONS

This application claims the priority benefit of U.S. Provisional Patent Application No. 63/222,887, filed Jul. 16, 2021, the disclosure of which is hereby incorporated herein by reference in its entirety.

FIELD

Provided herein are methods for preparing liposomal formulations comprising encapsulated hydrophobic drugs, which may be useful formulations for treating diseases such as hyperproliferative disorders.

BACKGROUND

Liposomes are closed vesicles having at least one lipid bilayer surrounding an aqueous core. The intra-liposomal space and lipid layer(s) can entrap a wide variety of substances including drugs, cosmetics, diagnostic reagents, genetic material and bioactive compounds. Since non-toxic lipids act as the basis for liposomes, they generally exhibit low toxicity. The low toxicity coupled with the ability of liposomes to increase the plasma circulation lifetime of agents gives rise to liposomes as vehicles particularly useful for delivering pharmaceutically active agents. In many cases, liposome-delivered drugs result in superior clinical efficacy paired with reduced toxicity.

Passive loading of lipophilic and to a lesser extent amphiphilic functional compounds is somewhat more efficient than hydrophilic functional compounds because they partition in both the lipid bilayer and the intraliposomal (internal) aqueous medium. However, using passive loading, the final functional-compound-to-lipid ratio as well as the encapsulation efficiency are generally low. The concentration of drug in the liposome equals that of the surrounding fluid and drug not entrapped in the internal aqueous medium is washed away after encapsulation. Moreover, drugs loaded into the bilayer are released from the liposome very rapidly when the liposome is injected into a subject. For sustained release of the drug in a patient it is preferable that the drug is encapsulated within the interior of the liposome.

Certain hydrophilic or amphiphilic compounds can be loaded into preformed liposomes using transmembrane pH- or ion-gradients (D. Zucker et al., Journal of Controlled Release (2009) 139:73-80). This technique is called active or remote loading. Compounds amenable to active loading should be able to change from an uncharged form, which can diffuse across the liposomal membrane, to a charged form that is not capable thereof. Typically, the functional compound is loaded by adding it to a suspension of liposomes prepared to have a lower inside/higher outside pH- or ion-gradient. Via active loading, a high functional-compound-to-lipid mass ratio and a high loading efficiency (up to 100%) can be achieved. Examples are active loading of anticancer drugs doxorubicin, daunorubicin, and vincristine (P. R. Cullis et al., Biochimica et Biophysica Acta, (1997) 1331:187-211, and references therein).

Hydrophobic drugs are mainly considered capable of loading into liposomes through membrane intercalation via passive loading/assembly mechanism. Wasan et al. states "Agents that have hydrophobic attributes can intercalate into the lipid bilayer and this can be achieved by adding the agent to the preformed liposomes." in a description of the use of micelles to transfer sparingly soluble agents to a liposome bilayer (US 2009/0028931). However, such loading relies on the hydrophobic drug being associated with or trapped in the lipid bilayer and the drug may easily leak out of the liposome, resulting in poor retention in vivo and less than desirable pharmacokinetics. In particular, when a drug is associated with or trapped in the lipid bilayer, rather than encapsulated in the aqueous core of the liposome, rapid release into the bloodstream may occur upon administration of the liposomes to a patient. This can be especially problematic with certain drugs for which dose-limiting toxicity and/or a low therapeutic index is a clinical concern, as is the case with many antineoplastic agents. For these reasons, among others, there is a need in the field of liposomal drug delivery for improved methods of preparing liposome-encapsulated drugs that do not have drugs associated with the lipid bilayer. Such improved liposomal formulations may offer advantageous pharmacokinetic properties and greater clinical value.

SUMMARY

The present disclosure relates to methods of preparing purified liposomal compositions.

In one aspect, provided is a method of preparing a purified liposomal composition comprising:

liposomes comprising:

(a) a lipid bilayer;

(b) an internal medium; and (c) a therapeutic agent encapsulated in the internal medium of the liposomes, wherein the therapeutic agent has low water solubility and can be protonated to a protonated form;

said method comprising:

(i) providing a crude liposomal composition; and (ii) purifying the crude liposomal composition with an acidified aqueous solution.

In some embodiments, the lipid bilayer comprises a first lipid and a first sterol; and the internal medium comprises a first loading aid.

In some embodiments, the first lipid is a polymer-conjugated lipid. For example, in some embodiments, the first lipid is selected from the group consisting of 1,2-distearoyl-rac-glycero-3-methoxypoly(ethylene glycol) (such as DSG-PEG2000), 1,2-dimyristoyl-rac-glycero-3-methoxypoly (ethylene glycol) (such as DMG-PEG2000), 1,2-dipalmitoyl-rac-glycero-3-methoxypoly(ethylene glycol) (such as DPG-PEG2000), and 1,2-distearoyl-sn-glycero-3-phosphoethanolamine-poly(ethylene glycol) (such as DSPE-PEG2000). In some embodiments, the first lipid is DSG-PEG2000.

In some embodiments, the lipid bilayer further comprises a second lipid. In some embodiments, the second lipid is a phospholipid. In some embodiments, the second lipid is distearoyl phosphatidyl choline (DSPC). In some embodiments, the second lipid is hydrogenated sphingomyelin.

In some embodiments, the internal medium is an aqueous internal medium. In some embodiments, the aqueous internal medium is an acidic aqueous internal medium. In some embodiments, the internal medium further comprises an additional solvent. In some embodiments, the additional solvent is an organic solvent. In some embodiments, the additional solvent is dimethylsulfoxide (DMSO).

In some embodiments, the first loading aid is an ionic loading aid. In some embodiments, the first loading aid is selected from the group consisting of ammonium sulfate (AS), ammonium sucrose octasulfate (NH4SOS), potassium sucrose octasulfate (KSOS), triethanolammonium sucrose octasulfate (TEA(OH)SOS), triethylammonium sucrose octasulfate (TEASOS), and sodium citrate. In some embodiments, the first loading aid is ammonium sulfate (AS). In some embodiments, the first loading aid is triethylammonium sucrose octasulfate (TEASOS).

In some embodiments, the internal medium further comprises a second loading aid. In some embodiments, the second loading aid is an ionic loading aid. In some embodiments, the second loading aid is selected from the group consisting of ammonium sulfate (AS), ammonium sucrose octasulfate (NH4SOS), potassium sucrose octasulfate (KSOS), triethylammonium sucrose octasulfate (TEASOS), and sodium citrate.

In some embodiments, the first loading aid is potassium sucrose octasulfate (KSOS) and the second loading aid is sodium citrate.

In some embodiments, the first sterol is cholesterol or beta-sitosterol.

In some embodiments, the therapeutic agent has a c Log P of greater than about 2. In some embodiments, the protonated form of the therapeutic agent has a pKa of greater than about 2.

In some embodiments, the therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, an HSP90 inhibitor, a JAK inhibitor, an ATR inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor. In some embodiments, the therapeutic agent is a Bcl inhibitor selected from the group consisting of a Bcl-2 inhibitor, a Bcl-$X_L$ inhibitor, and a Bcl-2/Bcl-$X_L$ dual inhibitor.

In some embodiments, the liposomes further comprise an additional therapeutic agent. In some embodiments, the additional therapeutic agent is encapsulated in the liposome. In some embodiments, the additional therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, an HSP90 inhibitor, a JAK inhibitor, an ATR inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor.

In some embodiments, the liposomes have a mean diameter between about 50 nm and about 250 nm.

In some embodiments, the acidified aqueous solution comprises a sugar. In some embodiments, the acidified aqueous solution comprises dextrose. In some embodiments, the acidified aqueous solution comprises sucrose. In some embodiments, the concentration of sugar in the acidified aqueous solution is between about 5 wt % and 20 wt %. In some embodiments, the concentration of acid in the acidified aqueous solution is between about 1 mM and 100 mM. In some embodiments, the acidified aqueous solution comprises methanesulfonic acid.

DETAILED DESCRIPTION

Figure 1A:
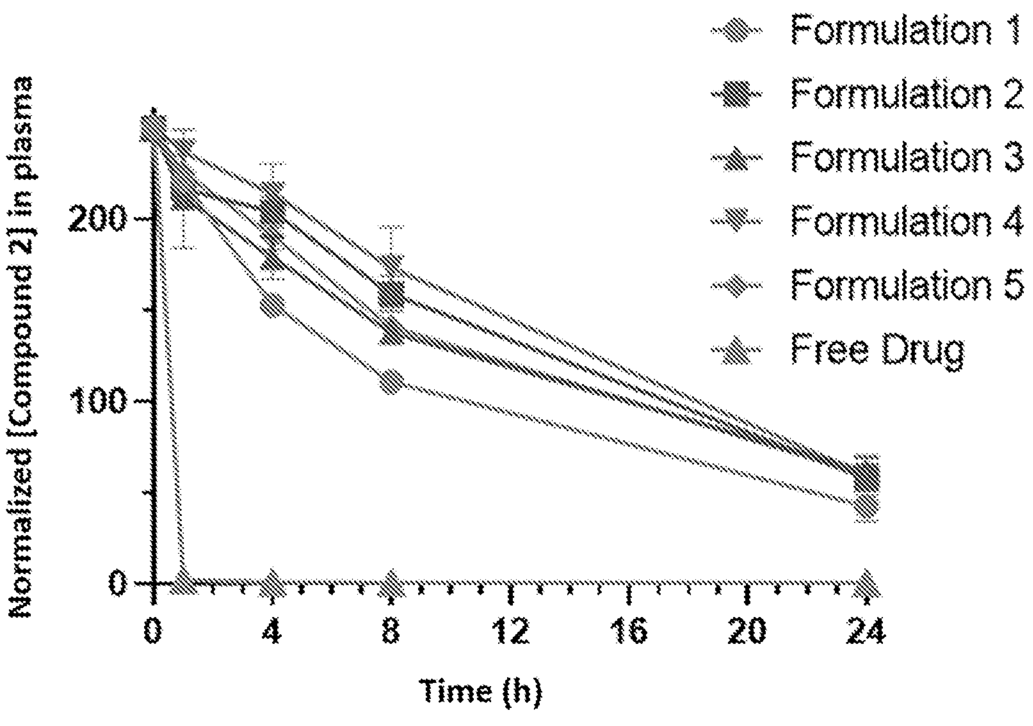
FIG. 1A shows the evolution of normalized plasma concentration of Compound 2 over time using various liposomal formulations compared to using the free drug.

Unless defined otherwise, all terms of art, notations and other scientific terms or terminology used herein have the same meaning as is commonly understood by one of ordinary skill in the art to which the present disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

Definitions

For use herein, unless clearly indicated otherwise, use of the terms “a”, “an” and the like refers to one or more.

Reference to “about” a value or parameter herein includes (and describes) embodiments that are directed to that value or parameter per se. For example, description referring to "about X" includes description of "X".

The term "therapeutic agent" or "drug" as used herein refers to chemical moieties used in a variety of therapeutic, including pharmaceutical applications.

The term "pharmaceutically acceptable salt" refers to a salt of any of the compounds herein which are known to be non-toxic and are commonly used in the pharmaceutical literature. In some embodiments, the pharmaceutically acceptable salt of a compound retains the biological effectiveness of the compounds described herein and are not biologically or otherwise undesirable. Examples of pharmaceutically acceptable salts can be found in Berge et al., Pharmaceutical Salts, *J. Pharmaceutical Sciences*, January 1977, 66(1), 1-19. Pharmaceutically acceptable acid addition salts can be formed with inorganic acids and organic acids. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, pyruvic acid, lactic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, 2-hydroxyethylsulfonic acid, p-toluenesulfonic acid, stearic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum. Organic bases from which salts can be derived include, for example, primary, secondary, and tertiary amines; substituted amines including naturally occurring substituted amines; cyclic amines; and basic ion exchange resins. Examples of organic bases include isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

As used herein, the term "subject" refers to an animal, such as a mammal, bird, or fish. In some embodiments, the subject is a mammal. Mammals include, for example, mice, rats, dogs, cats, pigs, sheep, horses, cows, and humans. In some embodiments, the subject is a human, for example a human that has been or will be the object of treatment, observation or experiment.

The term "therapeutically effective amount" or "effective amount" refers to that amount of a compound disclosed and/or described herein that is sufficient to affect treatment, as defined herein, when administered to a subject in need of such treatment. The therapeutically effective amount will vary depending upon, for example, the subject and disease condition being treated, the weight and age of the subject, the severity of the disease condition, the particular compound, the dosing regimen to be followed, timing of administration, the manner of administration, all of which can readily be determined by one of ordinary skill in the art. The therapeutically effective amount may be ascertained experimentally, for example by assaying blood concentration of the chemical entity, or theoretically, by calculating bioavailability.

"Treatment" (and related terms, such as "treat", "treated", "treating") includes one or more of: preventing a disease or disorder (i.e., causing the clinical symptoms of the disease or disorder not to develop); inhibiting a disease or disorder; slowing or arresting the development of clinical symptoms of a disease or disorder; and/or relieving a disease or disorder (i.e., causing relief from or regression of clinical symptoms). The term encompasses situations where the disease or disorder is already being experienced by a subject, as well as situations where the disease or disorder is not currently being experienced but is expected to arise. The term covers both complete and partial reduction or prevention of the condition or disorder, and complete or partial reduction of clinical symptoms of a disease or disorder. Thus, compounds described and/or disclosed herein may prevent an existing disease or disorder from worsening, assist in the management of the disease or disorder, or reduce or eliminate the disease or disorder. When used in a prophylactic manner, the compounds disclosed and/or described herein may prevent a disease or disorder from developing or lessen the extent of a disease or disorder that may develop.

Figure 3:
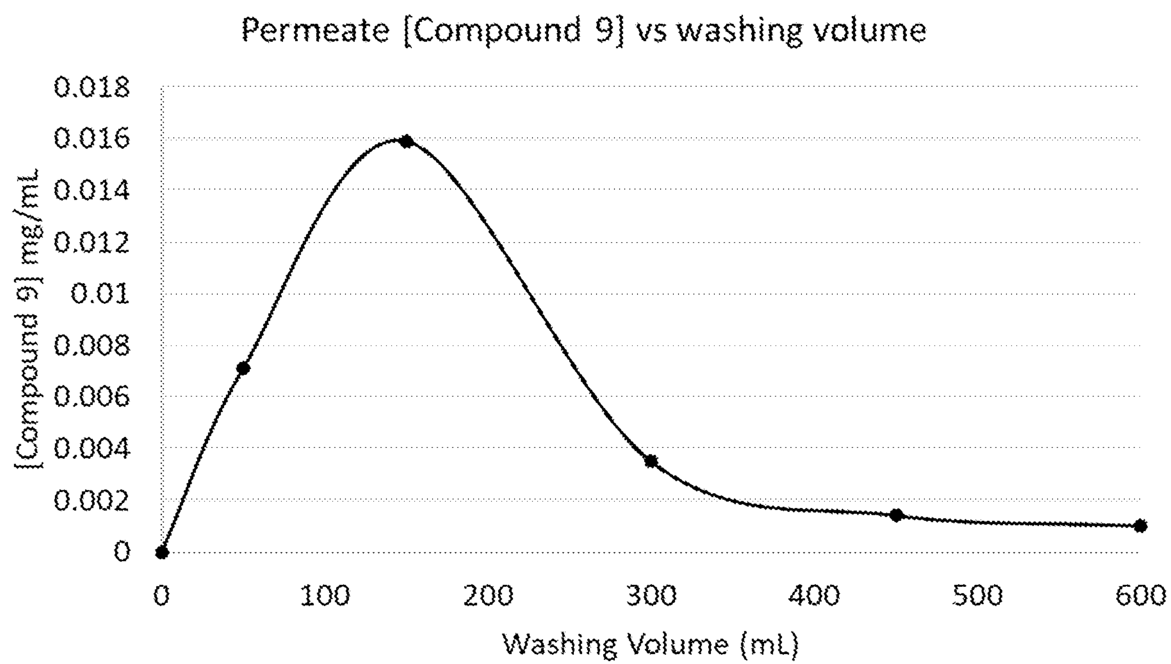
FIG. 3 depicts the permeate concentration of Compound 9 as a function of the washing volume during the purification of an exemplary liposomal formulation of the present disclosure.

Without being bound by theory, it is surmised that encapsulation of therapeutic agents into liposomes results in some portion of the therapeutic agent becoming associated with or trapped within the lipid bilayer, particularly when encapsulating therapeutic agents with low water solubility or high hydrophobicity. Purifying the liposomal composition with an acidified aqueous solution may remove therapeutic agent that is associated with or trapped within the lipid bilayer, resulting in a liposome formulation that contains a therapeutic agent that is only encapsulated within the internal medium of the liposomes. For example, as shown in FIG. 3, as an exemplary liposome formulation containing Compound 9 is washed with an acidified aqueous sugar solution, Compound 9 is detected in the permeate. As the washing volume increases—that is, as the liposomal composition is washed with an increasing amount of acidified aqueous sugar solution—the amount of Compound 9 detected in the permeate peaks, and then decreases. The peak is thought to result from a rapid release of Compound 9 that is associated with or trapped in the lipid bilayer into the acidified aqueous sugar solution. FIG. 3 further shows that after washing with about 300-400 mL of acidified aqueous sugar solution, little Compound 9 is detected in the permeate—meaning that, by this point, most or all of Compound 9 has been removed from the lipid bilayer. In other words, purifying the liposomal composition with an acidified aqueous solution may allow for any therapeutic agent merely associated with or trapped within the lipid bilayer to release into the acidified aqueous solution, thus preventing a rapid release from occurring in the bloodstream of a patient upon administration. Consequently, liposomal compositions prepared according to various embodiments described herein may be expected to exhibit superior pharmacokinetic properties and enhanced clinical value.

In a first aspect, provided is a method of preparing a purified liposomal composition comprising:

liposomes comprising:

(a) a lipid bilayer;

(b) an internal medium; and (c) a therapeutic agent encapsulated in the internal medium of the liposomes, wherein the therapeutic agent has low water solubility and can be protonated to a protonated form;

said method comprising:

(i) providing a crude liposomal composition; and (ii) purifying the crude liposomal composition with an acidified aqueous solution.

In another aspect, provided is a liposomal composition prepared as described herein, comprising one or more liposomes, wherein each of the one or more liposomes comprises:

(a) a lipid bilayer comprising a first lipid and a first sterol;
(b) an internal medium comprising a first loading aid and a first solvent; and
(c) a therapeutic agent encapsulated in the internal medium of said liposome.

In another aspect, provided is a pharmaceutical composition comprising one or more liposomal compositions prepared as described herein, comprising one or more liposomes, wherein each of the one or more liposomes comprises:

(a) a lipid bilayer comprising a first lipid and a first sterol;
(b) an internal medium comprising a first loading aid and a first solvent; and
(c) a therapeutic agent encapsulated in the internal medium of said liposome; and a therapeutic agent external to the one or more liposomes.

In another aspect, provided is a method for delivering a therapeutically effective amount of a therapeutic agent to a subject comprising administering to the subject a liposomal composition prepared as described herein, comprising one or more liposomes, wherein each of the one or more liposomes comprises:

(a) a lipid bilayer comprising a first lipid and a first sterol;
(b) an internal medium comprising a first loading aid and a first solvent; and
(c) a therapeutic agent encapsulated in the internal medium of said liposome.

In another aspect, provided is a method for treating a hyperproliferative disorder in a subject in need thereof, the method comprising administering to the subject a liposomal composition prepared as described herein, comprising one or more liposomes, wherein each of the one or more liposomes comprises:

(a) a lipid bilayer comprising a first lipid and a first sterol;
(b) an internal medium comprising a first loading aid and a first solvent; and
(c) a therapeutic agent encapsulated in the internal medium of said liposome.

In some embodiments of all the aforementioned aspects, the first lipid is a polymer-conjugated lipid. In some embodiments, the polymer-conjugated lipid is selected from the group consisting of 1,2-distearoyl-rac-glycero-3-methoxypoly(ethylene glycol) (such as DSG-PEG2000), 1,2-dimyristoyl-rac-glycero-3-methoxypoly(ethylene glycol) (such as DMG-PEG2000), 1,2-dipalmitoyl-rac-glycero-3-methoxypoly(ethylene glycol) (such as DPG-PEG2000), and 1,2-distearoyl-sn-glycero-3-phosphoethanolamine-poly (ethylene glycol) (such as DSPE-PEG2000). In some embodiments, the polymer-conjugated lipid is 1,2-distearoyl-rac-glycero-3-methoxypoly(ethylene glycol) or 1,2-dimyristoyl-rac-glycero-3-methoxypoly(ethylene glycol). In some embodiments, the polymer-conjugated lipid is 1,2-distearoyl-rac-glycero-3-methoxypoly(ethylene glycol). In some embodiments, the polymer-conjugated lipid is DSG-PEG2000. In some embodiments, the lipid bilayer further comprises a second lipid. In some embodiments, the second lipid is a phospholipid. In some embodiments, the phospholipid is selected from the group consisting of a phosphatidylcholine, a sphingolipid, and a hydrogenated sphingolipid. In some embodiments, the second lipid is distearoyl phosphatidyl choline (DSPC). In some embodiments, the second lipid is sphingomyelin. In some embodiments, the second lipid is hydrogenated sphingomyelin (dihydrosphingomyelin). In some embodiments, the second lipid is egg sphingomyelin. In some embodiments, the second lipid is hydrogenated sphingomyelin (dihydrosphingomyelin) or egg sphingomyelin.

In some embodiments of all the aforementioned aspects, the first lipid is a first phospholipid. In some embodiments, the phospholipid is selected from the group consisting of a phosphatidylcholine, a sphingolipid, and a hydrogenated sphingolipid. In some embodiments, the first lipid is distearoyl phosphatidyl choline (DSPC). In some embodiments, the first lipid is sphingomyelin. In some embodiments, the first lipid is hydrogenated sphingomyelin (dihydrosphingomyelin). In some embodiments, the lipid bilayer further comprises a second lipid. In some embodiments, the second lipid is a second phospholipid. In some embodiments, the second phospholipid is selected from the group consisting of a phosphatidylcholine, a sphingolipid, and a hydrogenated sphingolipid (dihydrosphingomyelin). In some embodiments, the second lipid is distearoyl phosphatidyl glycerol (DSPG). In some embodiments, the second lipid is sphingomyelin. In some embodiments, the second lipid is hydrogenated sphingomyelin (dihydrosphingomyelin).

In some embodiments of all the aforementioned aspects, the first solvent is an aqueous solvent. In some embodiments, the aqueous solvent is an acidic aqueous solvent.

In some embodiments of all the aforementioned aspects, the internal medium further comprises a second solvent. In some embodiments, the second solvent is an organic solvent. In some embodiments, the organic solvent is an aprotic organic solvent. In some embodiments, the second solvent is dimethylsulfoxide (DMSO).

In some embodiments of all the aforementioned aspects, first loading aid is an ionic loading aid. In some embodiments, the first loading aid forms an ionic gradient across the lipid bilayer. In some embodiments, the ionic gradient is a pH gradient, a sulfate gradient, a phosphate gradient, a citrate gradient, an acetate gradient, an EDTA-ion gradient, an ammonium gradient, an alkylammonium gradient, an amylammonium gradient, a Ca gradient, a Cu gradient, a Fe gradient, a Mg gradient, a Mn gradient, a Zn gradient, a Na gradient, or a K gradient. In some embodiments, the first loading aid is a sulfate salt, a sucrose octasulfate salt, or a citrate salt. In some embodiments, the first loading aid is selected from the group consisting of ammonium sulfate (AS), ammonium sucrose octasulfate (NH4SOS), potassium sucrose octasulfate (KSOS), triethylammonium sucrose octasulfate (TEASOS), triethanolammonium sucrose octasulfate (TEA(OH)SOS), ammonium citrate, and sodium citrate. In some embodiments, the first loading aid is selected from the group consisting of ammonium sulfate (AS), ammonium sucrose octasulfate (NH4SOS), potassium sucrose octasulfate (KSOS), triethylammonium sucrose octasulfate (TEASOS), and sodium citrate. In some embodiments, the first loading aid is ammonium sulfate (AS). In some embodiments, the first loading aid is ammonium sucrose octasulfate (NH4SOS). In some embodiments, the first loading aid is potassium sucrose octasulfate (KSOS). In some embodiments, the first loading aid is triethylammonium sucrose octasulfate (TEASOS). In some embodiments, the first loading aid is sodium citrate. In some embodiments, the internal medium further comprises a second loading aid. In some embodiments, the second loading aid is an ionic loading aid. In some embodiments, the second loading aid is a sulfate salt, a sucrose octasulfate salt, or a citrate salt. In some embodiments, the second loading aid is selected from the group consisting of ammonium sulfate (AS), ammonium sucrose octasulfate (NH4SOS), potassium sucrose octasulfate (KSOS), triethylammonium sucrose octasulfate (TEASOS), triethanolammonium sucrose octasulfate (TEA (OH)SOS), ammonium citrate, and sodium citrate. In some embodiments, the second loading aid is ammonium sulfate (AS). In some embodiments, the second loading aid is ammonium sucrose octasulfate (NH4SOS). In some embodiments, the second loading aid is potassium sucrose octasulfate (KSOS). In some embodiments, the second loading aid is triethylammonium sucrose octasulfate (TEASOS). In some embodiments, the second loading aid is sodium citrate. In some embodiments, the first loading aid is potassium sucrose octasulfate (KSOS) and the second loading aid is sodium citrate.

In some embodiments of all the aforementioned aspects, the first sterol is cholesterol or a phytosterol (such as beta-sitosterol). In some embodiments, the first sterol is cholesterol. In some embodiments, the first sterol is beta-sitosterol.

In some embodiments, the liposomes and liposomal compositions provided therein comprise a therapeutic agent encapsulated in the liposomes. In some embodiments, the liposomes and liposomal compositions provided therein comprise a hydrophobic therapeutic agent encapsulated in the liposomes.

In some embodiments, the therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor.

In some embodiments, the therapeutic agent is an HSP90 inhibitor. In some embodiments, the HSP90 inhibitor is Luminespib.

In some embodiments, the therapeutic agent is an alkylating agent. In some embodiments, the therapeutic agent is an alkylating agent selected from the group consisting of Bendamustine and Chlorambucil.

In some embodiments, the therapeutic agent is an antitubulin agent. In some embodiments, the therapeutic agent is an antitubulin agent selected from the group consisting of Vincristine, Vinorelbine, and docetaxel.

In some embodiments, the therapeutic agent is an ATR inhibitor.

In some embodiments, the therapeutic agent is a RAF inhibitor. In some embodiments, the RAF inhibitor is Dabrafenib. In some embodiments, the therapeutic agent is a BRAF inhibitor. In some embodiments, the BRAF inhibitor is Vemurafenib.

In some embodiments, the therapeutic agent is a BTK inhibitor. In some embodiments, the BTK inhibitor is Ibrutinib.

In some embodiments, the therapeutic agent is an HDAC inhibitor. In some embodiments, the HDAC inhibitor is Panobinostat.

In some embodiments, the therapeutic agent is a JAK inhibitor. In some embodiments, the JAK inhibitor is Ruxolitinib.

In some embodiments, the therapeutic agent is an MEK inhibitor. In some embodiments, the therapeutic agent is an MEK inhibitor selected from the group consisting of Selumetinib and Cobimetinib.

In some embodiments, the therapeutic agent is a PARP inhibitor. In some embodiments, the therapeutic agent is a PARP inhibitor selected from the group consisting of Talazoparib, Niraparib, and Rucaparib.

In some embodiments, the therapeutic agent is a PI3K inhibitor. In some embodiments, the PI3K inhibitor is Idelalisib.

In some embodiments, the therapeutic agent is a proteasome inhibitor. In some embodiments, the proteasome inhibitor is Carfilzomib.

In some embodiments, the therapeutic agent is an SMO inhibitor. In some embodiments, the therapeutic agent is an SMO inhibitor selected from the group consisting of Sonidegib and Vismodegib.

In some embodiments, the therapeutic agent is a tyrosine kinase inhibitor. In some embodiments, the therapeutic agent is a tyrosine kinase inhibitor selected from the group consisting of Brigatinib, Lenvatinib, Afatinib, Axitinib, Cabozantinib, Ponatinib, Sorafenib, Osimertinib, Regorafenib, Bosutinib, Crizotinib, Vandetanib, Nilotinib, Alectinib, Ceritinib, Dasatinib, Pazopanib, Sunitinib, Erlotinib, Imatinib, Gefitinib, Lapatinib.

In some embodiments, the therapeutic agent is a topoisomerase inhibitor. In some embodiments, the therapeutic agent is a topoisomerase I inhibitor. In some embodiments, the topoisomerase inhibitor is Irinotecan.

In some embodiments, the therapeutic agent is a Bcl inhibitor. In some embodiments, the Bcl inhibitor is a Bcl-2 inhibitor. In some embodiments, the Bcl inhibitor is a Bcl-$X_L$ inhibitor. In some embodiments, the Bcl inhibitor is a Bcl-2/Bcl-$X_L$ dual inhibitor. In some embodiments, the Bcl inhibitor is a compound of Formula (I):

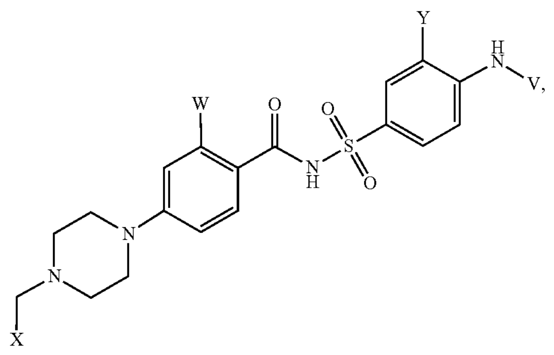

or a stereoisomer, tautomer, or pharmaceutically acceptable salt thereof, wherein:

V is

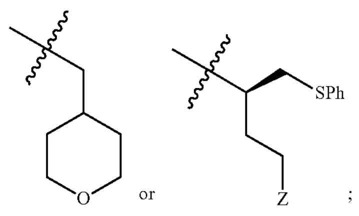

W is H
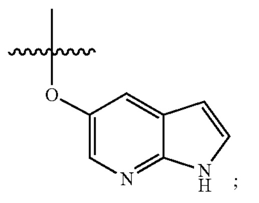 [SMILES: *Oc1cnc2[nH]ccc2c1]
X is
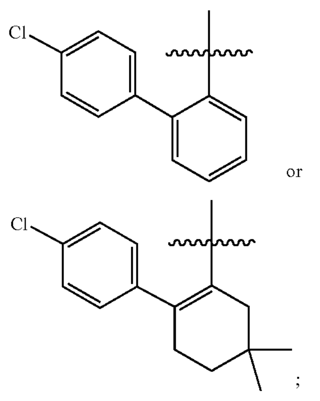
Y is —$NO_2$ or —$SO_2CF_3$;
Z is selected from the group consisting of
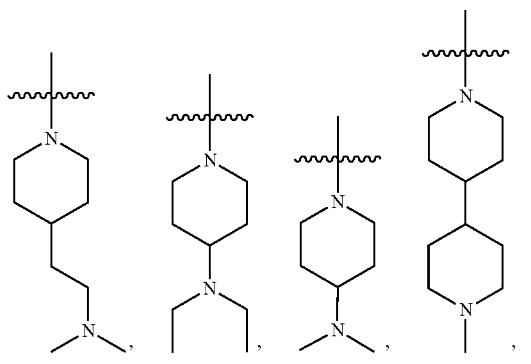
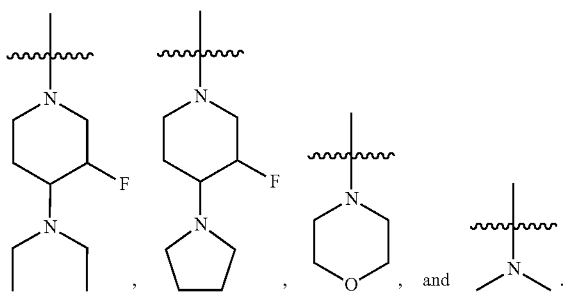
In some embodiments, V is
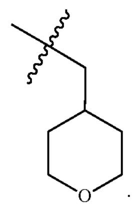 [SMILES: *CC1CCOCC1]
In some embodiments, V is
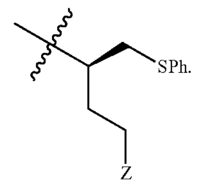
In some embodiments, W is H. In some embodiments, W
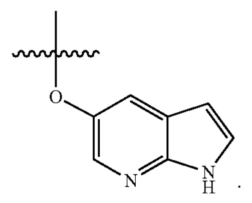 [SMILES: *Oc1cnc2[nH]ccc2c1]
In some embodiments, X is
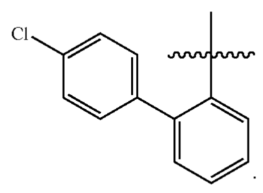 [SMILES: *c1ccccc1-c1ccc(Cl)cc1]
In some embodiments, X is
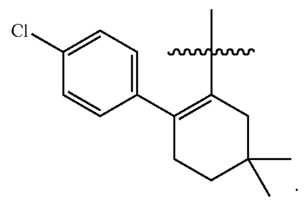 [SMILES: *C1=C(c2ccc(Cl)cc2)CCC(C)(C)C1]
In some embodiments, Y is —$NO_2$. In some embodiments, Y is —$SO_2CF_3$.

In some embodiments, Z
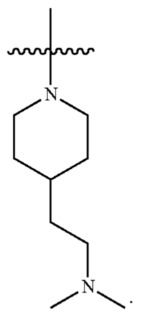 [SMILES: *N1CCC(CCN(C)C)CC1]
In some embodiments, Z is
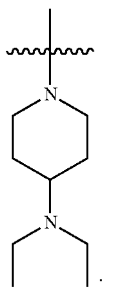 [SMILES: *N1CCC(N(CC)CC)CC1]
In some embodiments, Z is
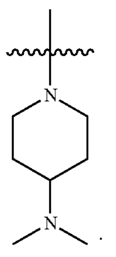 [SMILES: *N1CCC(N(C)C)CC1]
In some embodiments, Z is
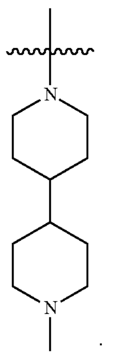 [SMILES: *N1CCC(C2CCN(C)CC2)CC1]
In some embodiments, Z is
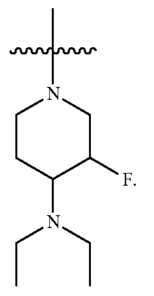 [SMILES: *N1CCC(N(CC)CC)C(F)C1]
In some embodiments, Z is
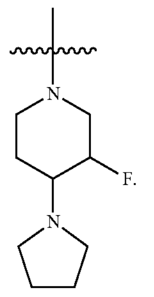 [SMILES: *N1CCC(N2CCCC2)C(F)C1]
In some embodiments, Z is
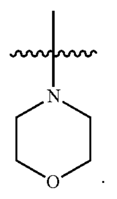
In some embodiments, Z is
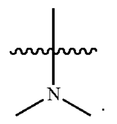
In some embodiments, the Bcl inhibitor is selected from the group consisting of Compound 1
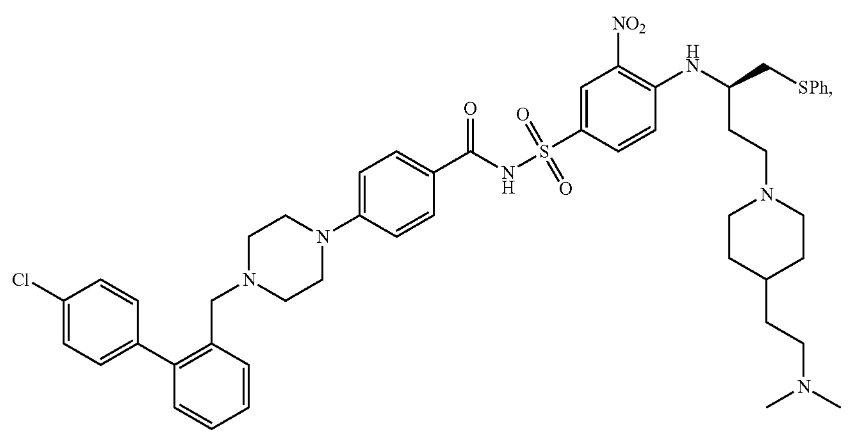
Compound 2
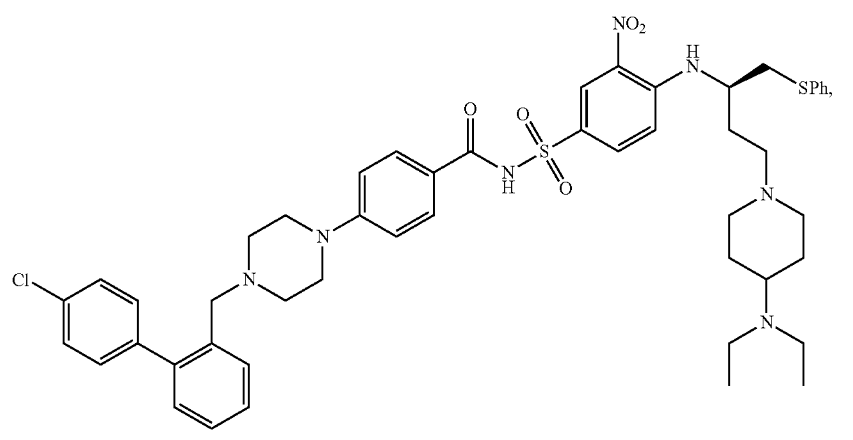
Compound 3
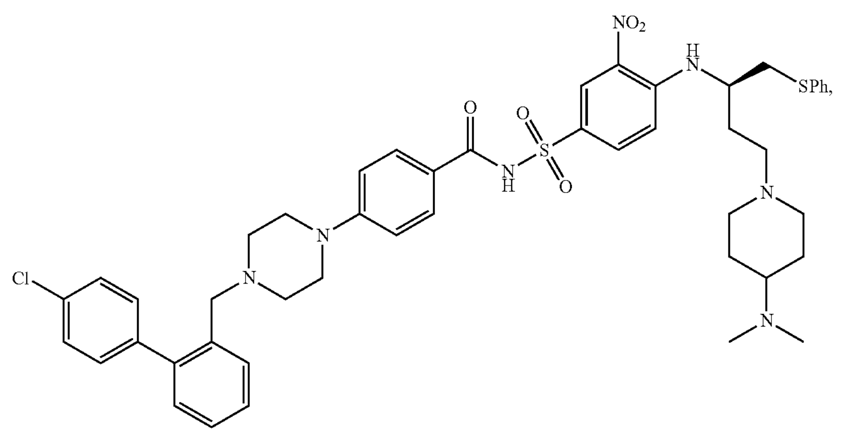

-continued
Compound 4
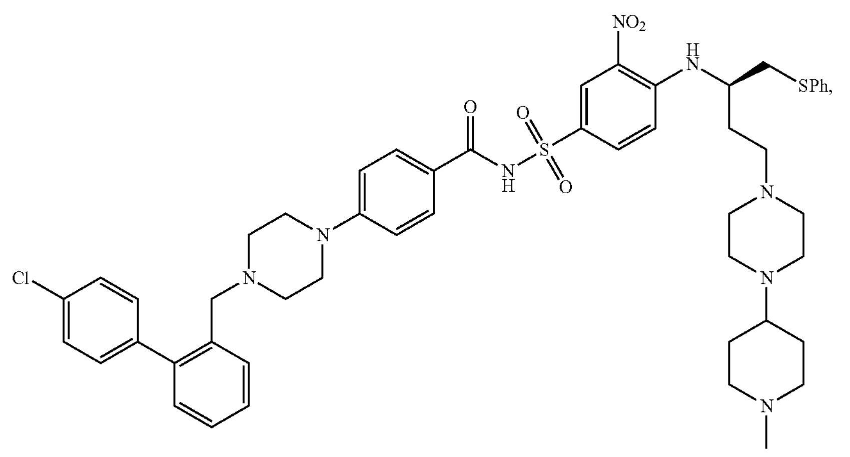
Compound 5
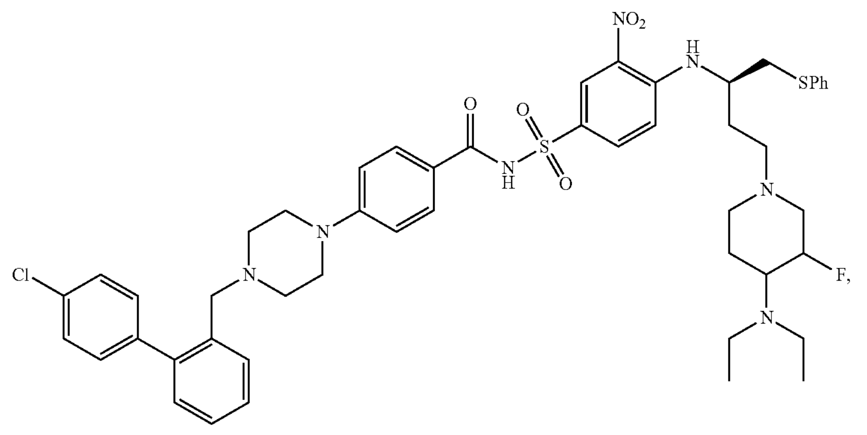
Compound 6
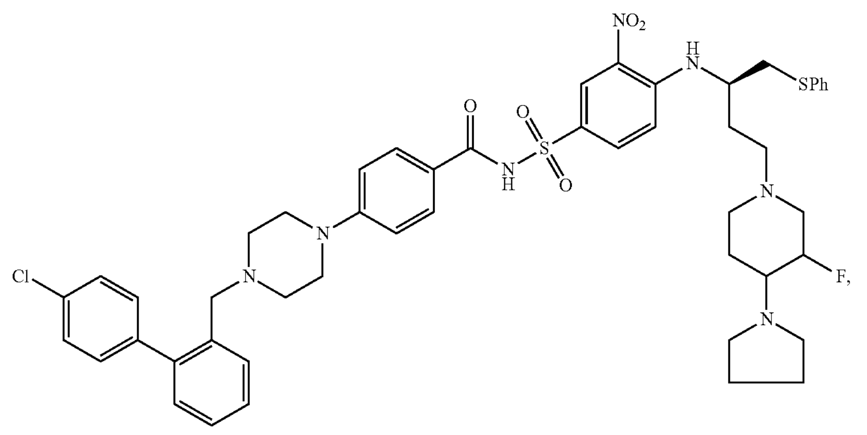

-continued
Compound 7
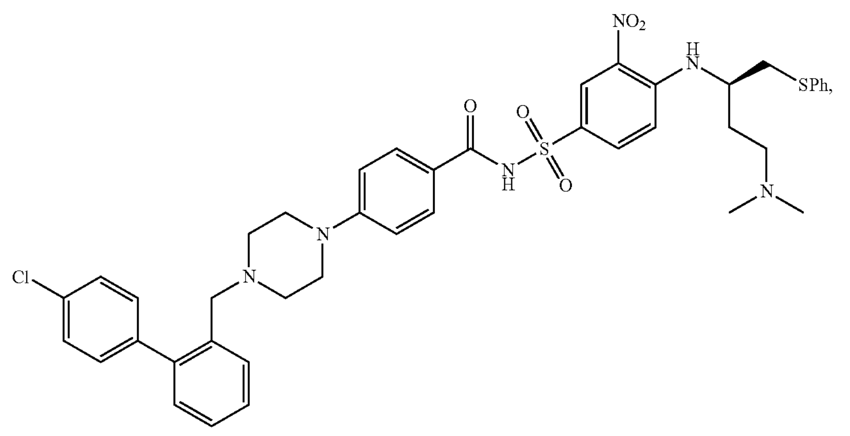
Compound 8
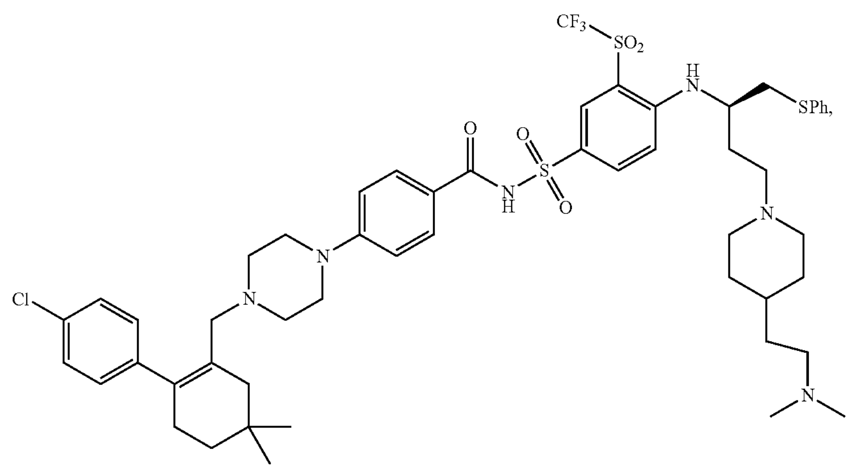
Compound 9
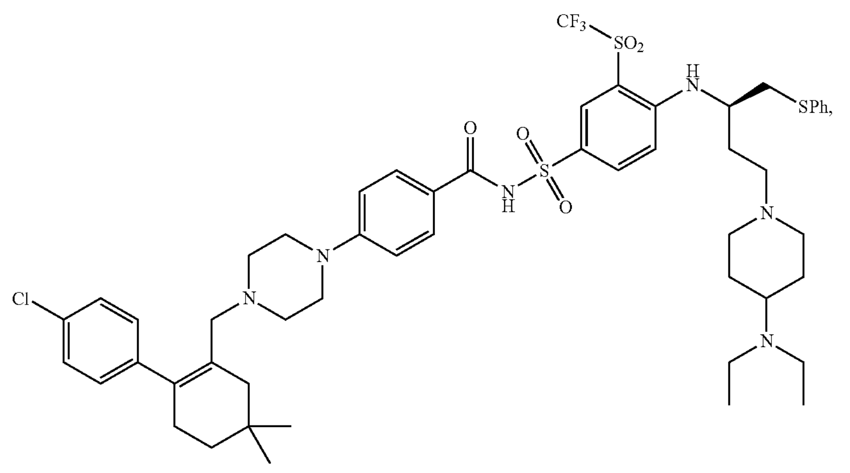

-continued
Compound 10
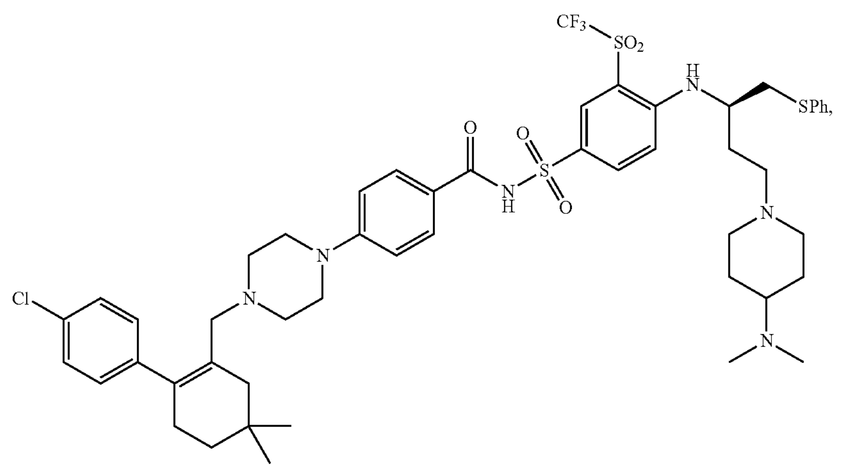
Compound 11
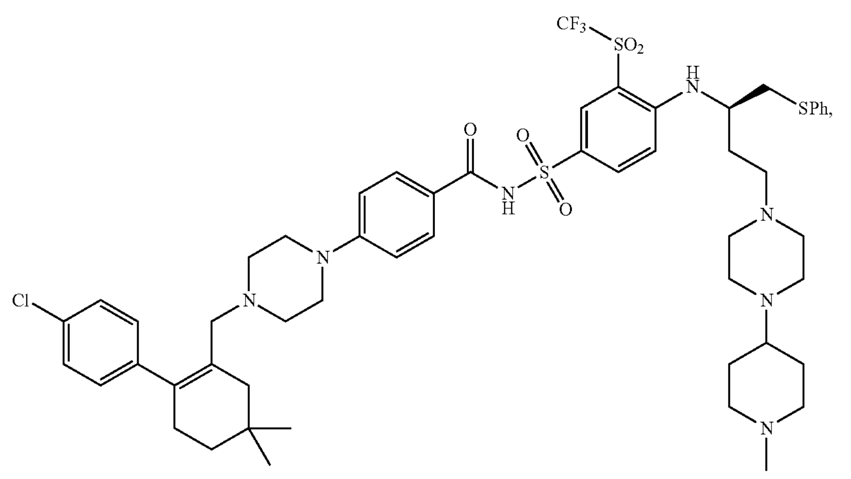
Compound 12
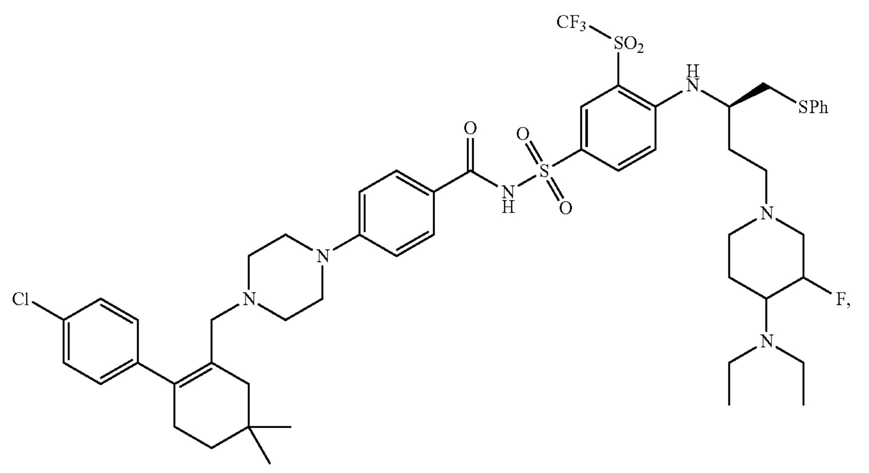

-continued
Compound 13
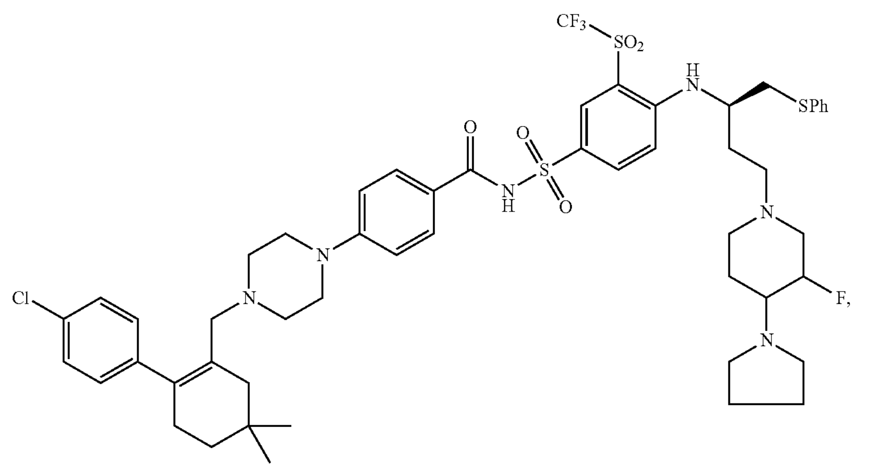
Compound 14
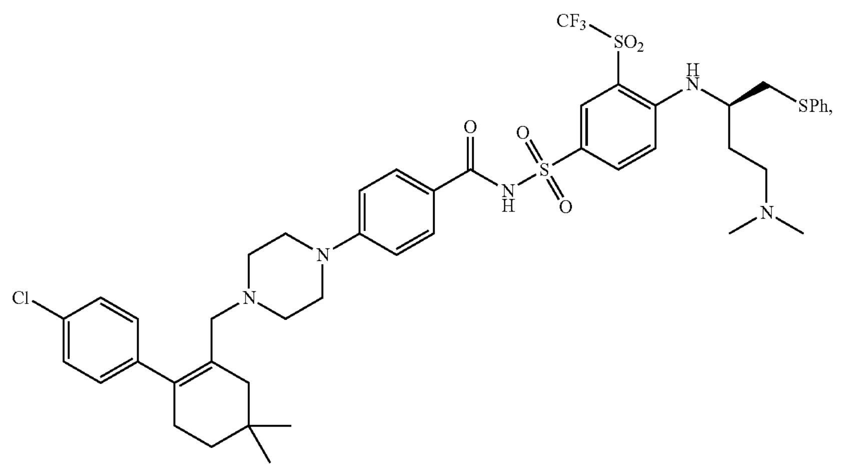
Compound 15
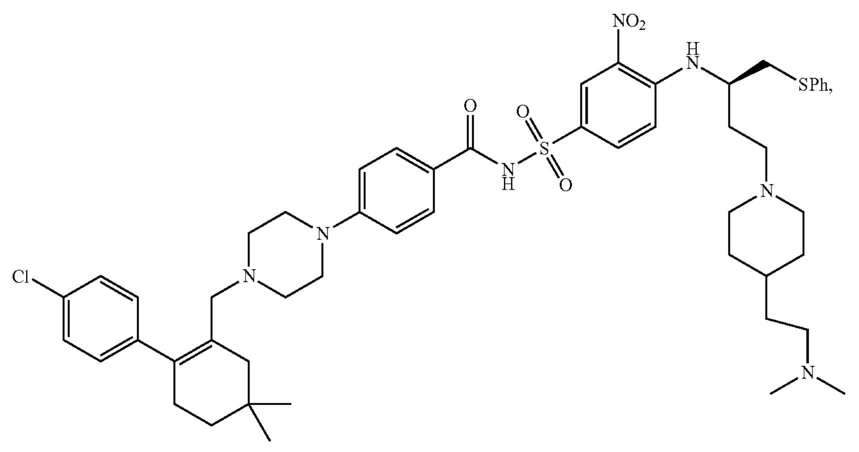

-continued
Compound 16
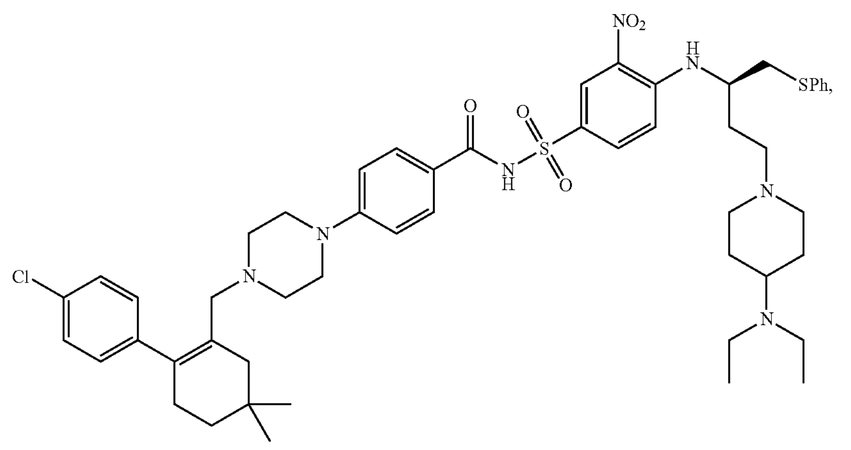
Compound 17
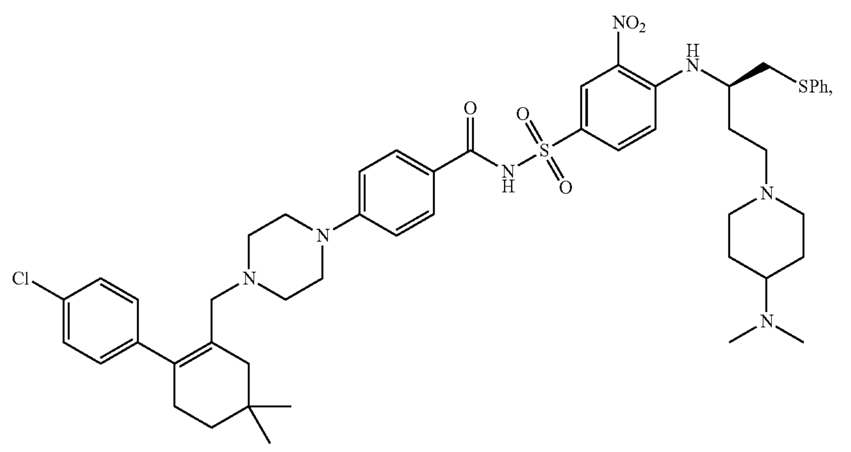
Compound 18
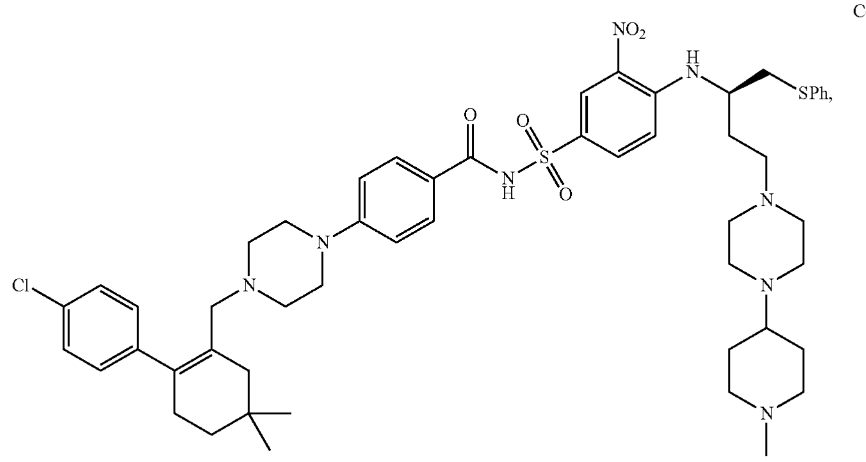

-continued
Compound 19
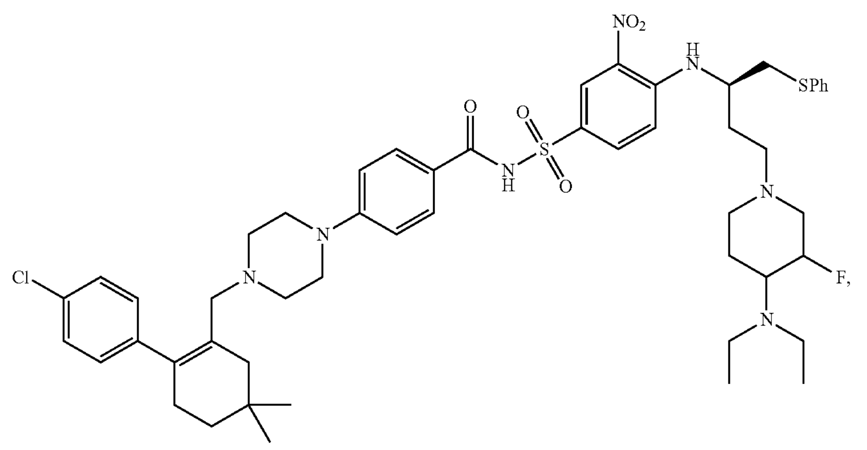
Compound 20
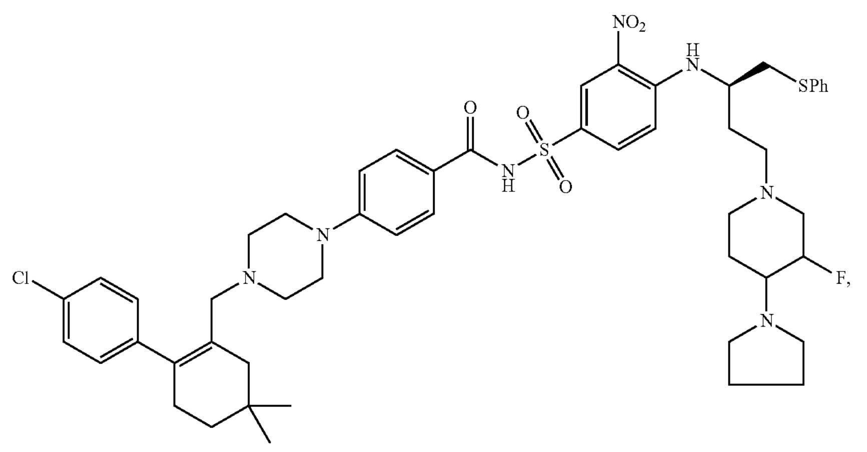
Compound 21
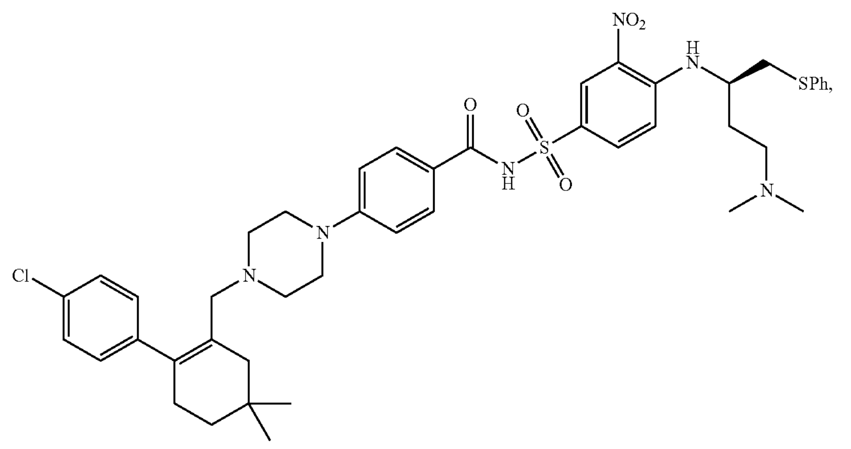

-continued
Compound 22
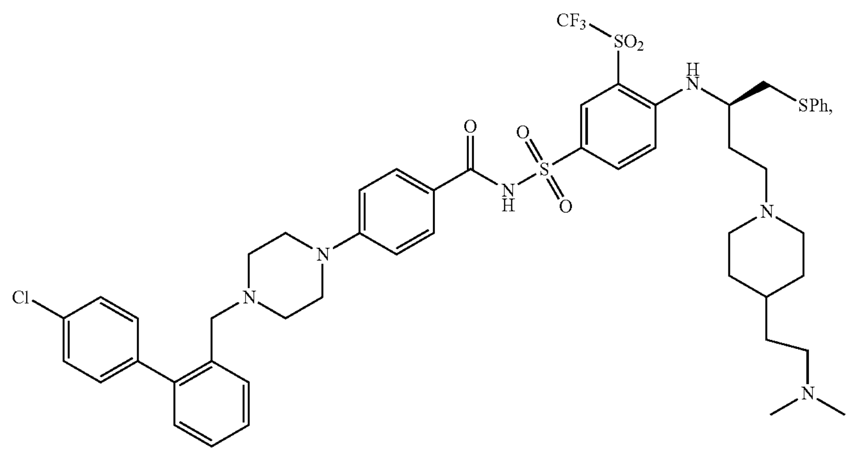
Compound 23
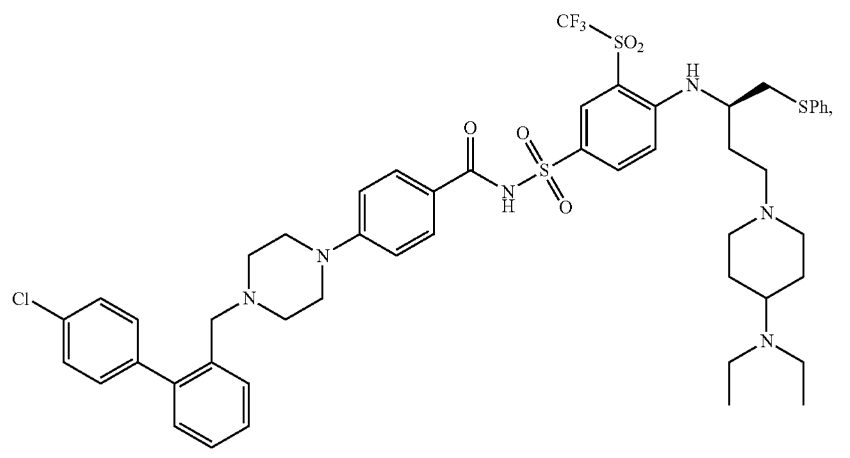
Compound 24
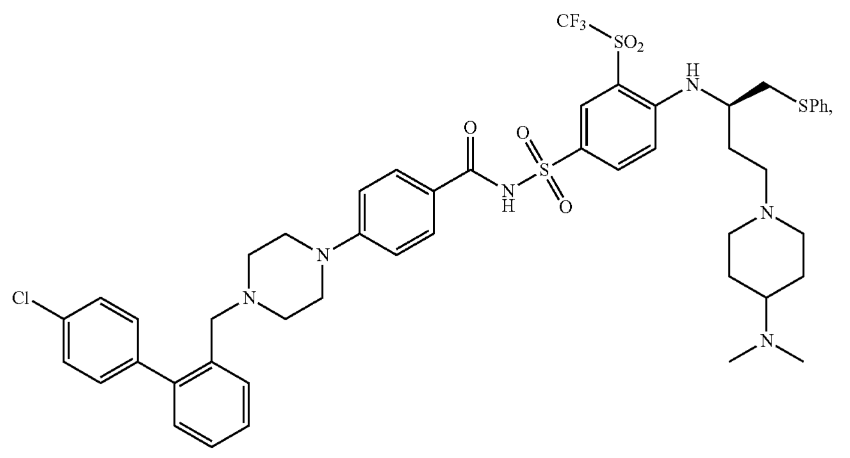

-continued
Compound 25
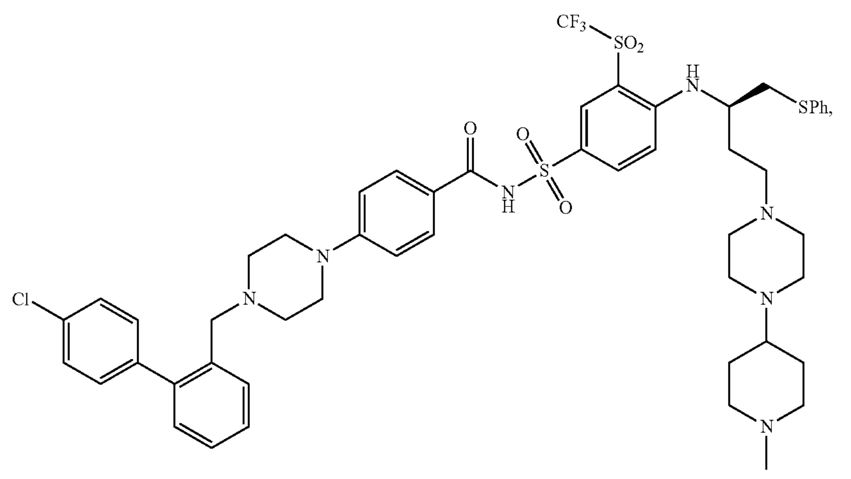
Compound 26
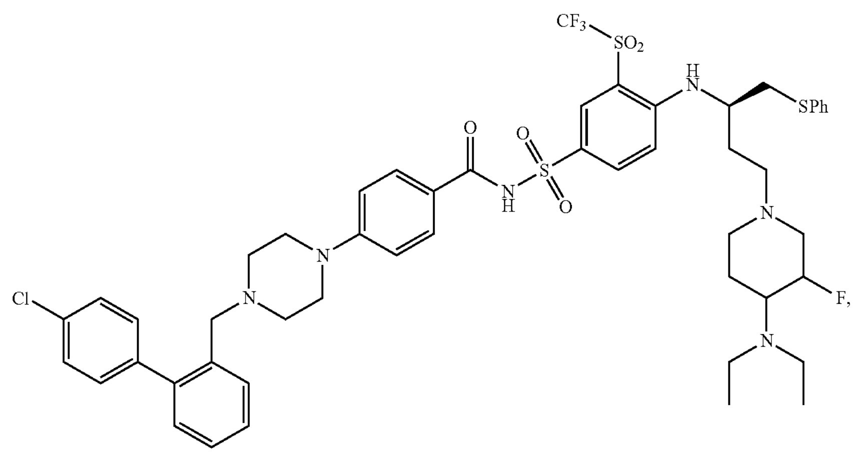
Compound 27
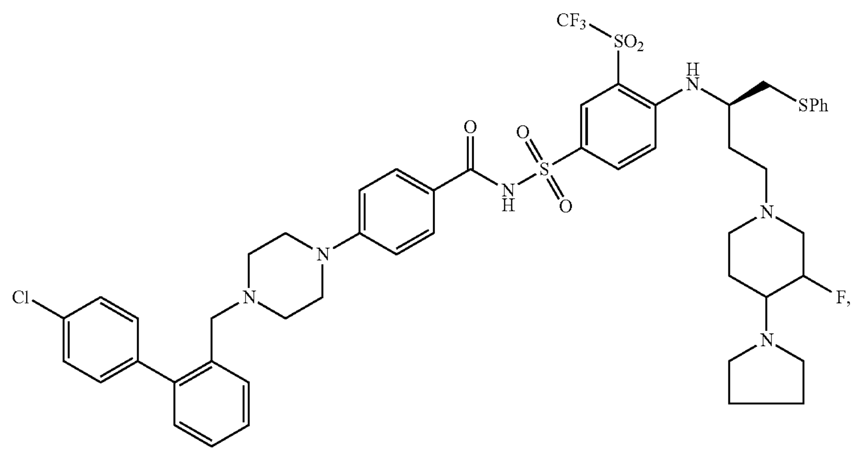

-continued
Compound 28
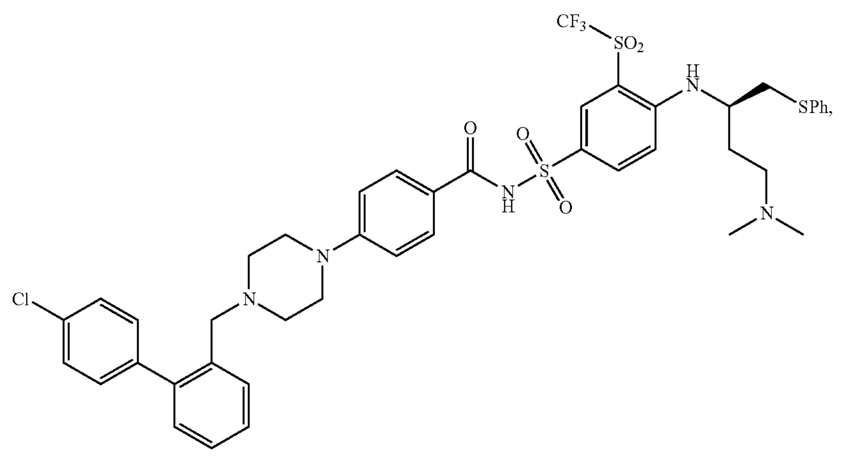
venetoclax (ABT-199), navitoclax (ABT-263), ABT-737, obatoclax mesylate (GX15-070), sabutoclax, TW-37, (R)-(−)-gossypol acetic acid, HA14-1, a BH3-mimetic, and oblimersen. In some embodiments, the Bcl inhibitor is selected from the group consisting of
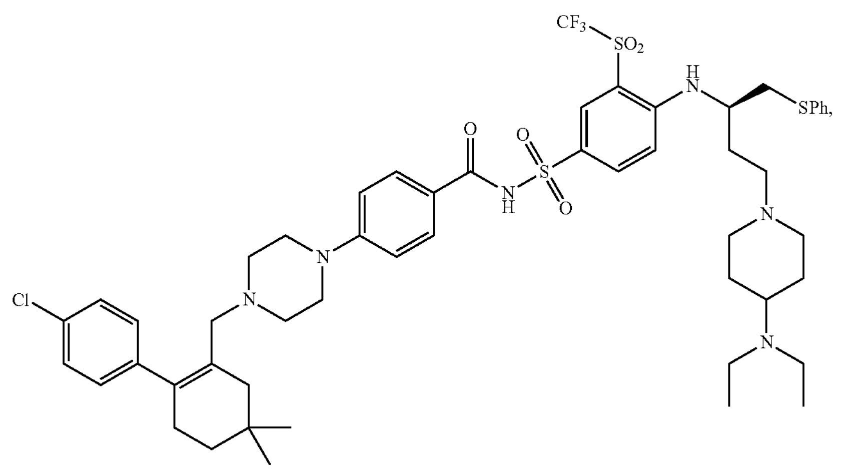
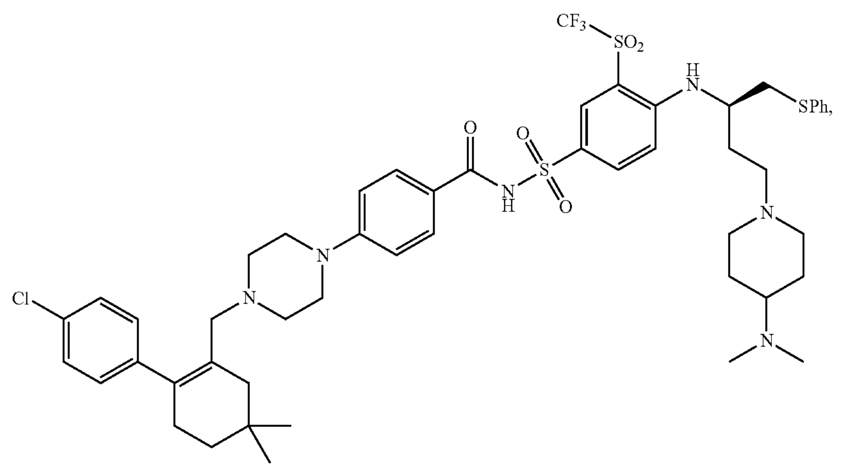

-continued
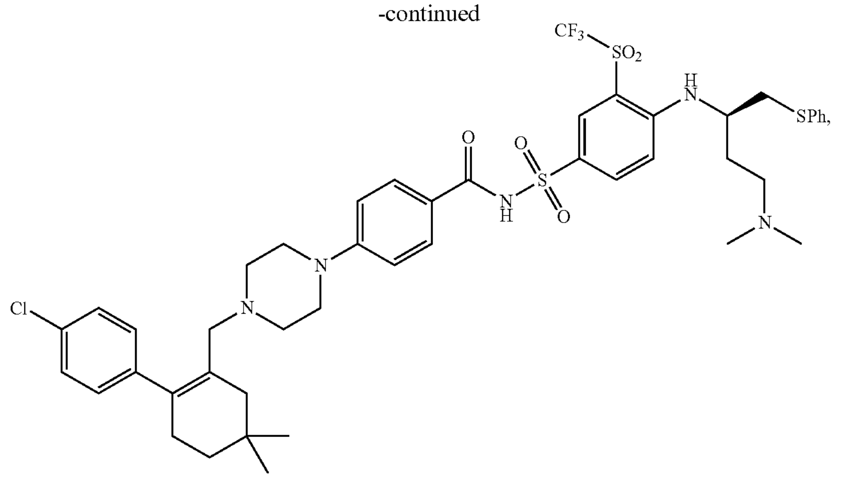
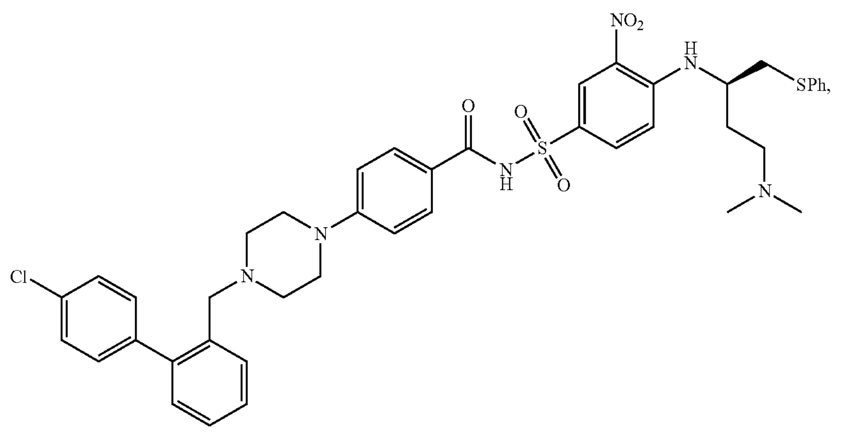
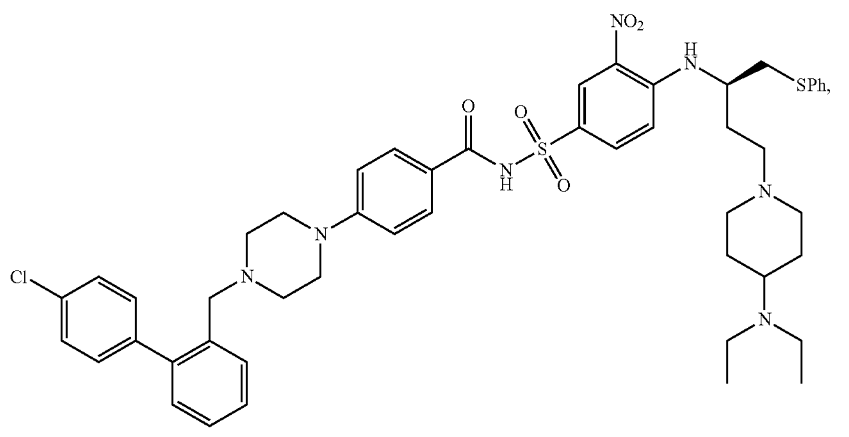
venetoclax (ABT-199), navitoclax (ABT-263), obatoclax mesylate (GX15-070), sabutoclax, TW-37, (R)-(−)-gossypol acetic acid, HA14-1, a BH3-mimetic, and oblimersen. In some embodiments, the Bcl inhibitor is selected from the group consisting of

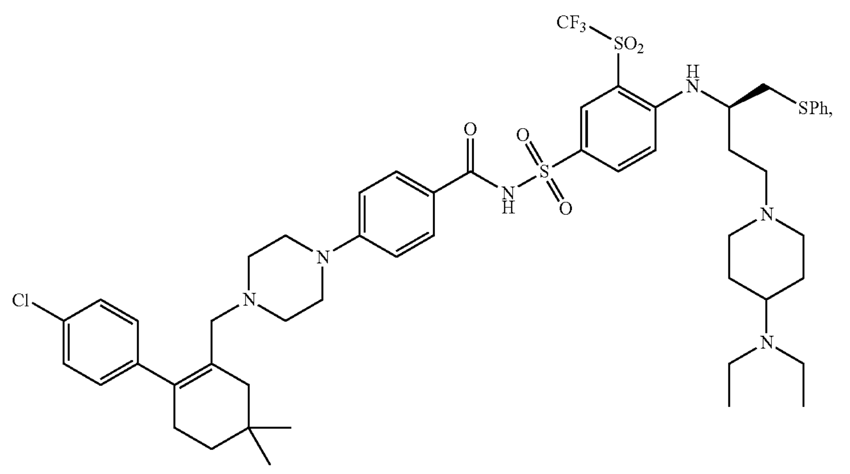
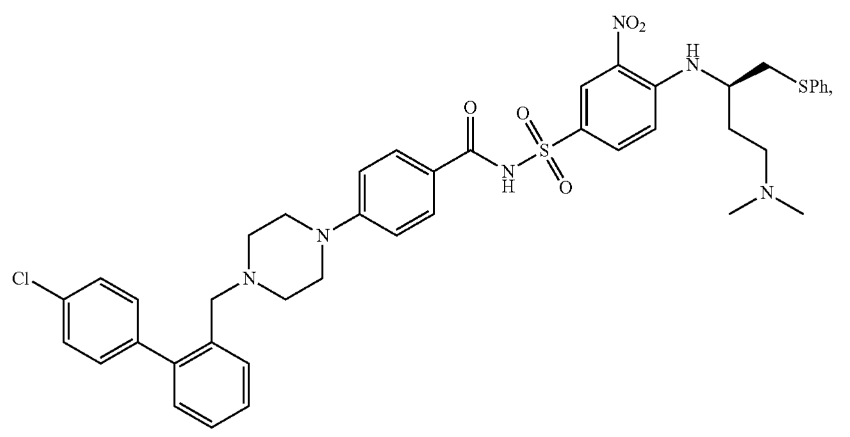
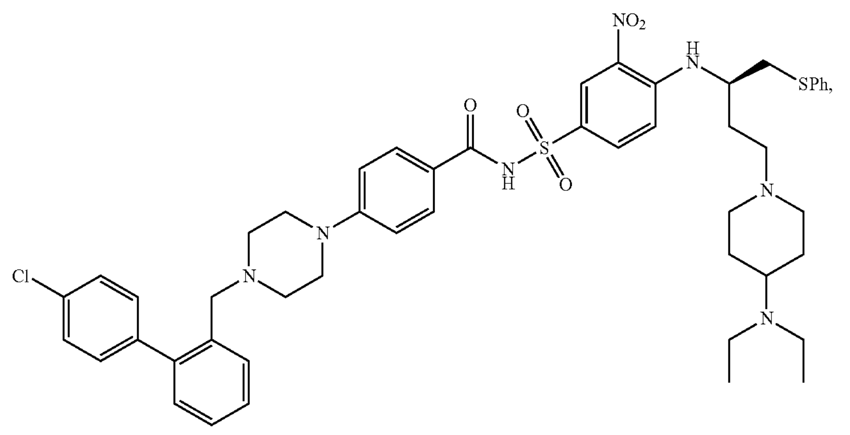
venetoclax (ABT-199), navitoclax (ABT-263), obatoclax mesylate (GX15-070), sabutoclax, TW-37, (R)-(−)-gossypol acetic acid, HA14-1, a BH3-mimetic, and oblimersen. In some embodiments, the Bcl inhibitor is selected from the group consisting of

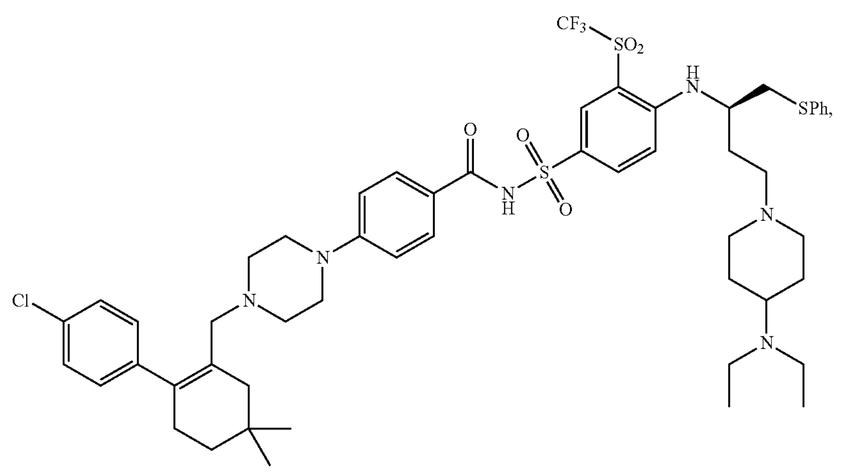
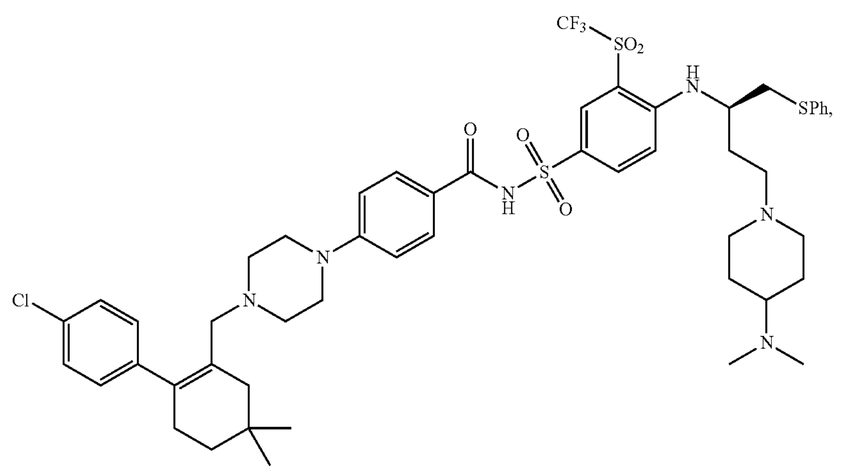
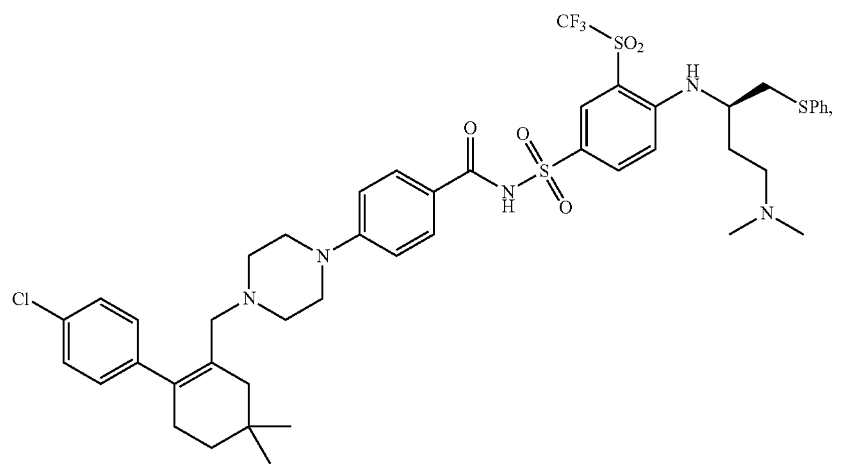

-continued
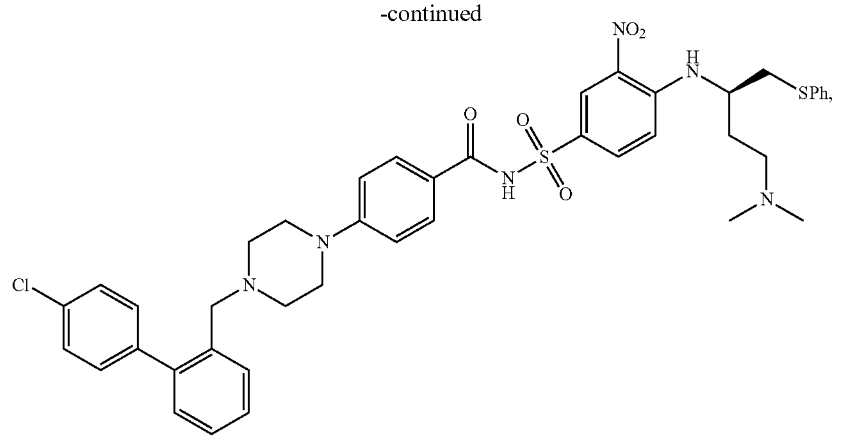
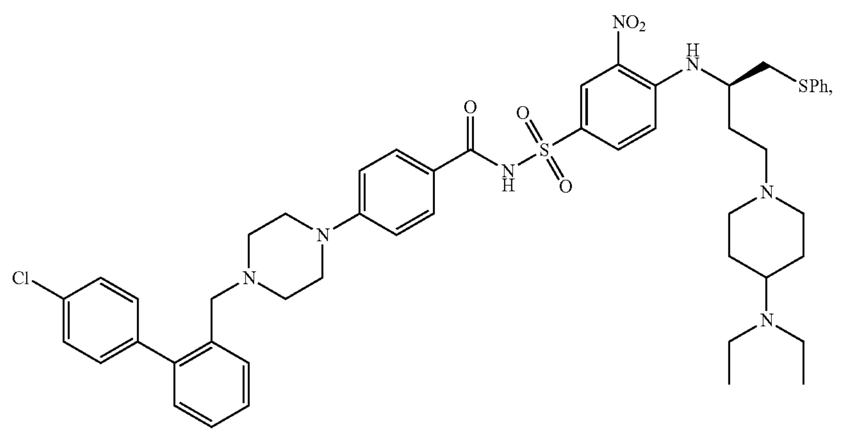
venetoclax (ABT-199), and navitoclax (ABT-263). In some embodiments, the Bcl inhibitor is selected from the group consisting of
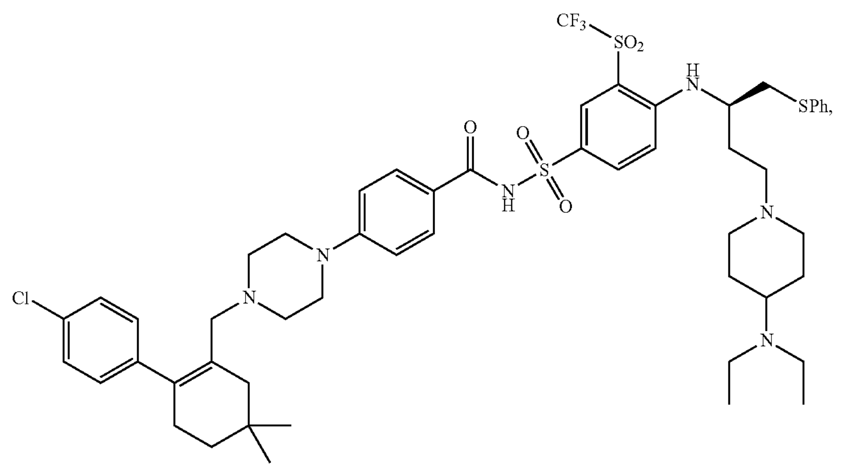

-continued
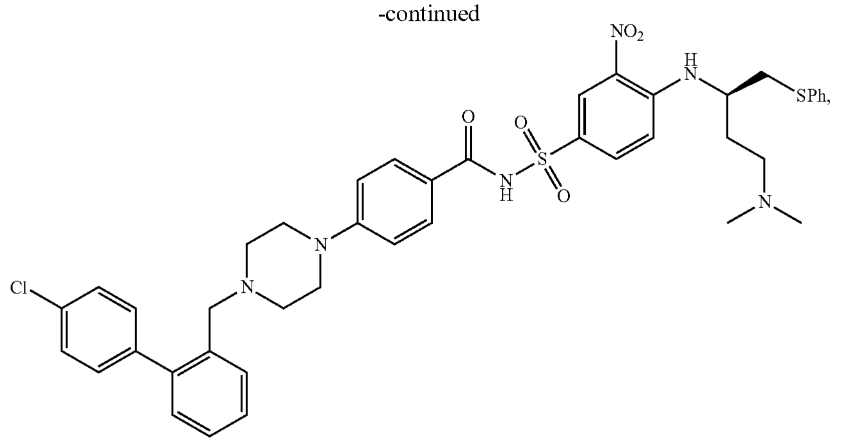
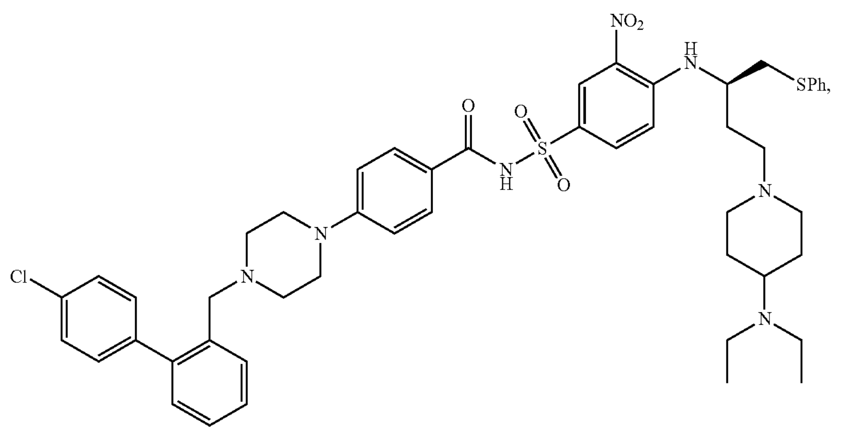
venetoclax (ABT-199), and navitoclax (ABT-263). In some embodiments, the Bcl inhibitor is
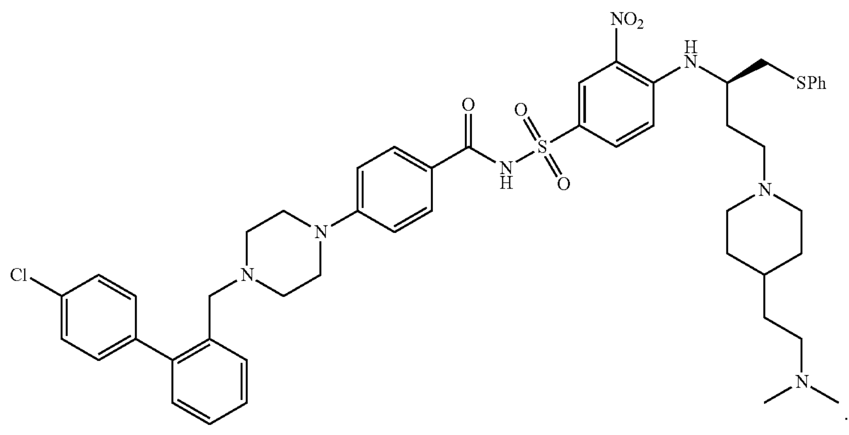

In some embodiments, the Bcl inhibitor is
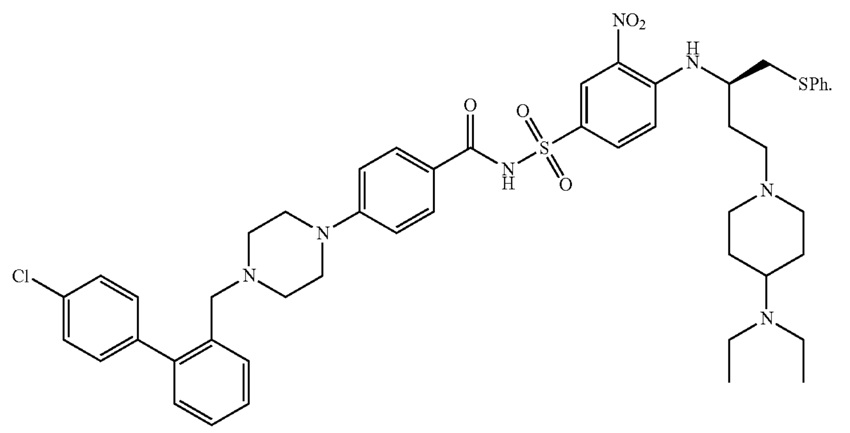
In some embodiments, the Bcl inhibitor is
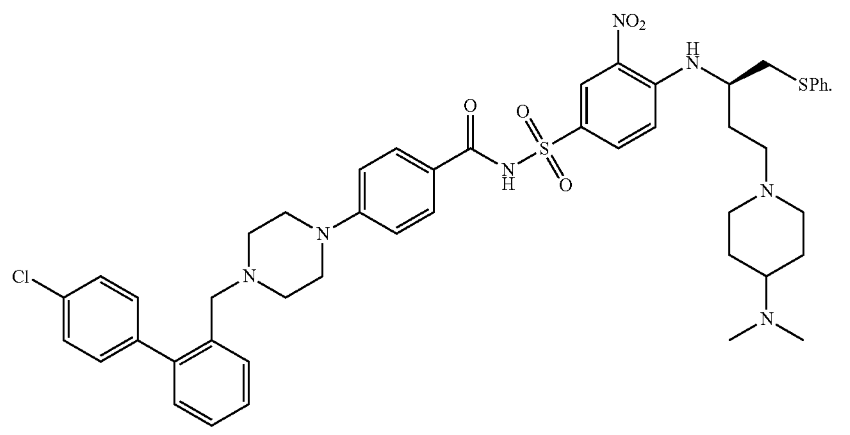
In some embodiments, the Bcl inhibitor is
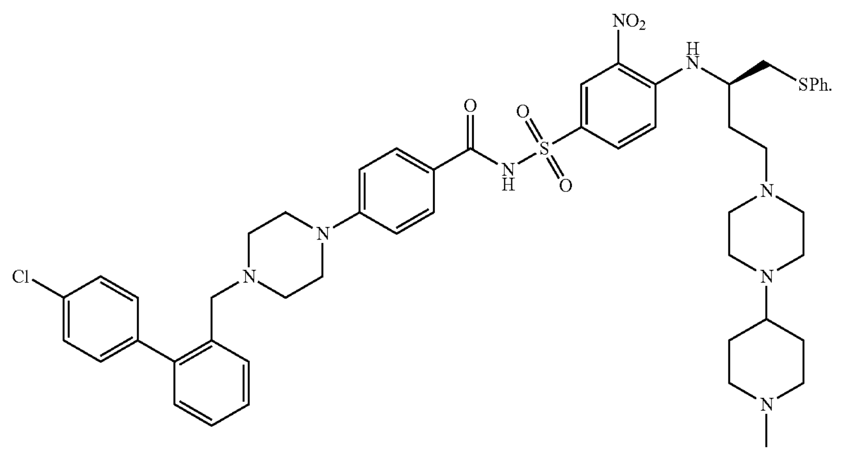

In some embodiments, the Bcl inhibitor is
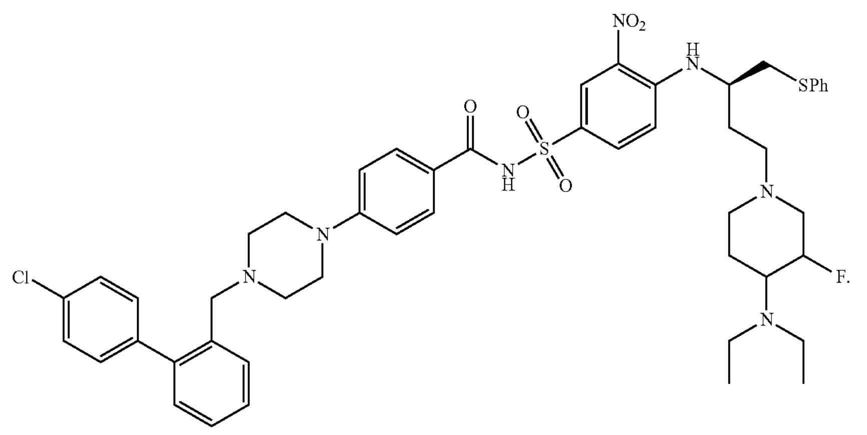
In some embodiments, the Bcl inhibitor is
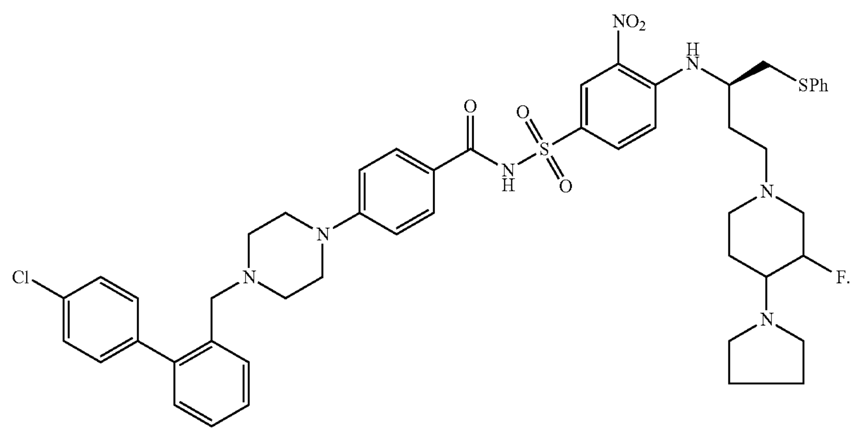
In some embodiments, the Bcl inhibitor is
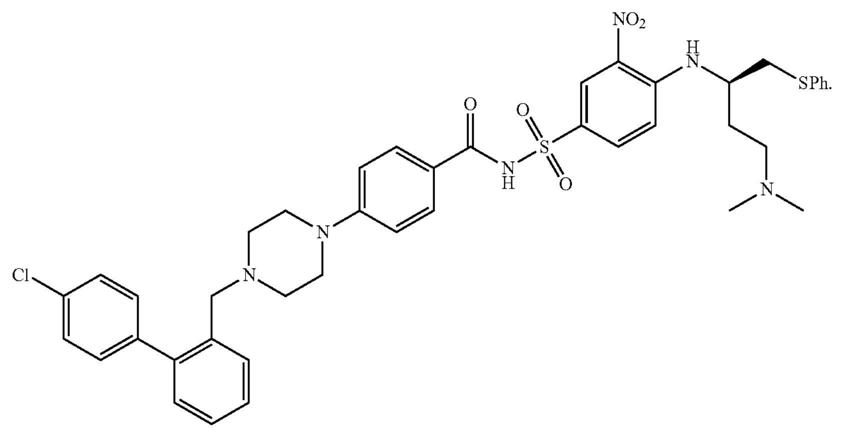

In some embodiments, the Bcl inhibitor is
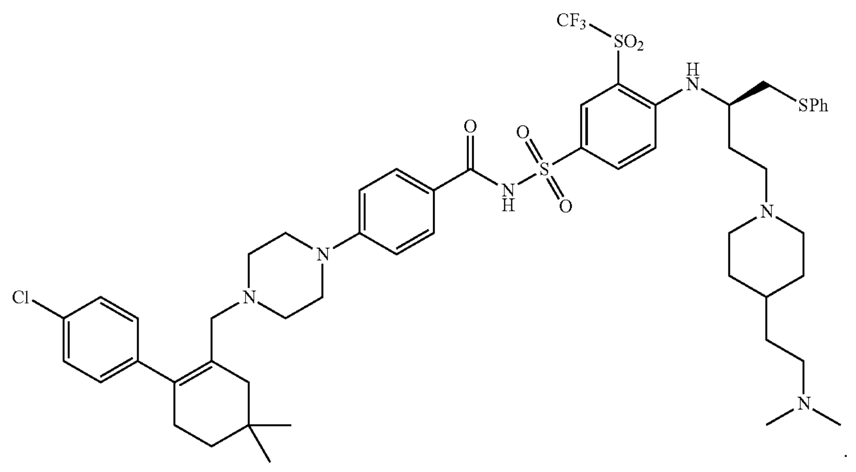
In some embodiments, the Bcl inhibitor is
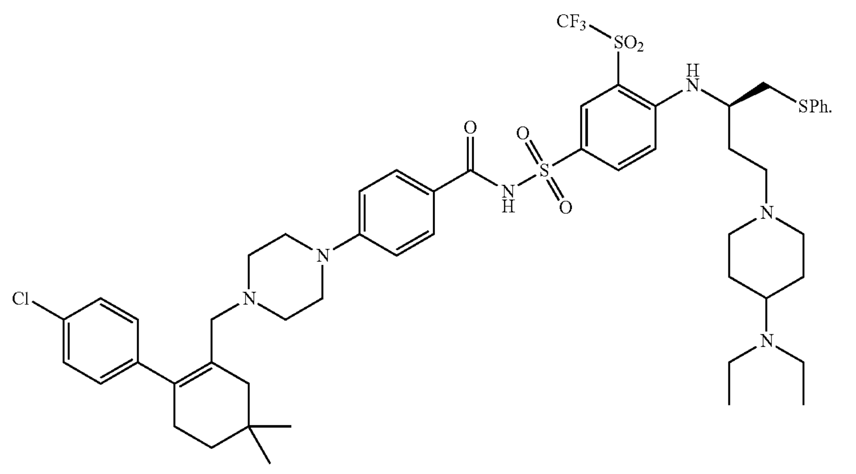
In some embodiments, the Bcl inhibitor is
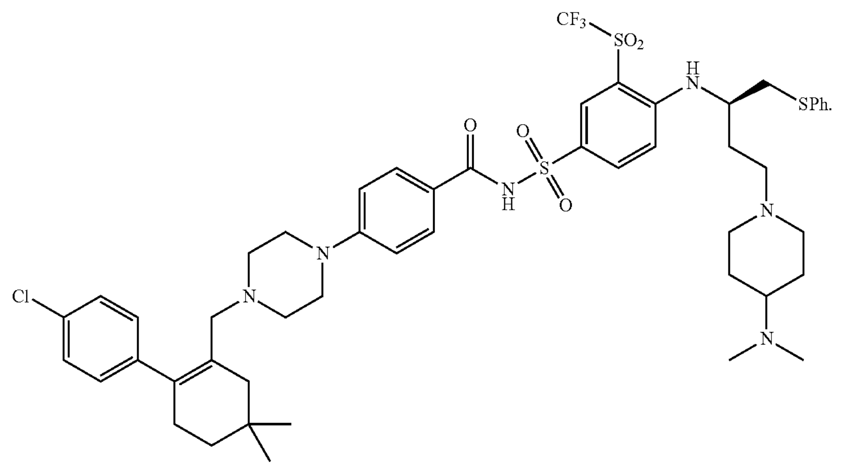

In some embodiments, the Bcl inhibitor is
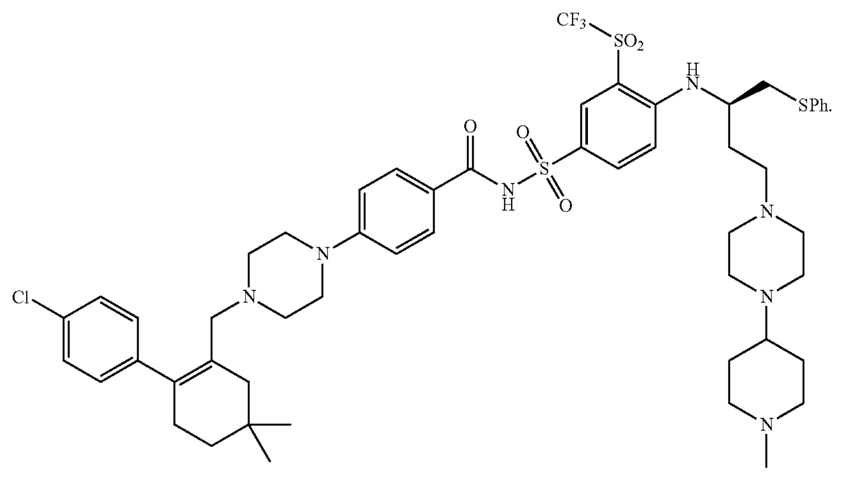
In some embodiments, the Bcl inhibitor is
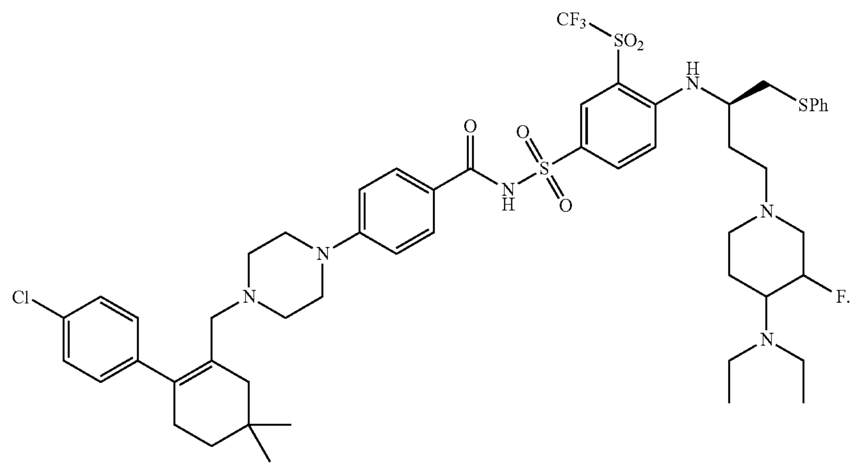
In some embodiments, the Bcl inhibitor is
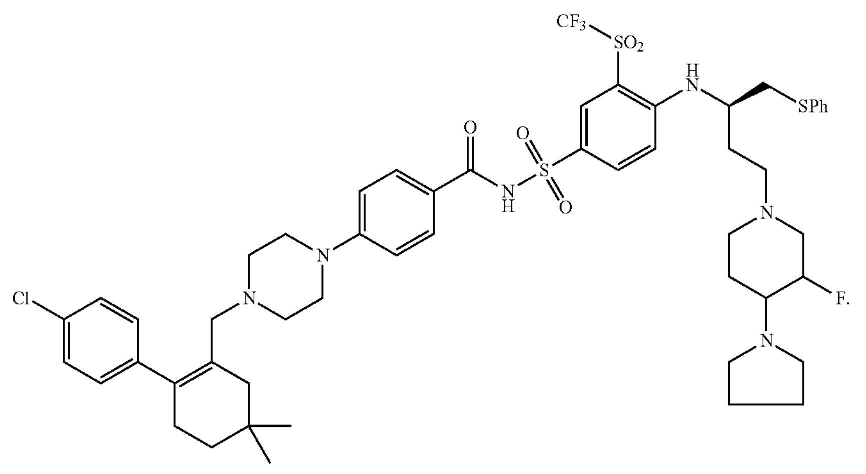

In some embodiments, the Bcl inhibitor is
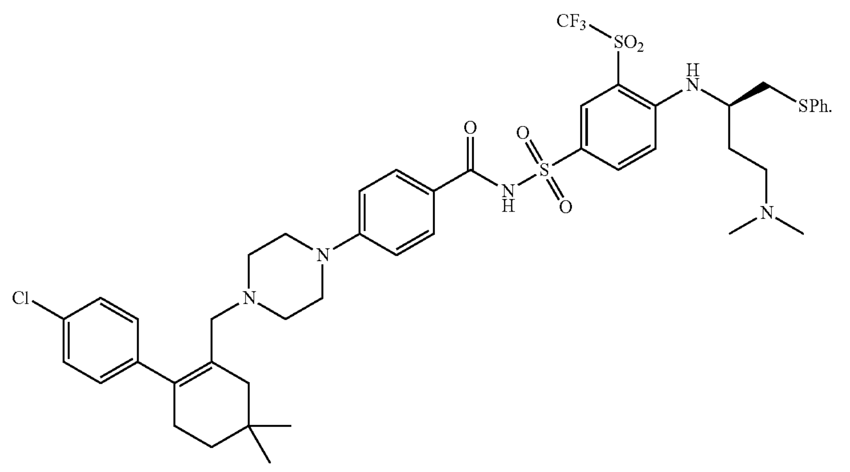
In some embodiments, the Bcl inhibitor is
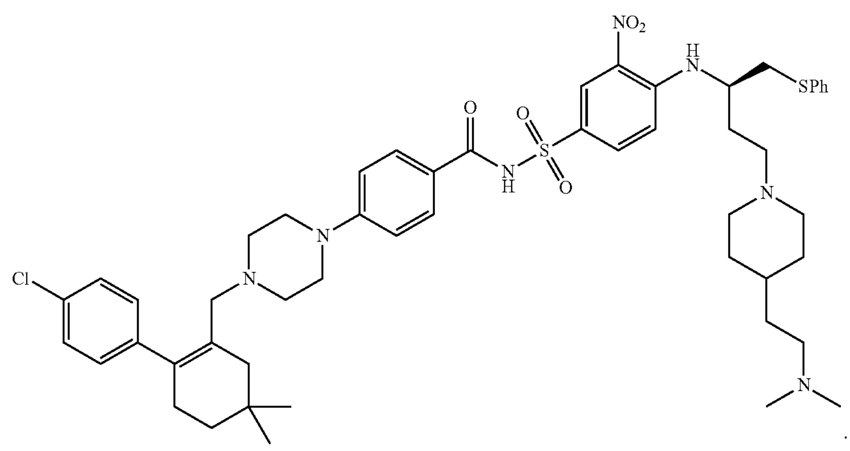
In some embodiments, the Bcl inhibitor is
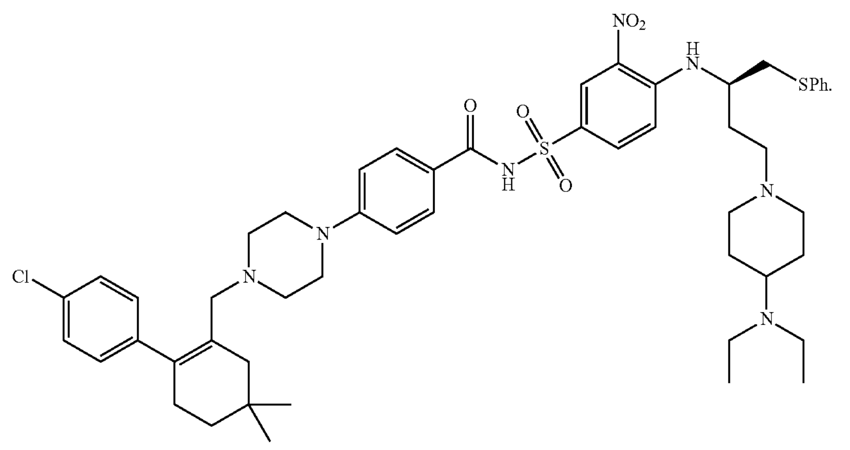

In some embodiments, the Bcl inhibitor is
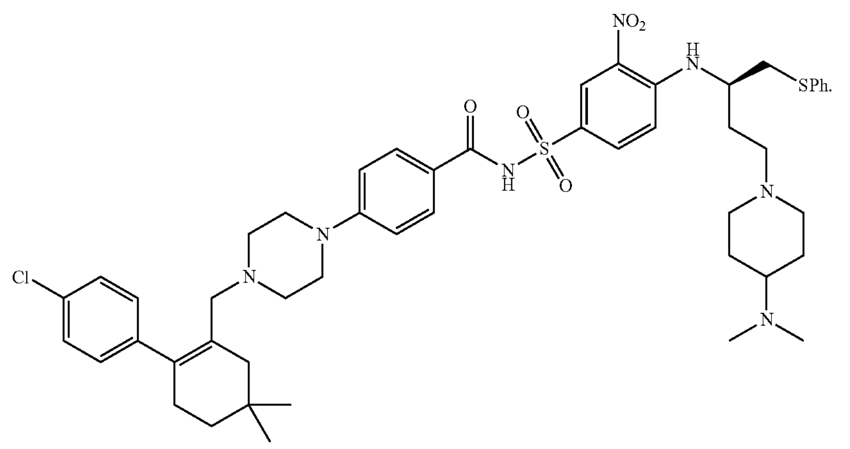
In some embodiments, the Bcl inhibitor is
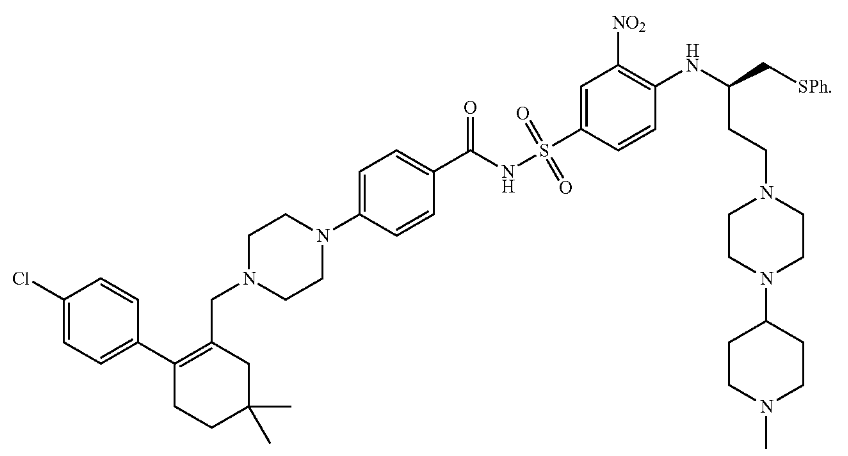
In some embodiments, the Bcl inhibitor is
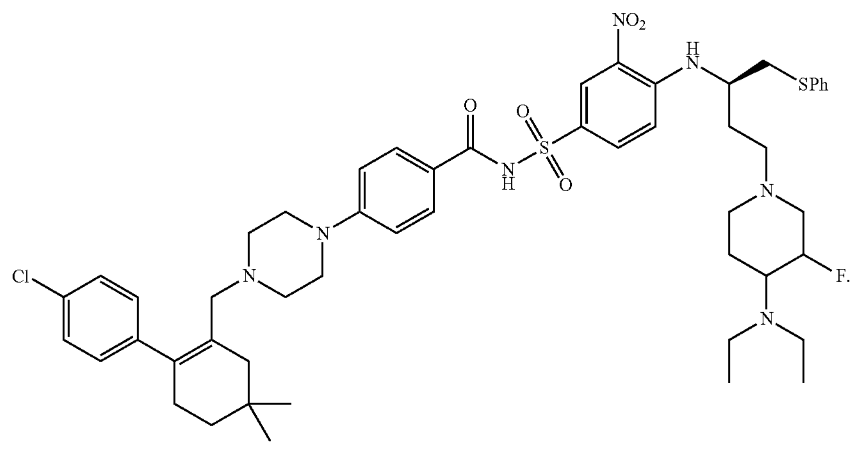

In some embodiments, the Bcl inhibitor is
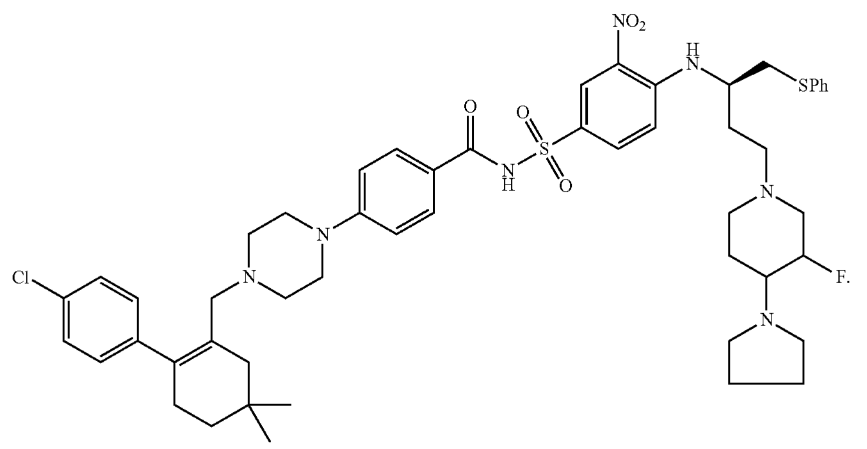
In some embodiments, the Bcl inhibitor is
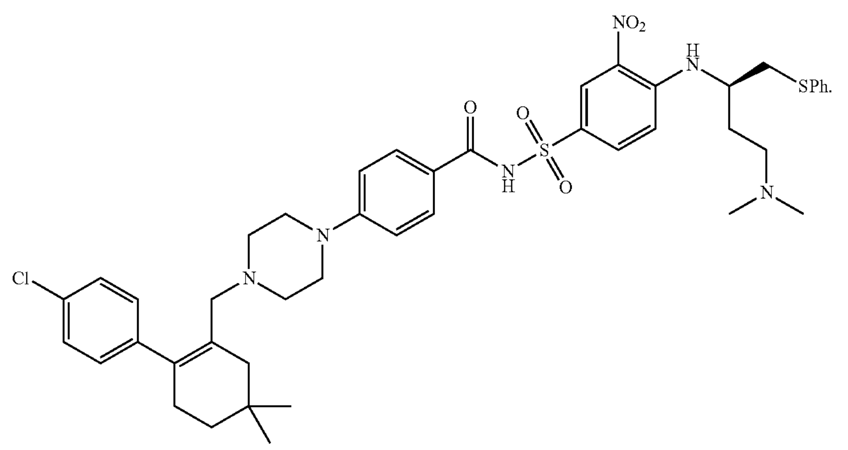
In some embodiments, the Bcl inhibitor is
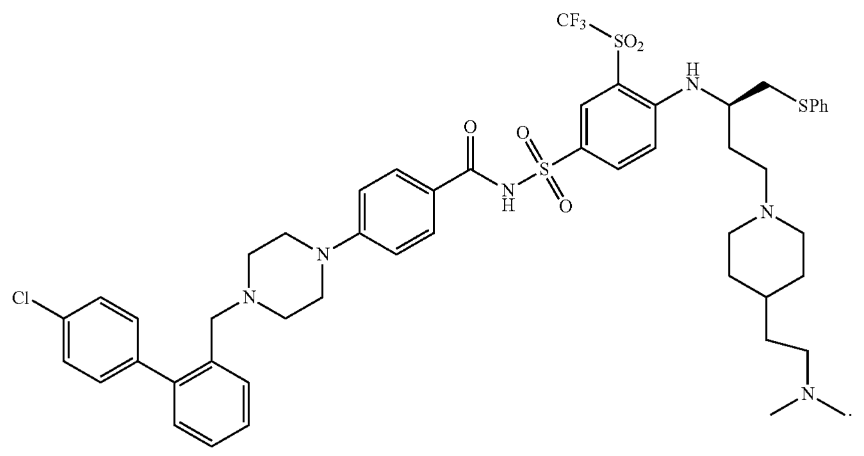

In some embodiments, the Bcl inhibitor is
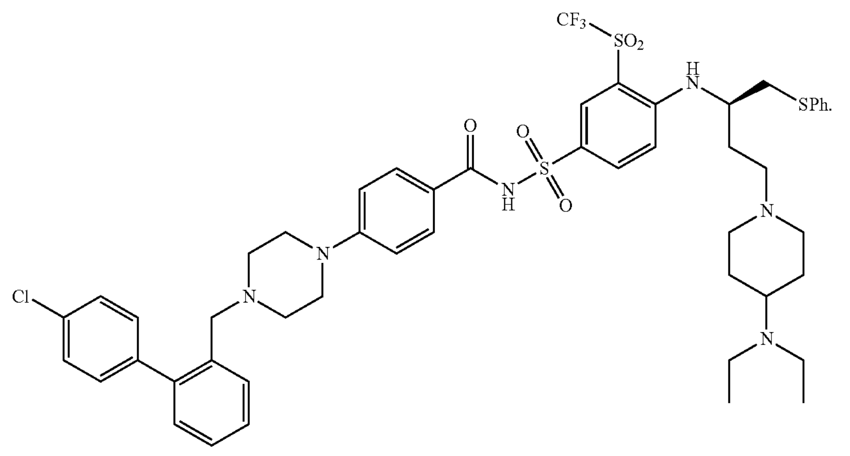
In some embodiments, the Bcl inhibitor is
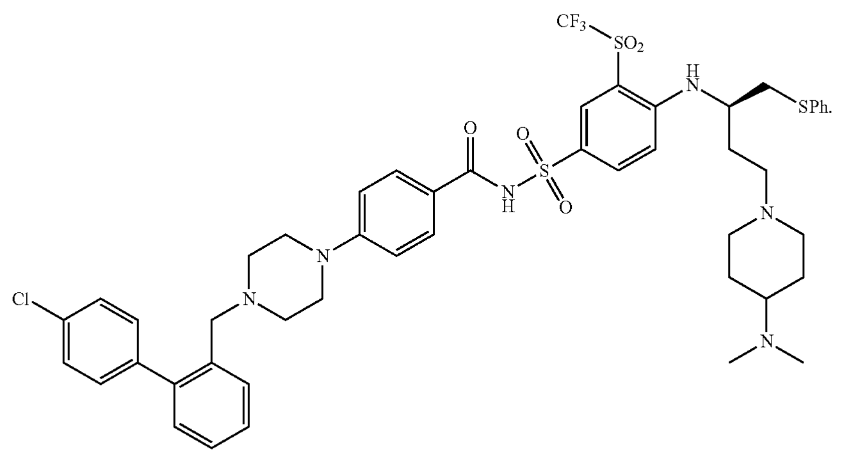
In some embodiments, the Bcl inhibitor is
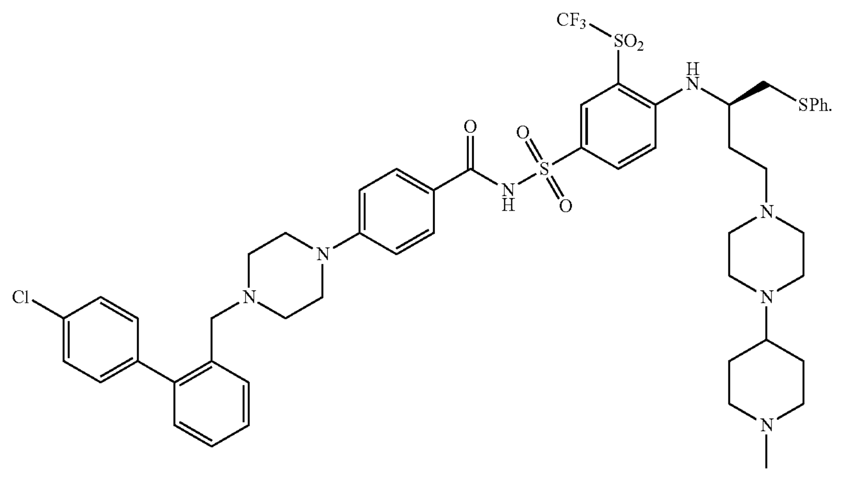

In some embodiments, the Bcl inhibitor is
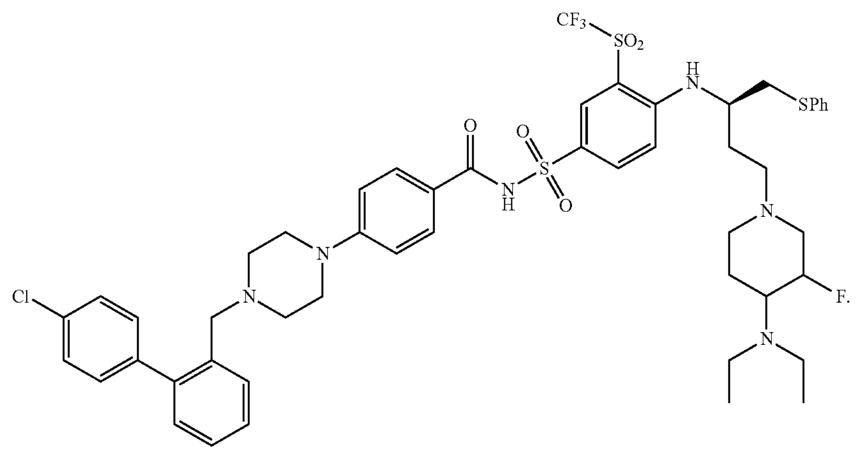
In some embodiments, the Bcl inhibitor is
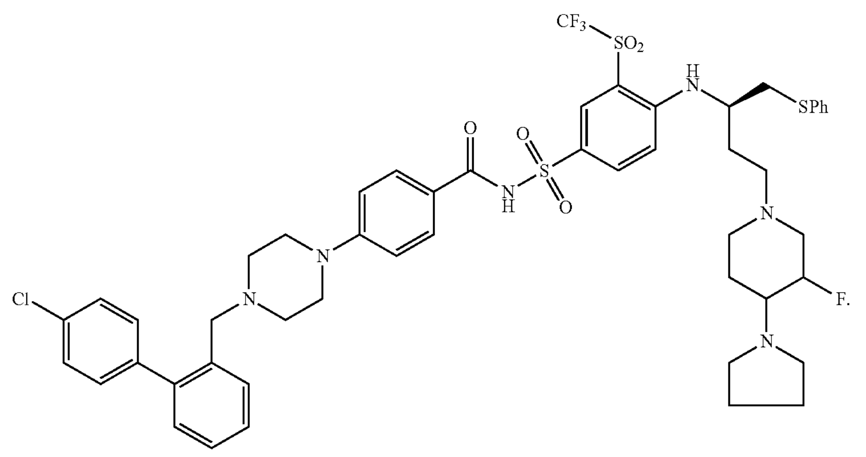
In some embodiments, the Bcl inhibitor is
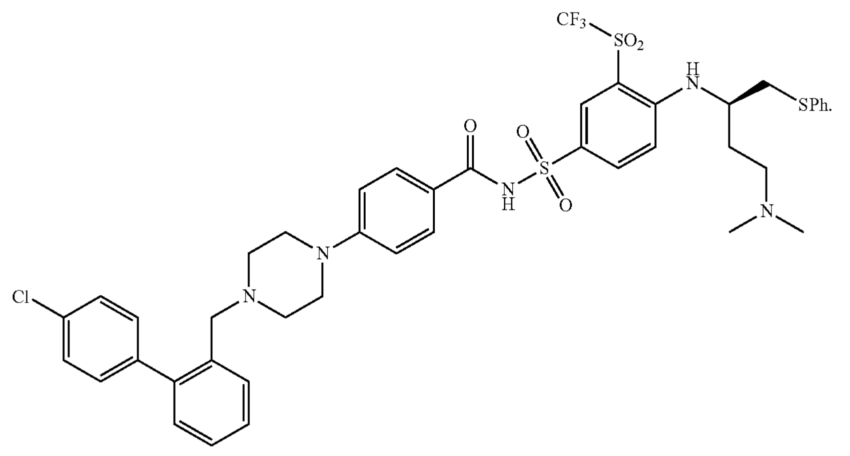
In some embodiments, the Bcl inhibitor is venetoclax. In some embodiments, the Bcl inhibitor is navitoclax.
In some embodiments, the liposomal compositions provided therein comprise a therapeutic agent. In some embodiments, the therapeutic agent is a hydrophobic therapeutic agent. In some embodiments, the therapeutic agent has a c Log P of greater than about 2. In some embodiments, the therapeutic agent has a c Log P between about 2 and about 12. In some embodiments, the therapeutic agent has a c Log P between about 3 and about 12. In some embodiments, the therapeutic agent has a c Log P between about 2 and about 4. In some embodiments, the therapeutic agent has a c Log P between about 2 and about 8. In some embodiments, the therapeutic agent has a c Log P between about 4 and about 12. In some embodiments, the therapeutic agent has a c Log P between about 4 and about 8. In some embodiments, the therapeutic agent has a c Log P between about 8 and about 12. In some embodiments, the therapeutic agent has a c Log P between about 10 and about 12.

In some embodiments, the therapeutic agent can be protonated and its protonated form has a $pK_a$ of greater than about 2. In some embodiments, the therapeutic agent can be protonated and its protonated form has a $pK_a$ between about 3 and about 11. In some embodiments, the therapeutic agent can be protonated and its protonated form has a $pK_a$ between about 6 and about 11. In some embodiments, the therapeutic agent can be protonated and its protonated form has a $pK_a$ between about 8 and about 11. In some embodiments, the therapeutic agent can be protonated and its protonated form has a $pK_a$ between about 3 and about 6. In some embodiments, the therapeutic agent can be protonated and its protonated form has a $pK_a$ between about 6 and about 8. In some embodiments, the therapeutic agent can be protonated and its protonated form has a $pK_a$ between about 3 and about 8. In some embodiments, the therapeutic agent can be protonated and its protonated form has a $pK_a$ between about 2 and about 12. In some embodiments, the therapeutic agent can be protonated and its protonated form has a $pK_a$ between about 2 and about 8. In some embodiments, the therapeutic agent can be protonated and its protonated form has a $pK_a$ between about 2 and about 4. In some embodiments, the therapeutic agent can be protonated and its protonated form has a $pK_a$ between about 4 and about 12. In some embodiments, the therapeutic agent can be protonated and its protonated form has a $pK_a$ between about 4 and about 8. In some embodiments, the therapeutic agent can be protonated and its protonated form has a $pK_a$ between about 8 and about 12. In some embodiments, the therapeutic agent can be protonated and its protonated form has a $pK_a$ between about 10 and about 12.

In some embodiments, the liposomal compositions provided therein comprise an additional therapeutic agent. In some embodiments, the additional therapeutic agent is a hydrophobic therapeutic agent. In some embodiments, the additional therapeutic agent is a hydrophilic therapeutic agent. In some embodiments, the additional therapeutic agent is encapsulated in the liposomes. In some embodiments, the additional therapeutic agent is external to the liposomes. In some embodiments of all the aforementioned aspects, the liposome further comprises an additional therapeutic agent. In some embodiments, the additional therapeutic agent is encapsulated in the liposome.

In some embodiments, the additional therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor.

In some embodiments, the additional therapeutic agent is an HSP90 inhibitor. In some embodiments, the HSP90 inhibitor is Luminespib.

In some embodiments, the additional therapeutic agent is an alkylating agent. In some embodiments, the additional therapeutic agent is an alkylating agent selected from the group consisting of Bendamustine and Chlorambucil.

In some embodiments, the additional therapeutic agent is an antitubulin agent. In some embodiments, the additional therapeutic agent is an antitubulin agent selected from the group consisting of Vincristine, Vinorelbine, and docetaxel.

In some embodiments, the additional therapeutic agent is an ATR inhibitor.

In some embodiments, the additional therapeutic agent is a RAF inhibitor. In some embodiments, the RAF inhibitor is Dabrafenib. In some embodiments, the additional therapeutic agent is a BRAF inhibitor. In some embodiments, the BRAF inhibitor is Vemurafenib.

In some embodiments, the additional therapeutic agent is a BTK inhibitor. In some embodiments, the BTK inhibitor is Ibrutinib.

In some embodiments, the additional therapeutic agent is an HDAC inhibitor. In some embodiments, the HDAC inhibitor is Panobinostat.

In some embodiments, the additional therapeutic agent is a JAK inhibitor. In some embodiments, the JAK inhibitor is Ruxolitinib.

In some embodiments, the additional therapeutic agent is an MEK inhibitor. In some embodiments, the additional therapeutic agent is an MEK inhibitor selected from the group consisting of Selumetinib and Cobimetinib.

In some embodiments, the additional therapeutic agent is a PARP inhibitor. In some embodiments, the additional therapeutic agent is a PARP inhibitor selected from the group consisting of Talazoparib, Niraparib, and Rucaparib.

In some embodiments, the additional therapeutic agent is a PI3K inhibitor. In some embodiments, the PI3K inhibitor is Idelalisib.

In some embodiments, the additional therapeutic agent is a proteasome inhibitor. In some embodiments, the proteasome inhibitor is Carfilzomib.

In some embodiments, the additional therapeutic agent is an SMO inhibitor. In some embodiments, the additional therapeutic agent is an SMO inhibitor selected from the group consisting of Sonidegib and Vismodegib.

In some embodiments, the additional therapeutic agent is a tyrosine kinase inhibitor. In some embodiments, the additional therapeutic agent is a tyrosine kinase inhibitor selected from the group consisting of Brigatinib, Lenvatinib, Afatinib, Axitinib, Cabozantinib, Ponatinib, Sorafenib, Osimertinib, Regorafenib, Bosutinib, Crizotinib, Vandetanib, Nilotinib, Alectinib, Ceritinib, Dasatinib, Pazopanib, Sunitinib, Erlotinib, Imatinib, Gefitinib, Lapatinib.

In some embodiments, the additional therapeutic agent is a topoisomerase inhibitor. In some embodiments, the additional therapeutic agent is a topoisomerase I inhibitor. In some embodiments, the topoisomerase inhibitor is Irinotecan.

In some embodiments, the additional therapeutic agent is a Bcl inhibitor such as those described above.

Liposomes and Liposomal Compositions

Liposomes comprise one or more lipid bilayers enclosing an internal compartment. These liposomes can be multilamellar, bilamellar, or unilamellar vesicles. Unilamellar liposomes (also known as unilamellar vesicles or "ULV") enclose a single internal aqueous compartment and are classified as either small unilamellar vesicles (SUV) or large unilamellar vesicles (LUV). LUV and SUV range in size from about 50 to 500 nm and 20 to 50 nm, respectively. Bilamellar liposomes have two lipid membranes wherein the inner membrane surrounds a single internal aqueous compartment and the second, larger outer membrane surrounds the inner membrane thus creating a second internal aqueous compartment.

In some embodiments, liposomes have a mean diameter between about 20 nm and about 500 nm. In some embodiments, liposomes have a mean diameter between about 50 nm and about 250 nm. In some embodiments, liposomes have a mean diameter between about 80 nm and about 250 nm. In some embodiments, liposomes have a mean diameter between about 50 nm and about 150 nm. In some embodiments, liposomes have a mean diameter between about 80 nm and about 150 nm. In some embodiments, liposomes have a mean diameter between about 50 nm and about 120 nm. In some embodiments, liposomes have a mean diameter between about 80 nm and about 120 nm. In some embodiments, liposomes have a mean diameter of about 50 nm, about 80 nm, about 100 nm, about 120 nm, about 150 nm, or about 250 nm. In some embodiments, liposomes have a mean diameter of about 80 nm.

Maintaining the size distribution of the liposomes in the liposomal composition may be assessed experimentally by obtaining particle size profiles. Size distribution determined by quasielastic light scattering is typically presented as a histogram showing the mean diameter of the liposomes. Significant size distribution measurements most commonly used in the art are D10, D90, D99 or a standard deviation or polydispersity index (PDI). "D99" values signify that 99% of the liposomes are less than a referenced size or more than a referenced size. This is particularly useful if, for example, it is important to exclude either an upper or lower size. For example, in certain embodiments it is desirable to ensure that no liposomes over 200 nm in mean diameter are present.

In some embodiments, the size distribution of the liposomes in the liposomal composition is quantified using the polydispersity index (PDI). In some embodiments, the liposomal composition has a polydispersity index (PDI) between about 0.001 and about 0.5. In some embodiments, the liposomal composition has a polydispersity index (PDI) between about 0.001 and about 0.4. In some embodiments, the liposomal composition has a polydispersity index (PDI) between about 0.001 and about 0.3. In some embodiments, the liposomal composition has a polydispersity index (PDI) between about 0.005 and about 0.5. In some embodiments, the liposomal composition has a polydispersity index (PDI) between about 0.005 and about 0.4. In some embodiments, the liposomal composition has a polydispersity index (PDI) between about 0.005 and about 0.3. In some embodiments, the liposomal composition has a polydispersity index (PDI) between about 0.001 and about 0.2. In some embodiments, the liposomal composition has a polydispersity index (PDI) between about 0.001 and about 0.1. In some embodiments, the liposomal composition has a polydispersity index (PDI) between about 0.005 and about 0.2. In some embodiments, the liposomal composition has a polydispersity index (PDI) between about 0.005 and about 0.1. In some embodiments, the liposomal composition has a polydispersity index (PDI) between about 0.01 and about 0.5. In some embodiments, the liposomal composition has a polydispersity index (PDI) between about 0.01 and about 0.4. In some embodiments, the liposomal composition has a polydispersity index (PDI) between about 0.01 and about 0.2. In some embodiments, the liposomal composition has a polydispersity index (PDI) between about 0.01 and about 0.1. In some embodiments, the liposomal composition has a polydispersity index (PDI) between about 0.1 and about 0.5. In some embodiments, the liposomal composition has a polydispersity index (PDI) between about 0.1 and about 0.3. In some embodiments, the liposomal composition has a polydispersity index (PDI) between about 0.3 and about 0.5.

In some embodiments, the liposomal compositions may further comprise a carrier medium. In some embodiments, the one or more liposomes are suspended in a carrier medium. In some embodiments, the carrier medium is a pharmaceutically acceptable solution. In some embodiments, the carrier medium is an aqueous dextrose solution. In some embodiments, the carrier medium is an aqueous sucrose solution. In some embodiments, the carrier medium is a saline solution. In some embodiments, the carrier medium further comprises a buffer. In some embodiments, the buffer is a HEPES buffer. In some embodiments, the buffer is a PBS buffer. In some embodiments, the buffer is a Tris buffer. In some embodiments, the buffer is a MES buffer.

Therapeutic Agents

In some embodiments, the liposomes and liposomal compositions provided therein comprise a therapeutic agent encapsulated in the liposomes. In some embodiments, the liposomes and liposomal compositions provided therein comprise a hydrophobic therapeutic agent encapsulated in the liposomes.

In some embodiments, the therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor.

In some embodiments, the therapeutic agent is an HSP90 inhibitor. In some embodiments, the HSP90 inhibitor is Luminespib.

In some embodiments, the therapeutic agent is an alkylating agent. In some embodiments, the therapeutic agent is an alkylating agent selected from the group consisting of Bendamustine and Chlorambucil.

In some embodiments, the therapeutic agent is an antitubulin agent. In some embodiments, the therapeutic agent is an antitubulin agent selected from the group consisting of Vincristine, Vinorelbine, and docetaxel.

In some embodiments, the therapeutic agent is an ATR inhibitor.

In some embodiments, the therapeutic agent is a RAF inhibitor. In some embodiments, the RAF inhibitor is Dabrafenib. In some embodiments, the therapeutic agent is a BRAF inhibitor. In some embodiments, the BRAF inhibitor is Vemurafenib.

In some embodiments, the therapeutic agent is a BTK inhibitor. In some embodiments, the BTK inhibitor is Ibrutinib.

In some embodiments, the therapeutic agent is an HDAC inhibitor. In some embodiments, the HDAC inhibitor is Panobinostat.

In some embodiments, the therapeutic agent is a JAK inhibitor. In some embodiments, the JAK inhibitor is Ruxolitinib.

In some embodiments, the therapeutic agent is an MEK inhibitor. In some embodiments, the therapeutic agent is an MEK inhibitor selected from the group consisting of Selumetinib and Cobimetinib.

In some embodiments, the therapeutic agent is a PARP inhibitor. In some embodiments, the therapeutic agent is a PARP inhibitor selected from the group consisting of Talazoparib, Niraparib, and Rucaparib.

In some embodiments, the therapeutic agent is a PI3K inhibitor. In some embodiments, the PI3K inhibitor is Idelalisib.

In some embodiments, the therapeutic agent is a proteasome inhibitor. In some embodiments, the proteasome inhibitor is Carfilzomib.

In some embodiments, the therapeutic agent is an SMO inhibitor. In some embodiments, the therapeutic agent is an SMO inhibitor selected from the group consisting of Sonidegib and Vismodegib.

In some embodiments, the therapeutic agent is a tyrosine kinase inhibitor. In some embodiments, the therapeutic agent is a tyrosine kinase inhibitor selected from the group consisting of Brigatinib, Lenvatinib, Afatinib, Axitinib, Cabozantinib, Ponatinib, Sorafenib, Osimertinib, Regorafenib, Bosutinib, Crizotinib, Vandetanib, Nilotinib, Alectinib, Ceritinib, Dasatinib, Pazopanib, Sunitinib, Erlotinib, Imatinib, Gefitinib, Lapatinib.

In some embodiments, the therapeutic agent is a topoisomerase inhibitor. In some embodiments, the therapeutic agent is a topoisomerase I inhibitor. In some embodiments, the topoisomerase inhibitor is Irinotecan.

In some embodiments, the therapeutic agent is a Bcl inhibitor. In some embodiments, the Bcl inhibitor is a Bcl-2 inhibitor. In some embodiments, the Bcl inhibitor is a Bcl-$X_L$ inhibitor. In some embodiments, the Bcl inhibitor is a Bcl-2/Bcl-$X_L$ dual inhibitor. In some embodiments, the Bcl inhibitor is a compound of Formula (I):

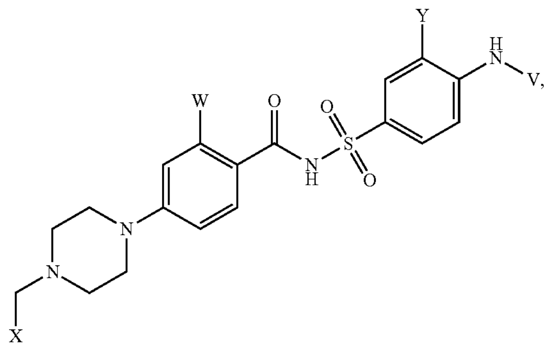

or a stereoisomer, tautomer, or pharmaceutically acceptable salt thereof, wherein:

V is

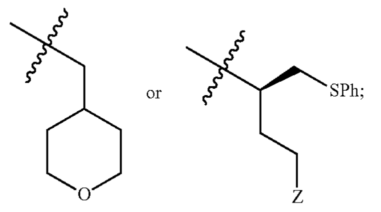

W is H or

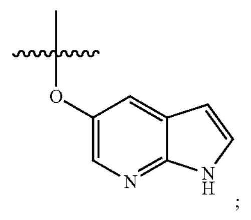 [SMILES: *Oc1cnc2[nH]ccc2c1]

X is

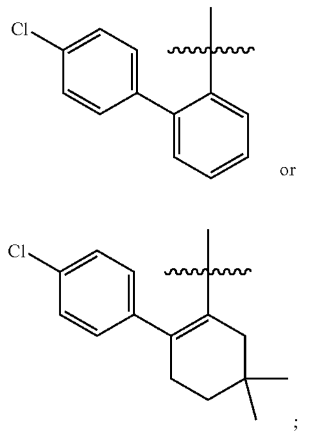 [SMILES: *c1ccccc1-c1ccc(Cl)cc1 ; *C1=C(c2ccc(Cl)cc2)CCC(C)(C)C1]

Y is —$NO_2$ or —$SO_2CF_3$;

Z is selected from the group consisting of

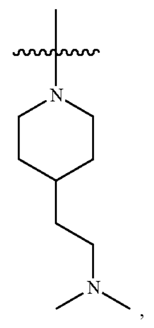

-continued
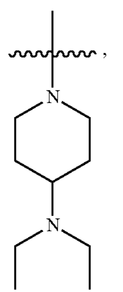
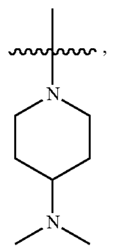
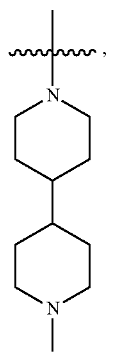
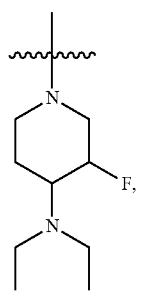
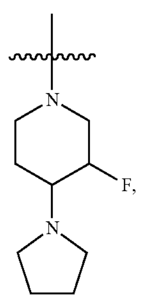
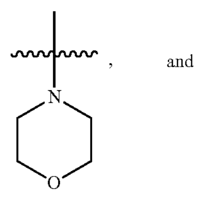
and
-continued
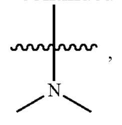
In some embodiments, V is
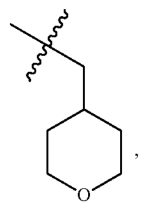 [SMILES: *CC1CCOCC1]
In some embodiments, V is
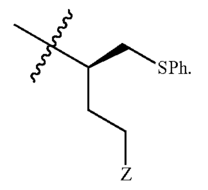
In some embodiments, W is H. In some embodiments, W is
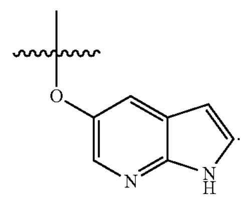 [SMILES: *Oc1cnc2[nH]ccc2c1]
In some embodiments, X is
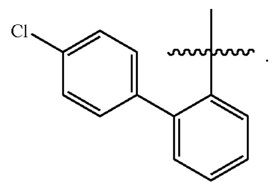 [SMILES: *c1ccccc1-c1ccc(Cl)cc1]
In some embodiments, X is
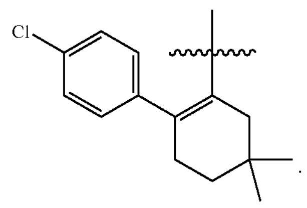 [SMILES: *C1=C(c2ccc(Cl)cc2)CCC(C)(C)C1]
In some embodiments, Y is $-NO_2$. In some embodiments, Y is $-SO_2CF_3$. In some embodiments, Z is

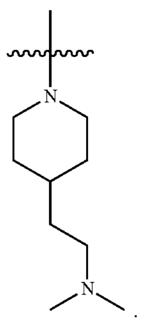 [SMILES: *N1CCC(CCN(C)C)CC1]
In some embodiments, Z is
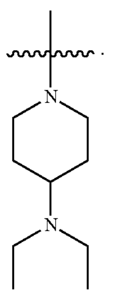 [SMILES: *N1CCC(N(CC)CC)CC1]
In some embodiments, Z is
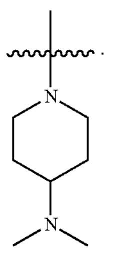 [SMILES: *N1CCC(N(C)C)CC1]
In some embodiments, Z is
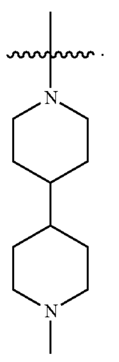 [SMILES: *N1CCC(C2CCN(C)CC2)CC1]
In some embodiments, Z is
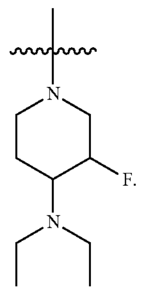 [SMILES: *N1CCC(N(CC)CC)C(F)C1]
In some embodiments, Z is
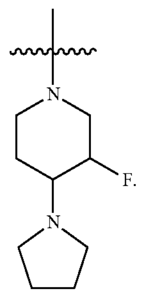 [SMILES: *N1CCC(N2CCCC2)C(F)C1]
In some embodiments, Z is
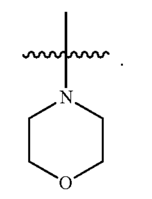
In some embodiments, Z is
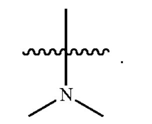
In some embodiments, the Bcl inhibitor is selected from the group consisting of Compound 1
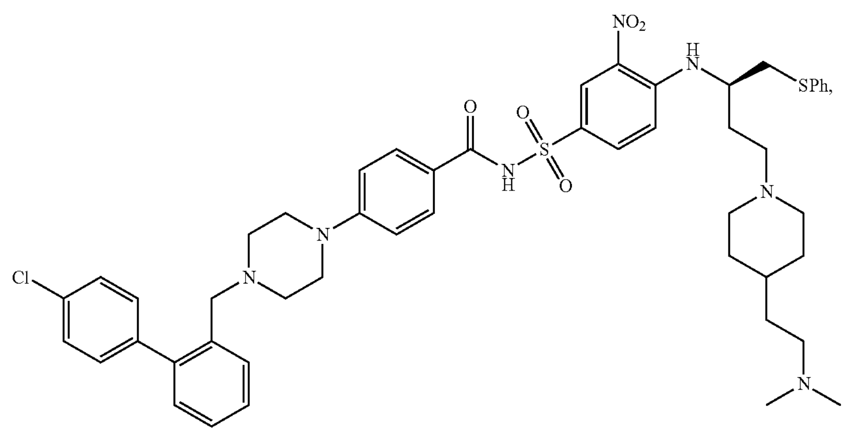
Compound 2
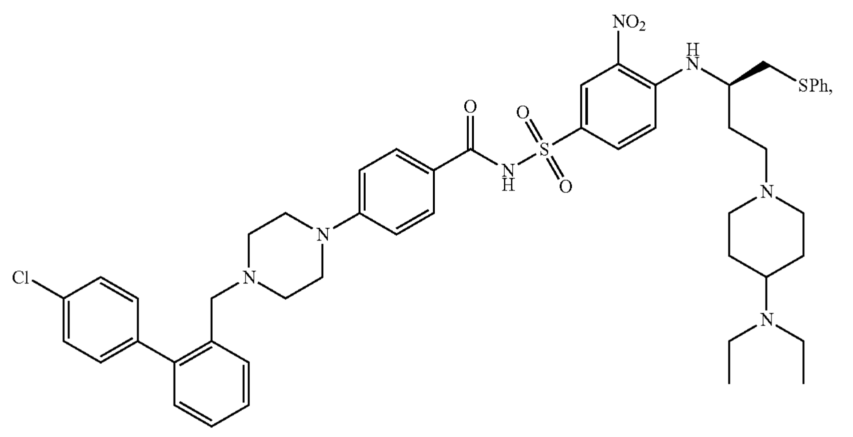
Compound 3
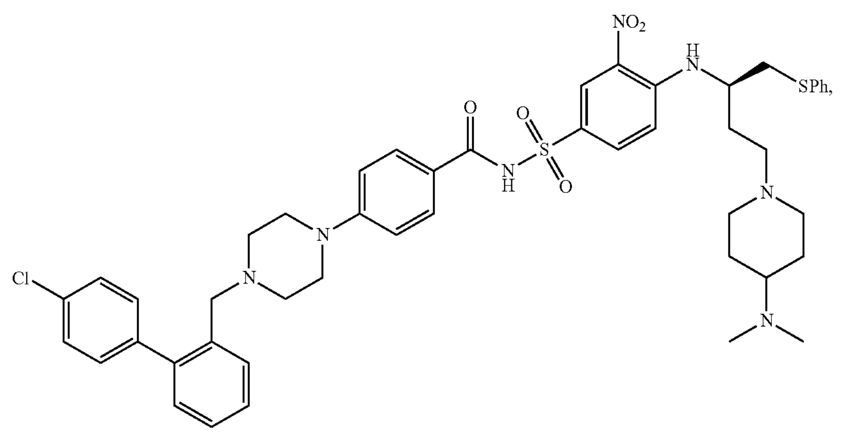

-continued
Compound 4
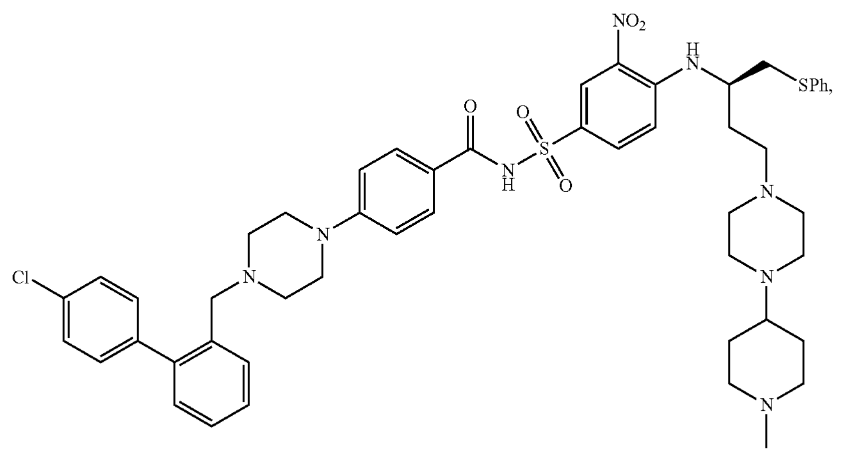
Compound 5
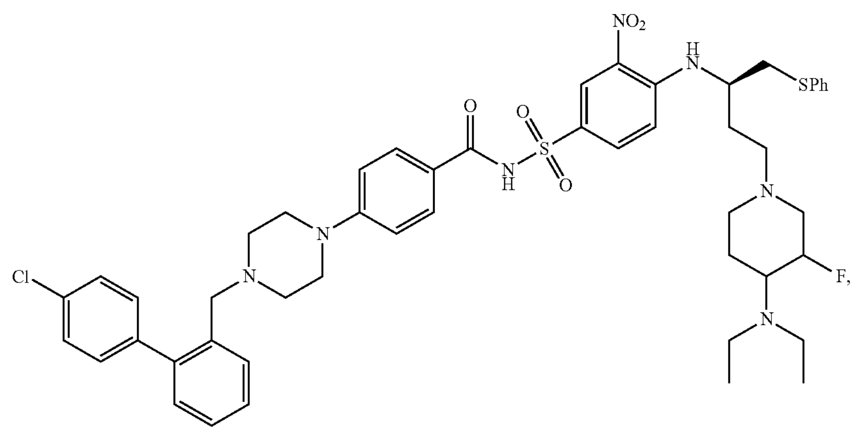
Compound 6
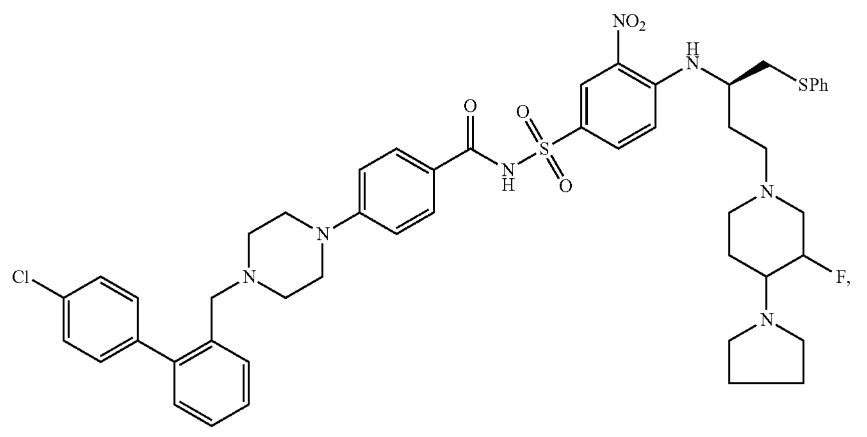

-continued
Compound 7
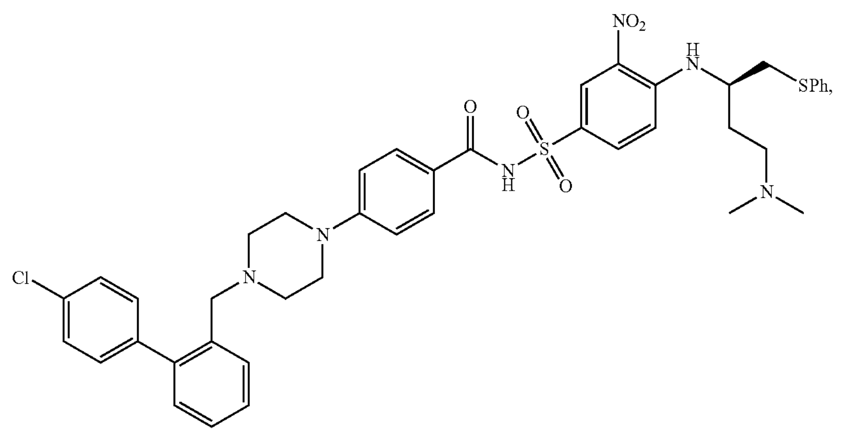
Compound 8
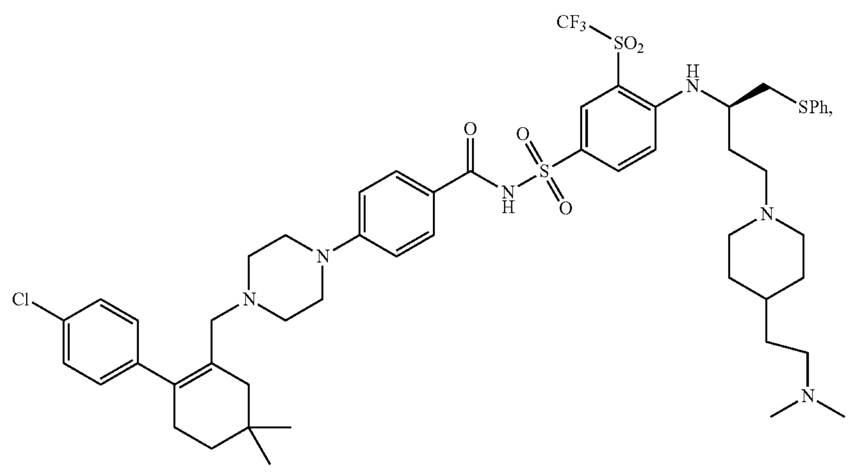
Compound 9
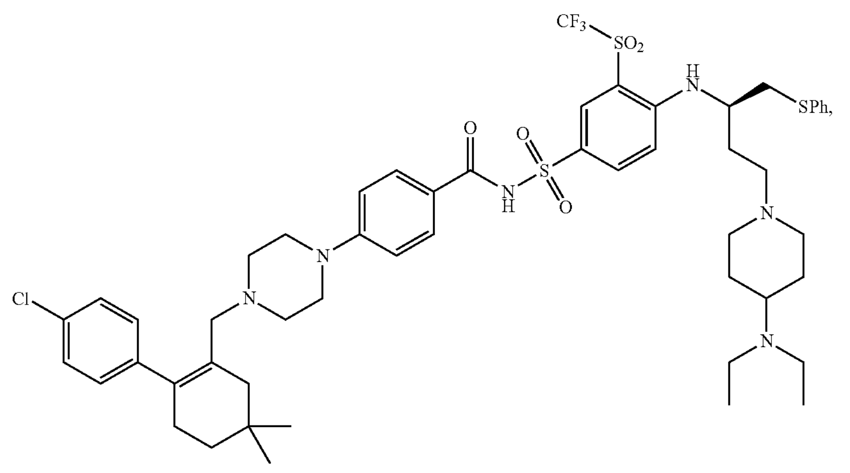

-continued
Compound 10
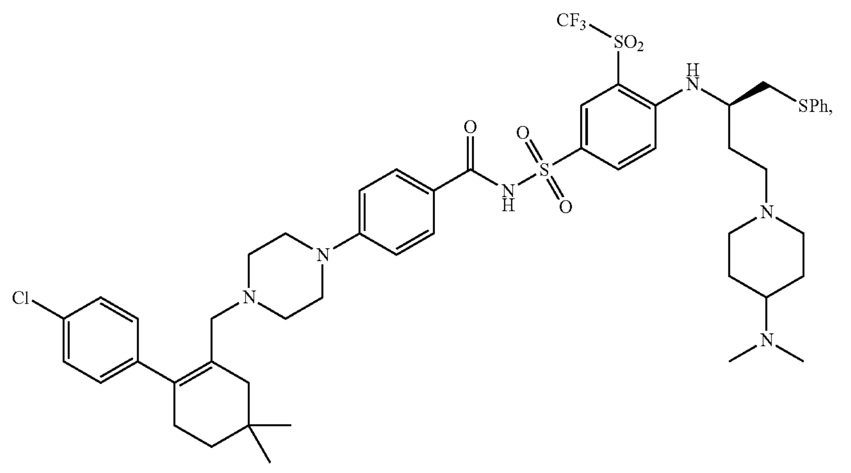
Compound 11
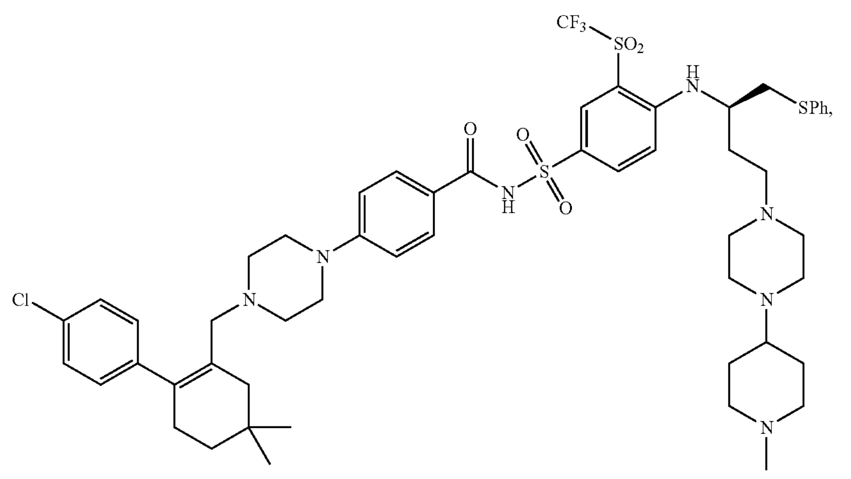
Compound 12
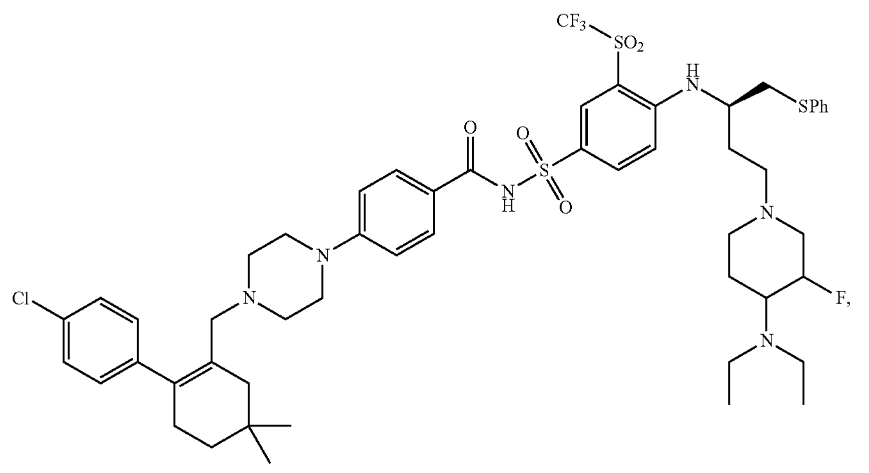

-continued
Compound 13
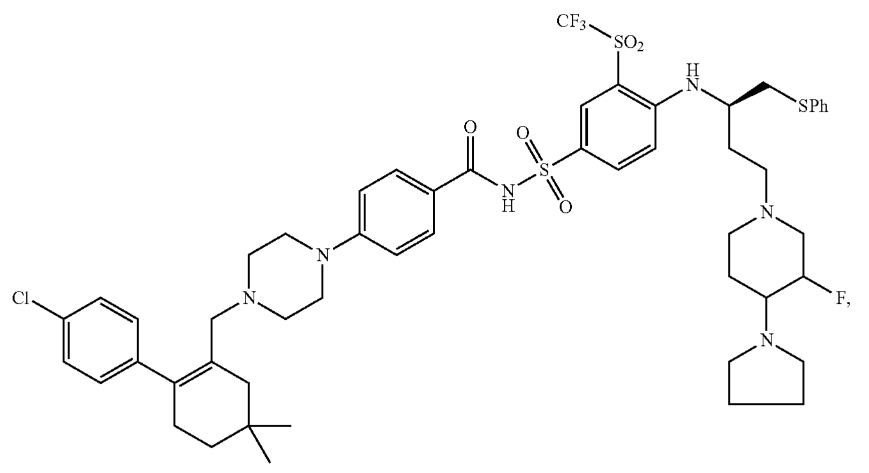
Compound 14
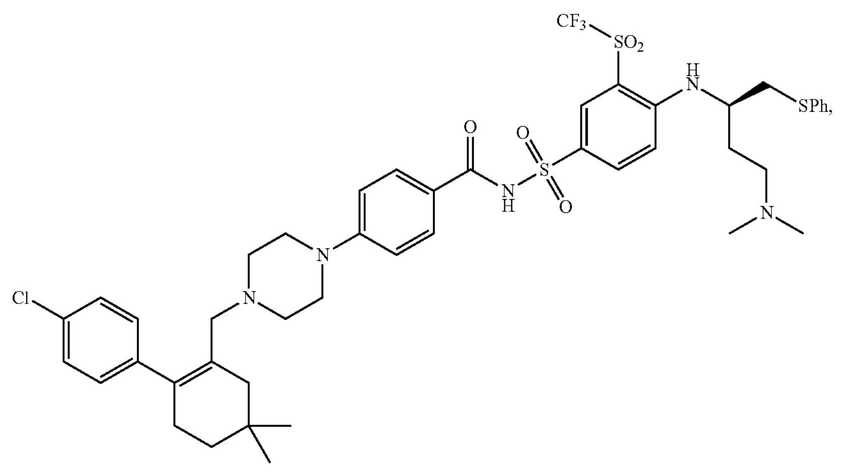
Compound 15
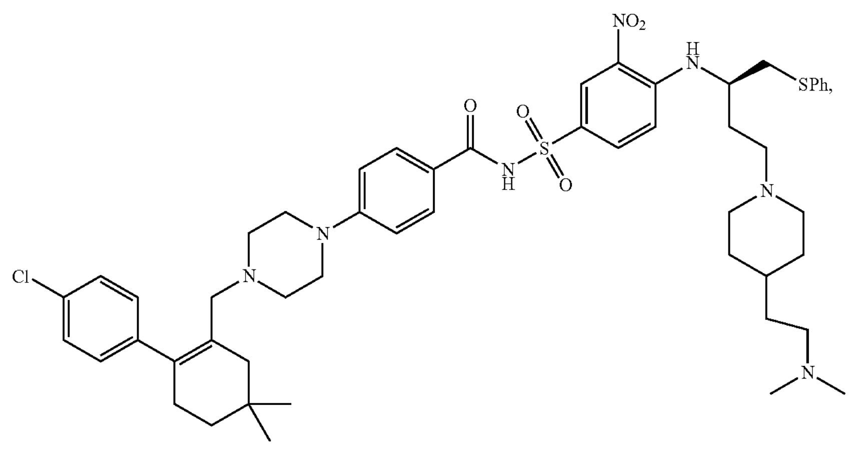

-continued
Compound 16
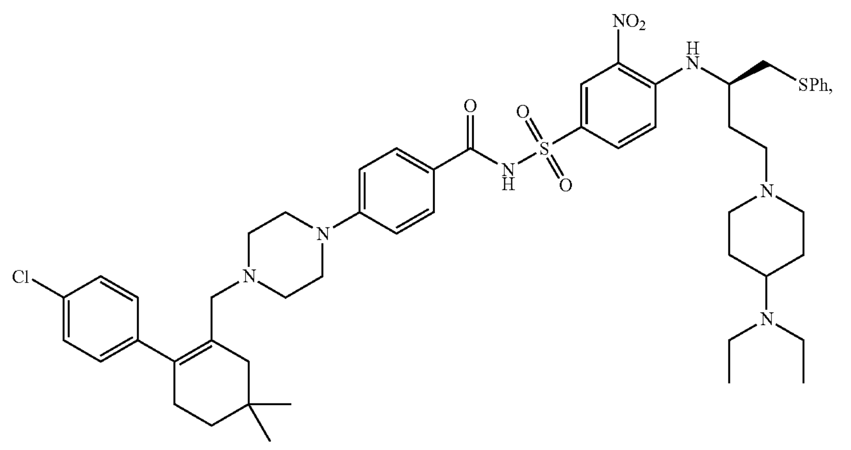
Compound 17
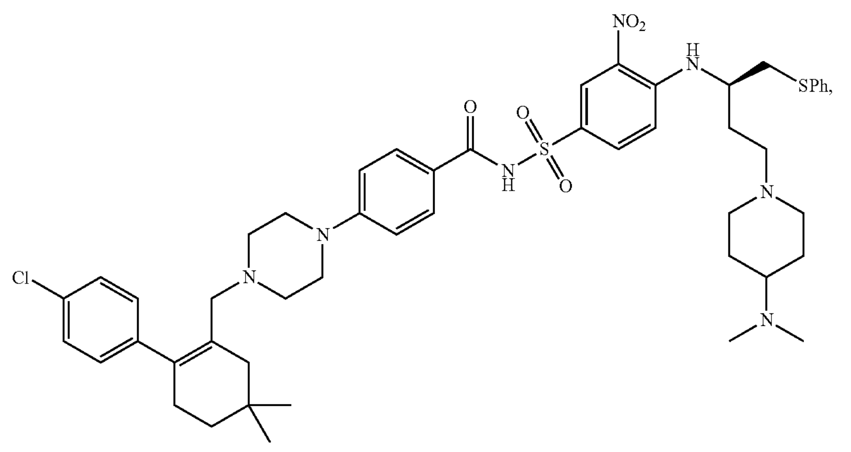
Compound 18
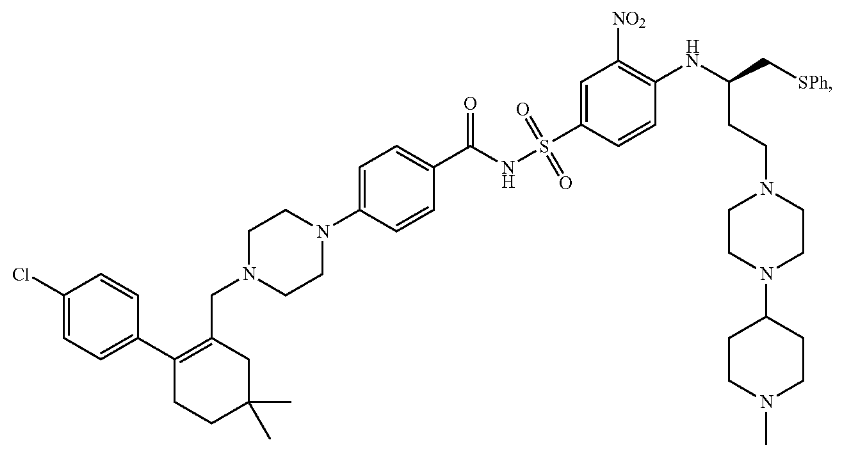

-continued
Compound 19
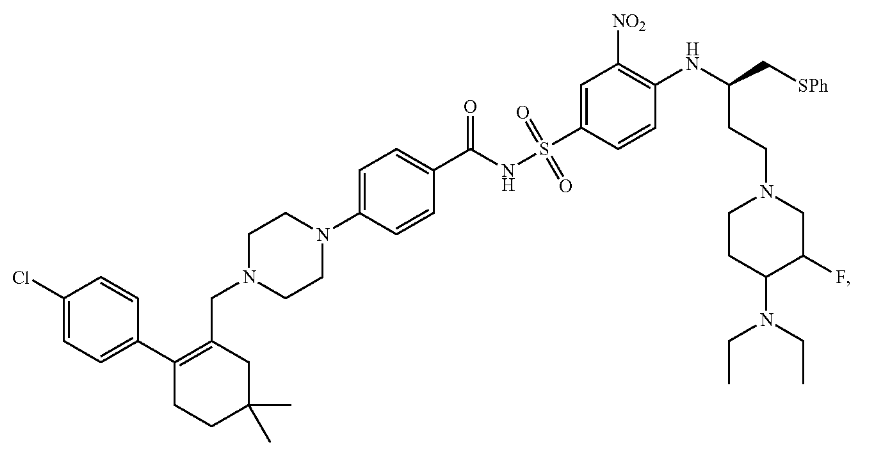
Compound 20
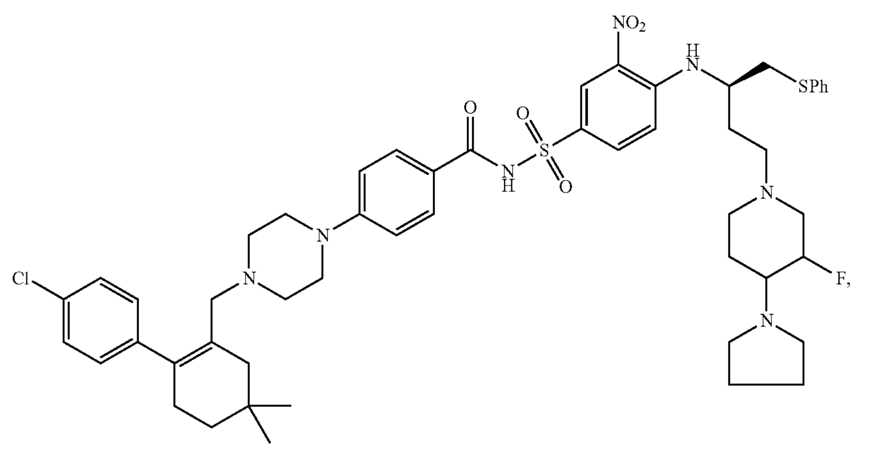
Compound 21
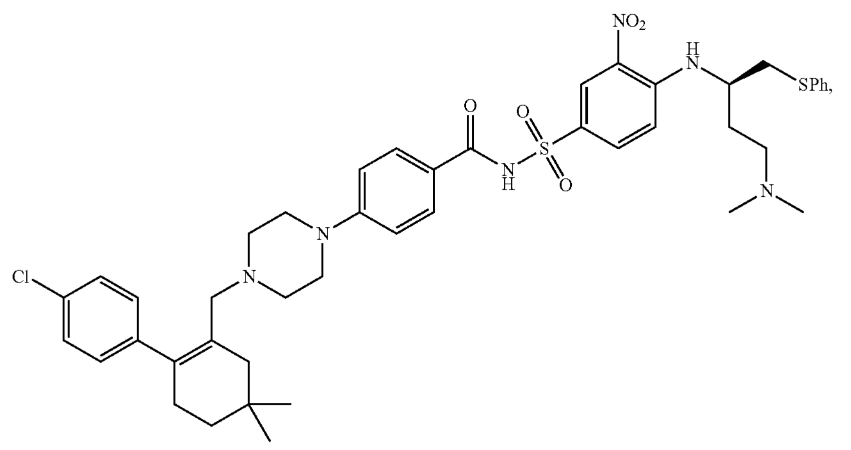

-continued
Compound 22
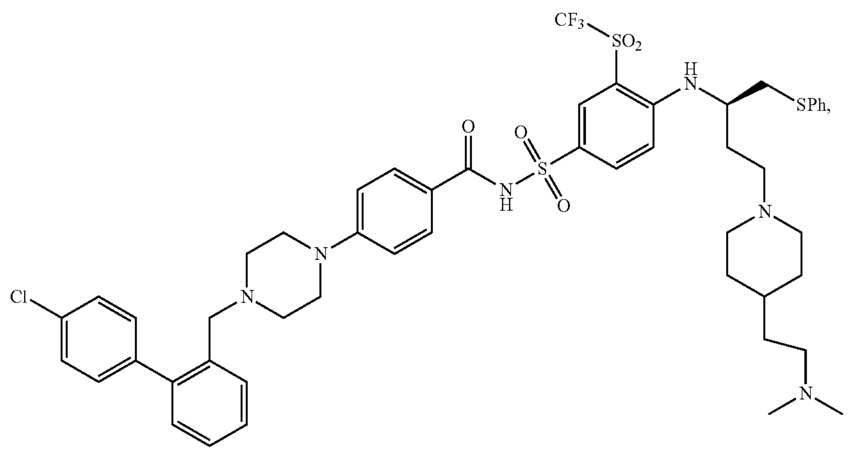
Compound 23
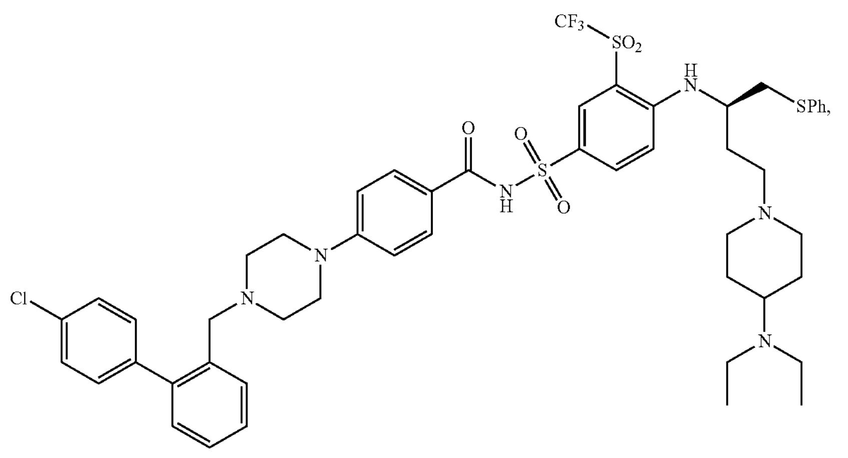
Compound 24
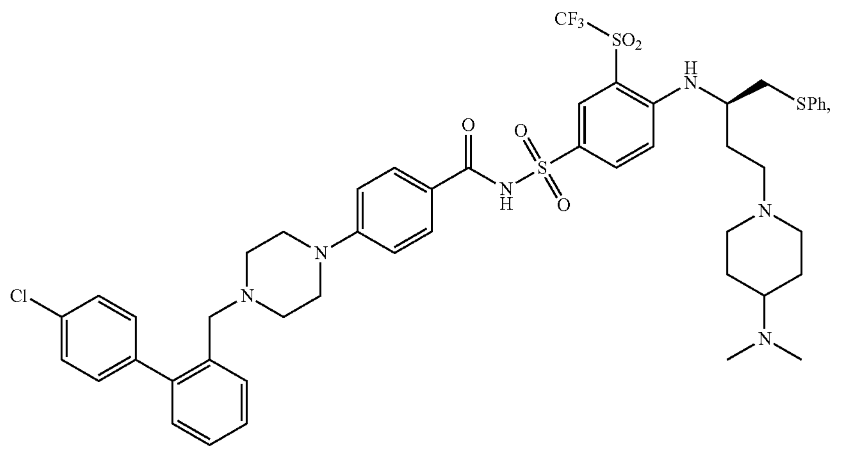

-continued
Compound 25
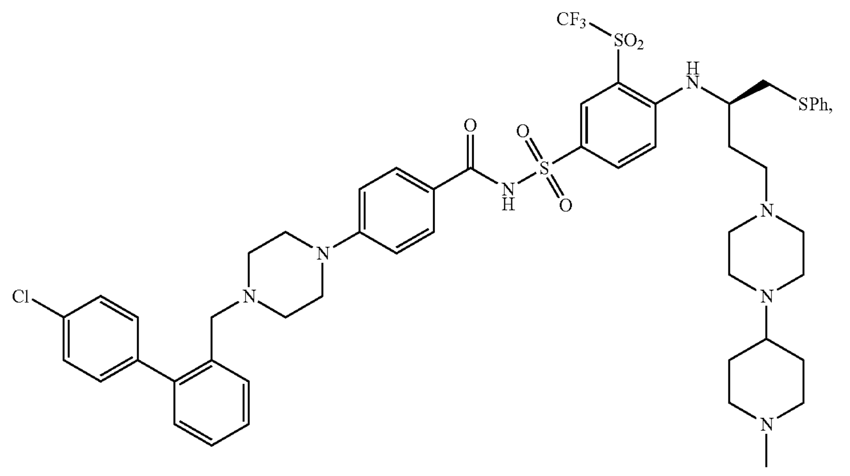
Compound 26
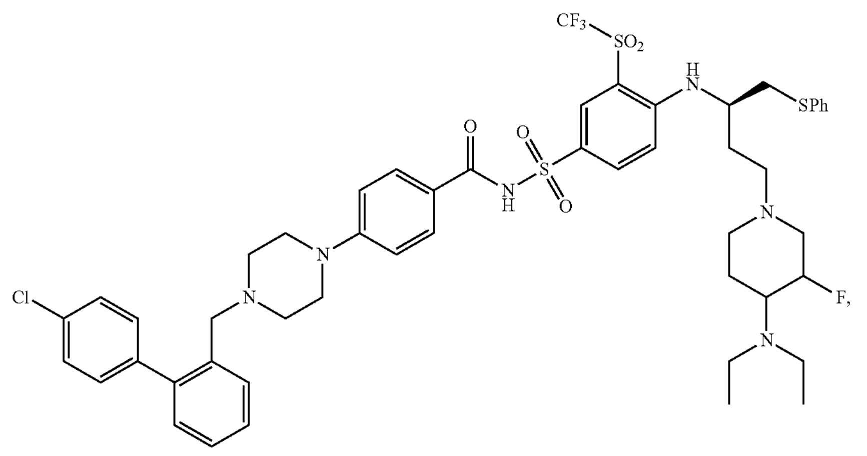
Compound 27
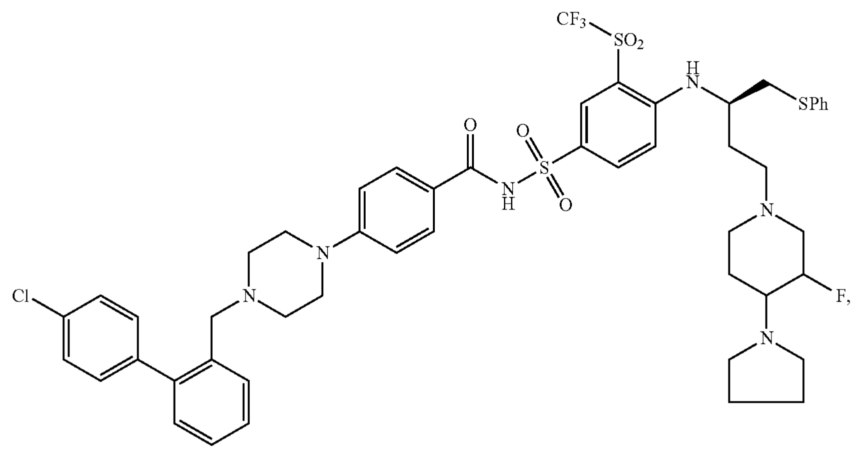

-continued
Compound 28
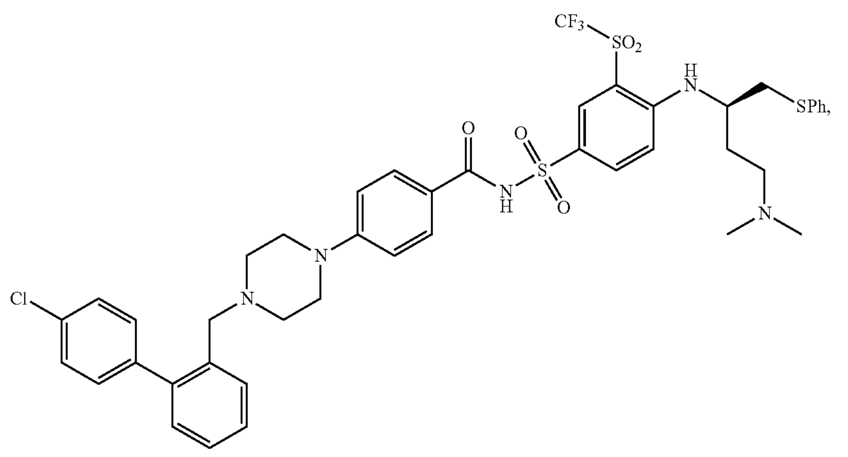
venetoclax (ABT-199), navitoclax (ABT-263), ABT-737, obatoclax mesylate (GX15-070), sabutoclax, TW-37, (R)-(−)-gossypol acetic acid, HA14-1, a 1B1H3-mimetic, and oblimersen. In some embodiments, the Bcl inhibitor is selected from the group consisting of
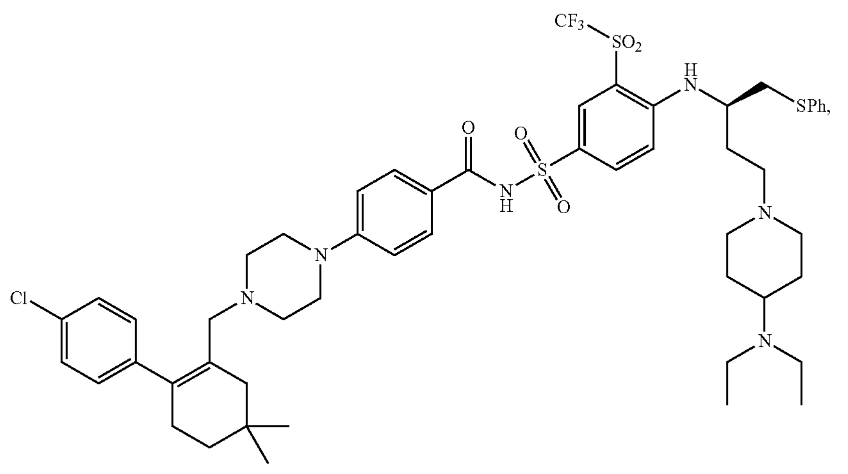
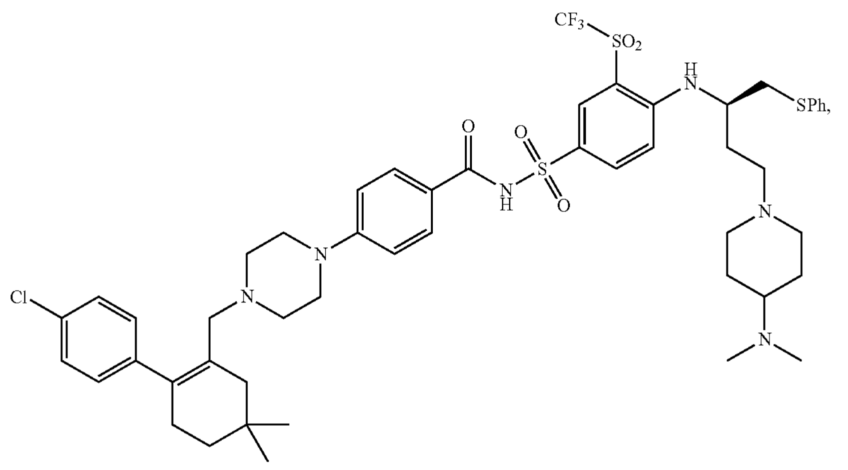

-continued
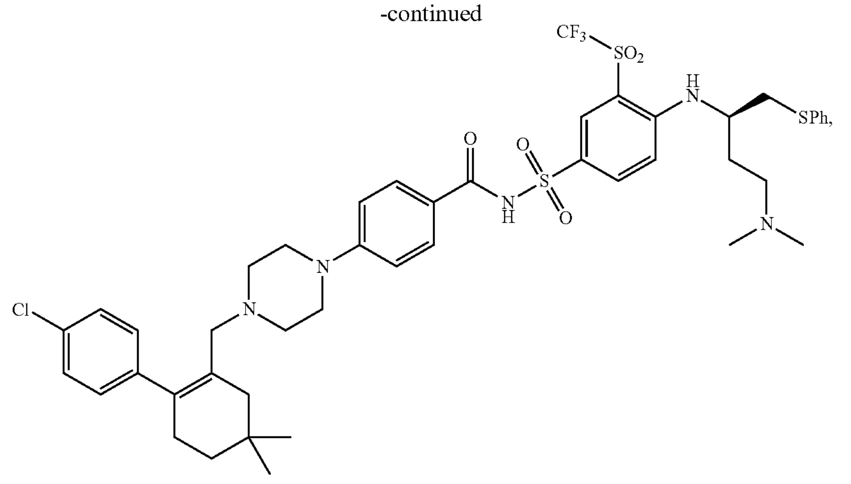
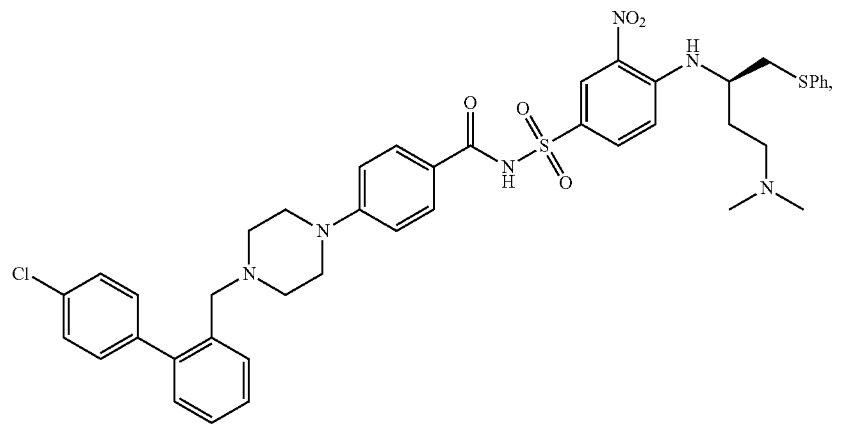
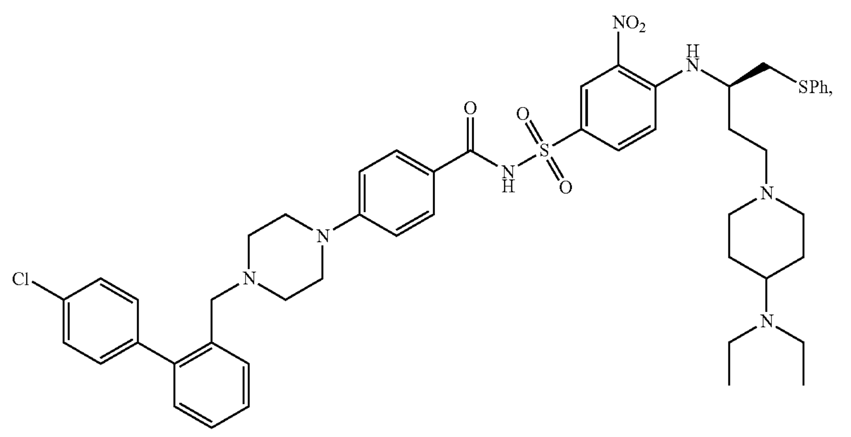
venetoclax (ABT-199), navitoclax (ABT-263), obatoclax mesylate (GX15-070), sabutoclax, TW-37, (R)-(−)-gossypol acetic acid, HA14-1, a BH3-mimetic, and oblimersen. In some embodiments, the Bcl inhibitor is selected from the group consisting of

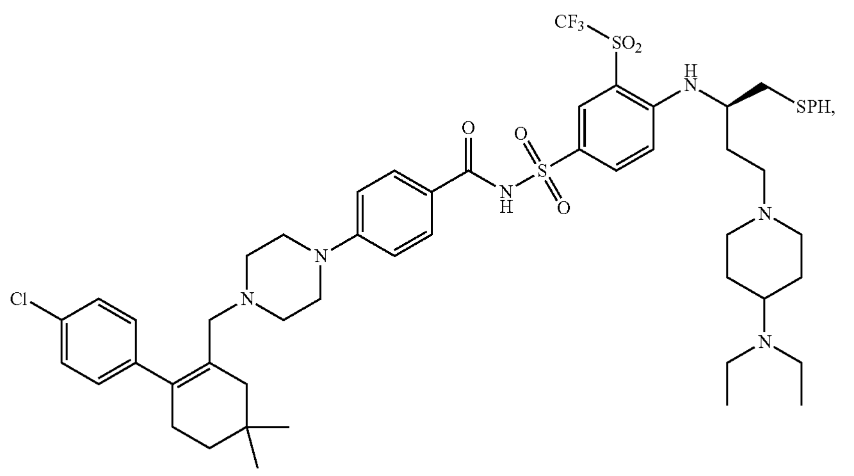
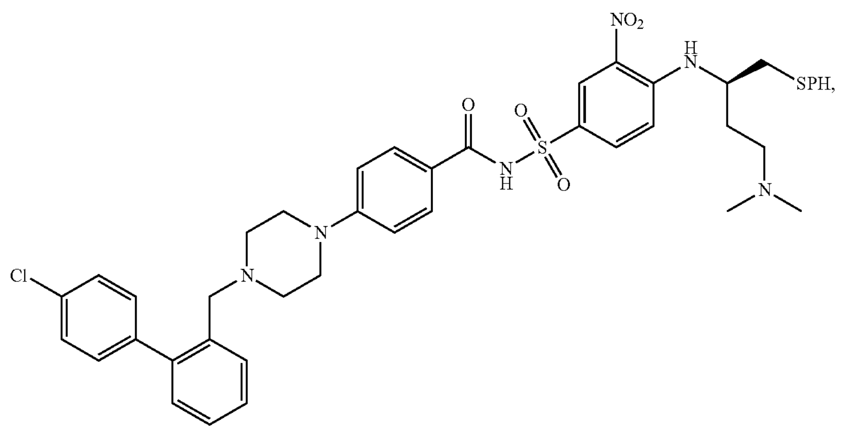
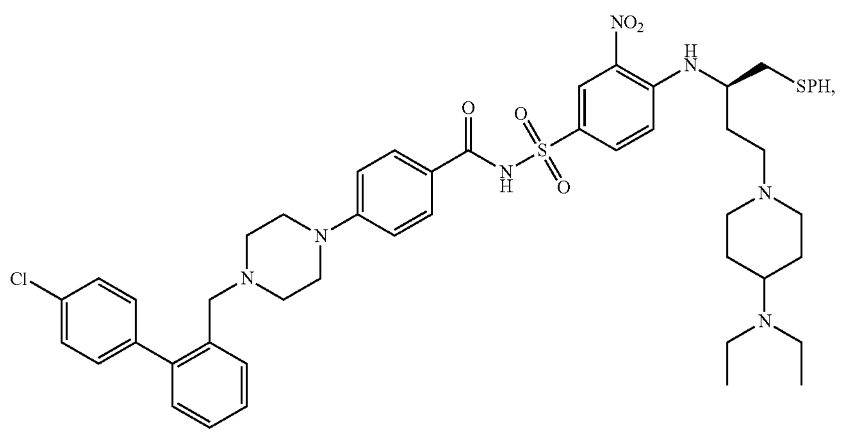
venetoclax (ABT-199), navitoclax (ABT-263), obatoclax mesylate (GX15-070), sabutoclax, TW-37, (R)-(−)-gossypol acetic acid, HA14-1, a BH3-mimetic, and oblimersen. In some embodiments, the Bcl inhibitor is selected from the group consisting of

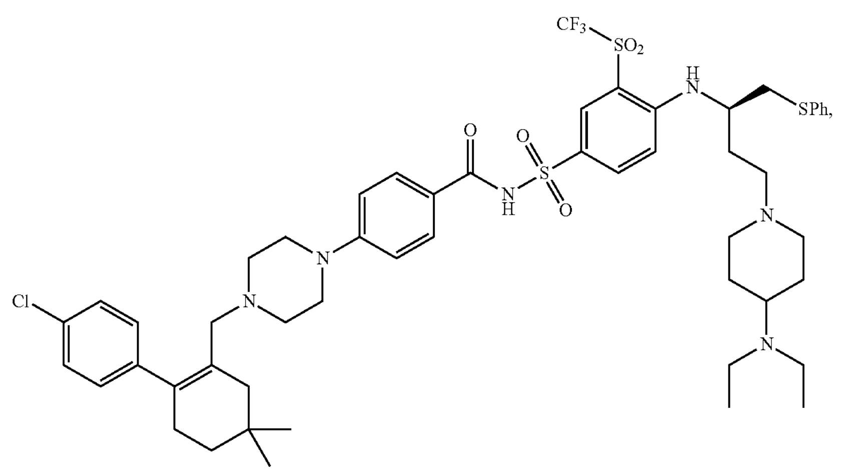
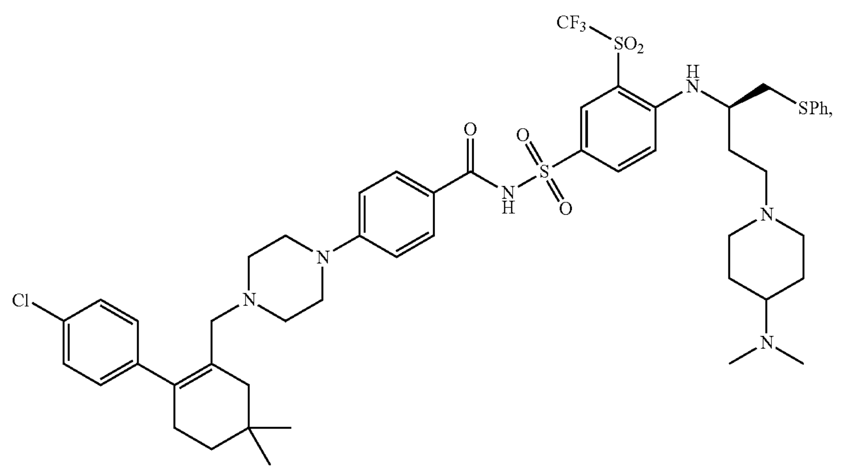
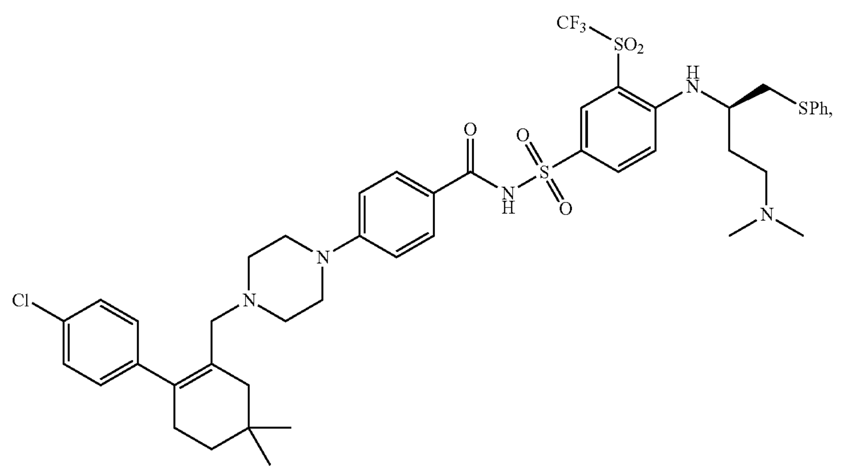

-continued
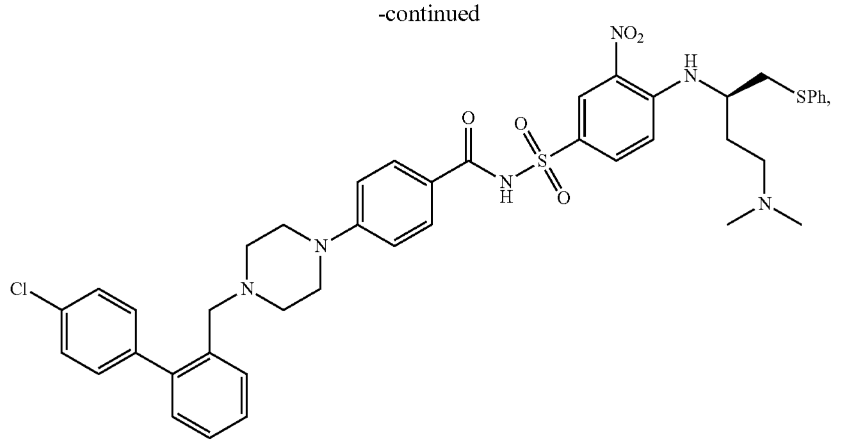
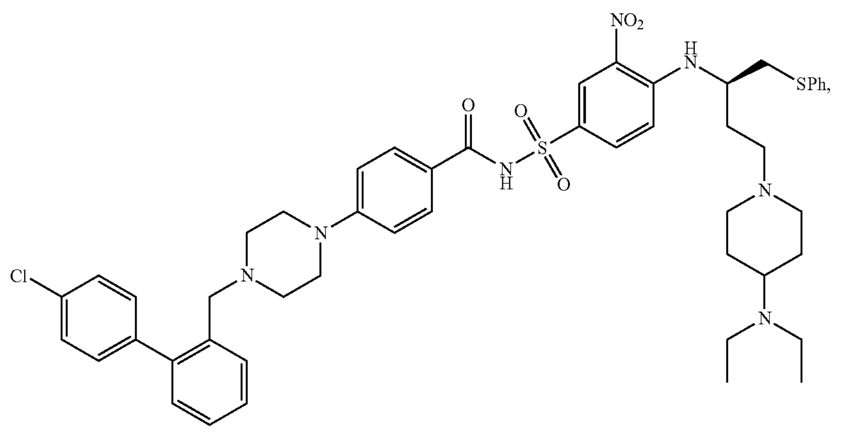
venetoclax (ABT-199), and navitoclax (ABT-263). In some embodiments, the Bcl inhibitor is selected from the group consisting of
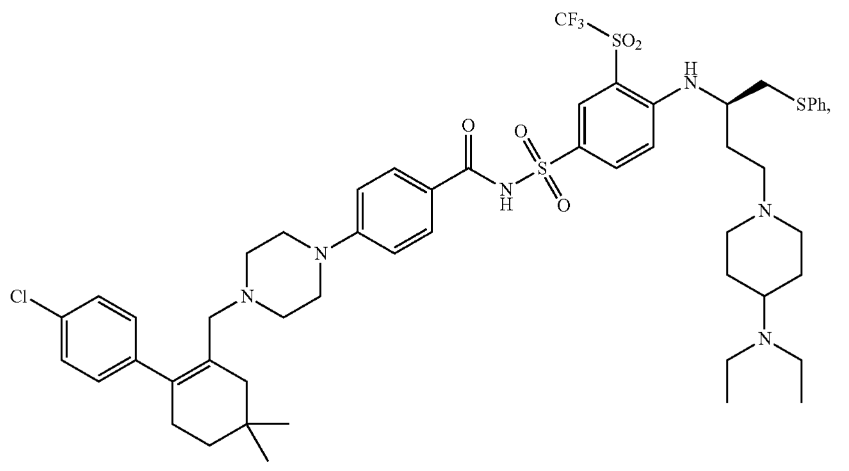

-continued
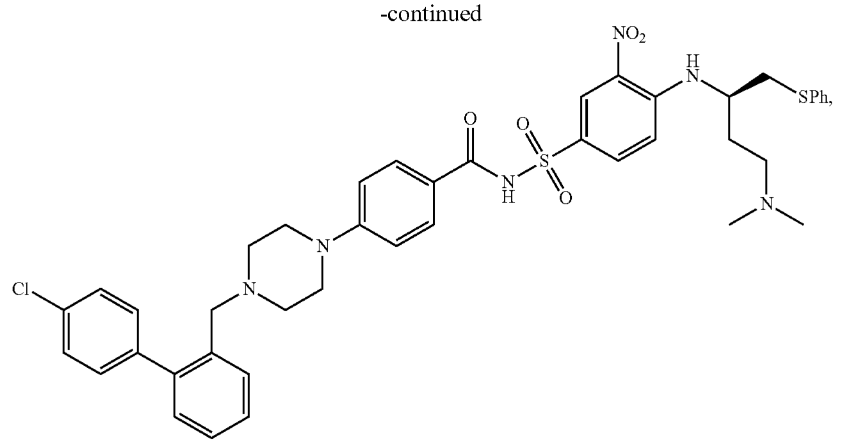
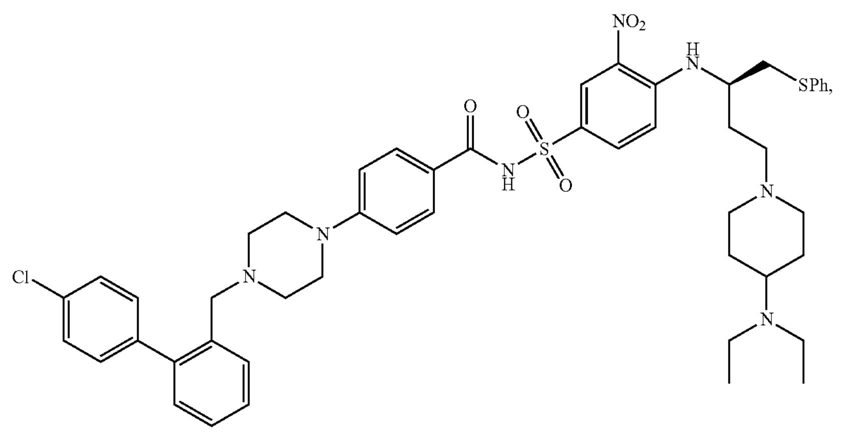
venetoclax (ABT-199), and navitoclax (ABT-263). In some embodiments, the Bcl inhibitor is
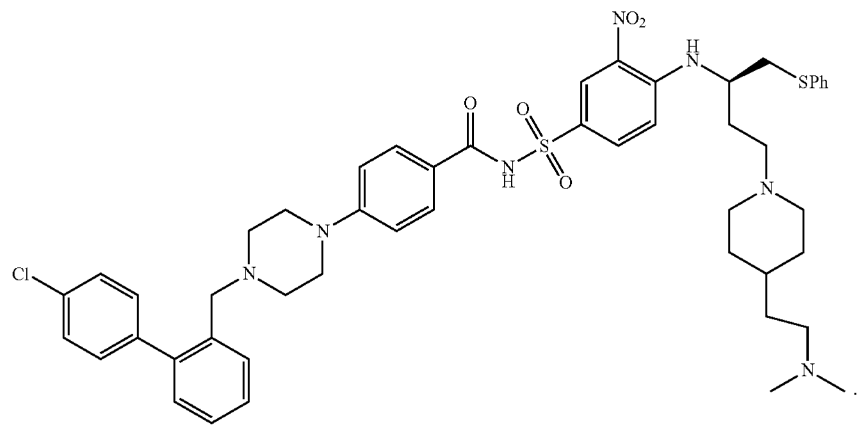

In some embodiments, the Bcl inhibitor is
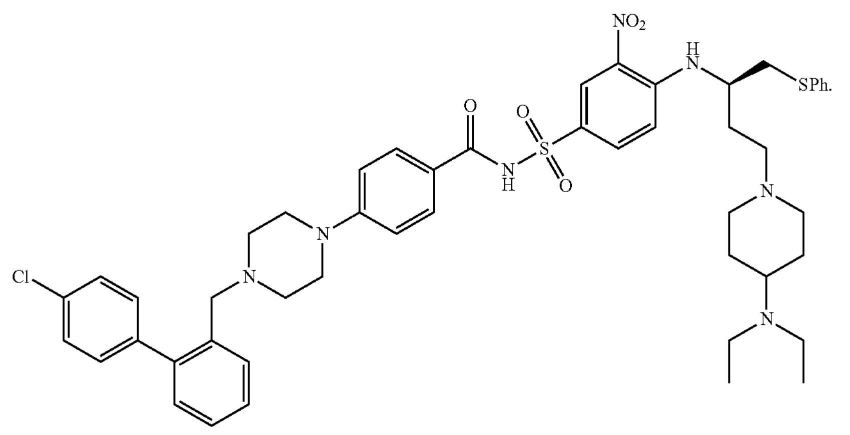
In some embodiments, the Bcl inhibitor is
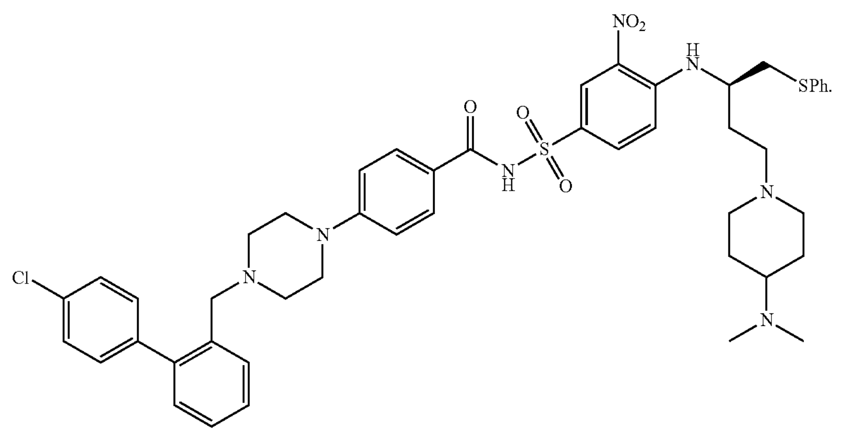
In some embodiments, the Bcl inhibitor is
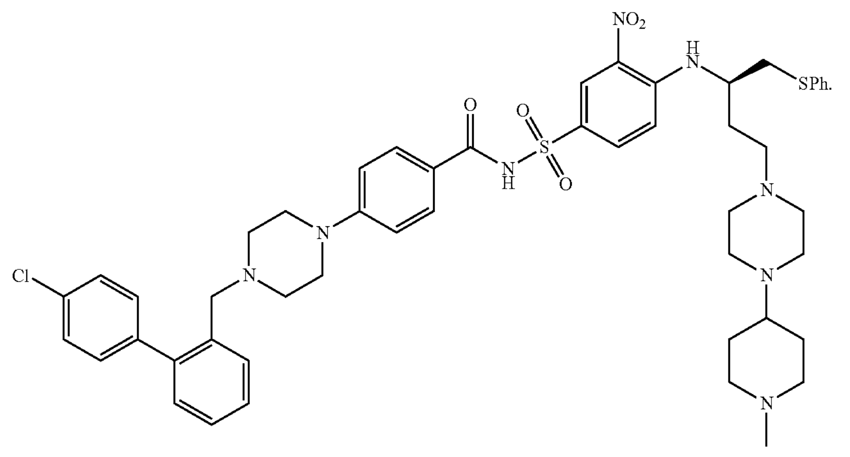

In some embodiments, the Bcl inhibitor is
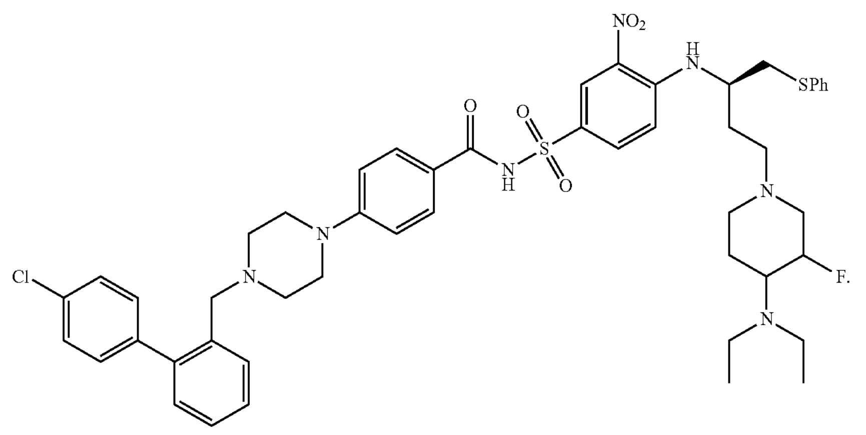
In some embodiments, the Bcl inhibitor is
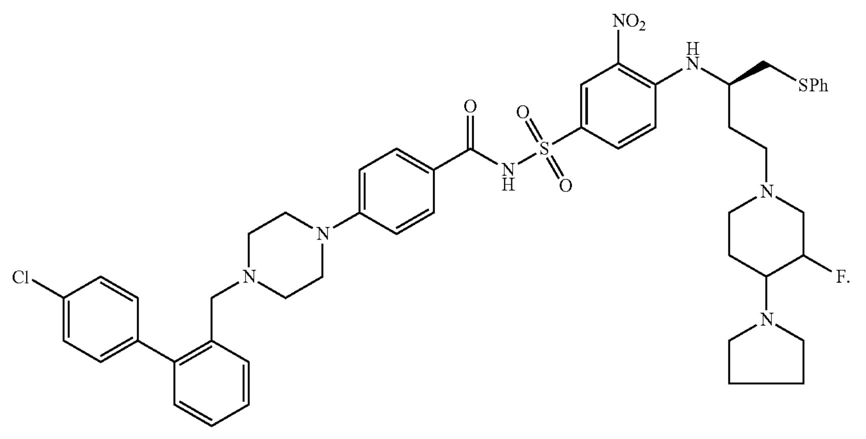
In some embodiments, the Bcl inhibitor is
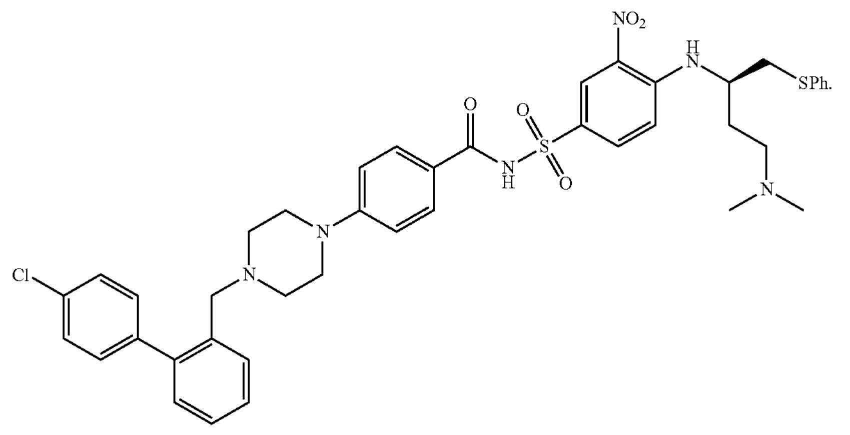

In some embodiments, the Bcl inhibitor is
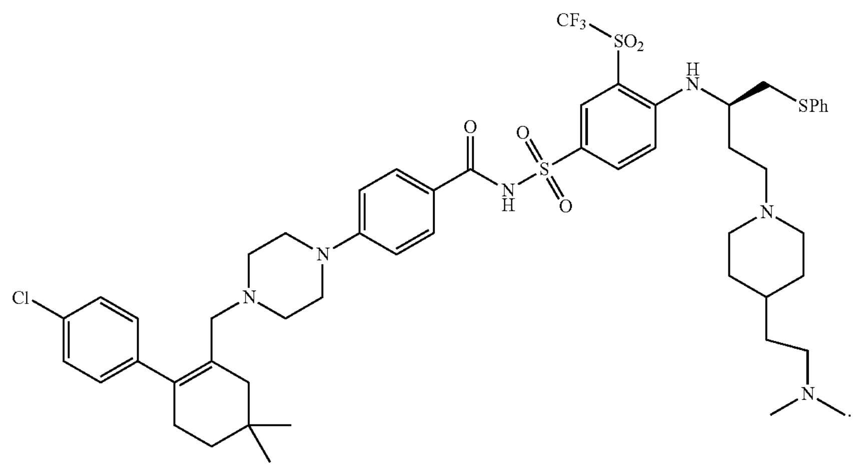
In some embodiments, the Bcl inhibitor is
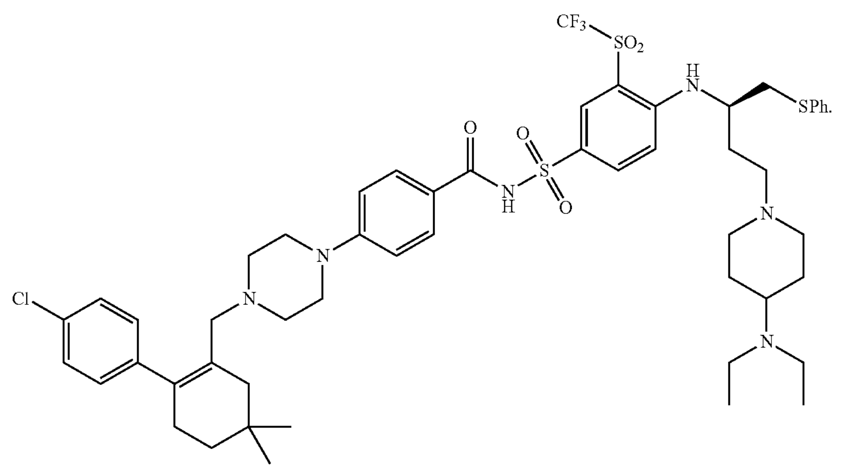
In some embodiments, the Bcl inhibitor is
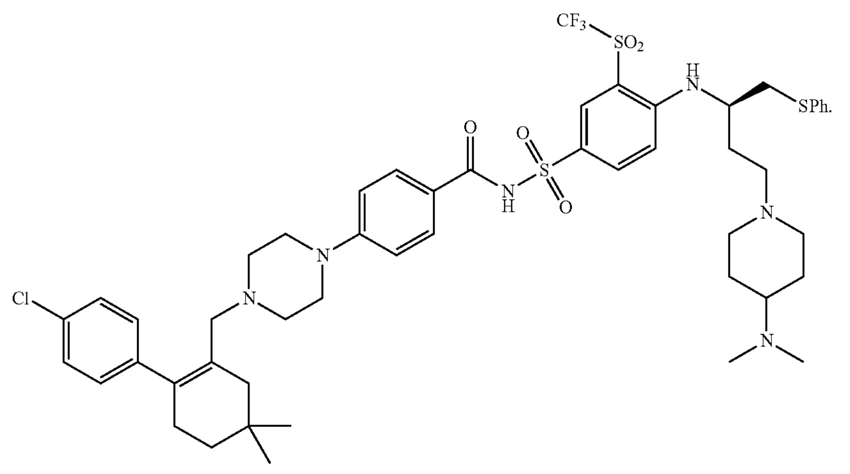

In some embodiments, the Bcl inhibitor is
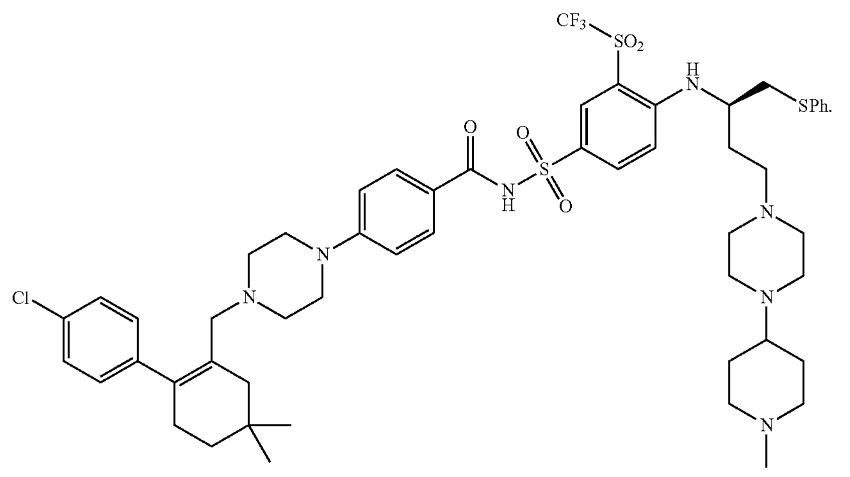
In some embodiments, the Bcl inhibitor is
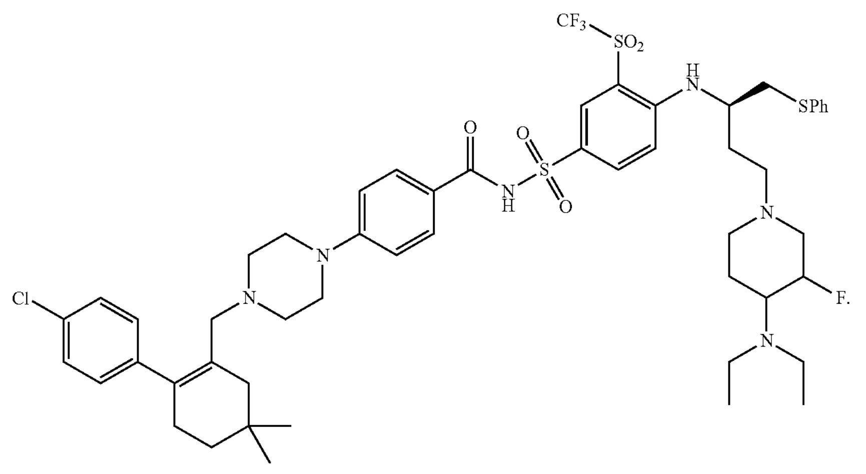
In some embodiments, the Bcl inhibitor is
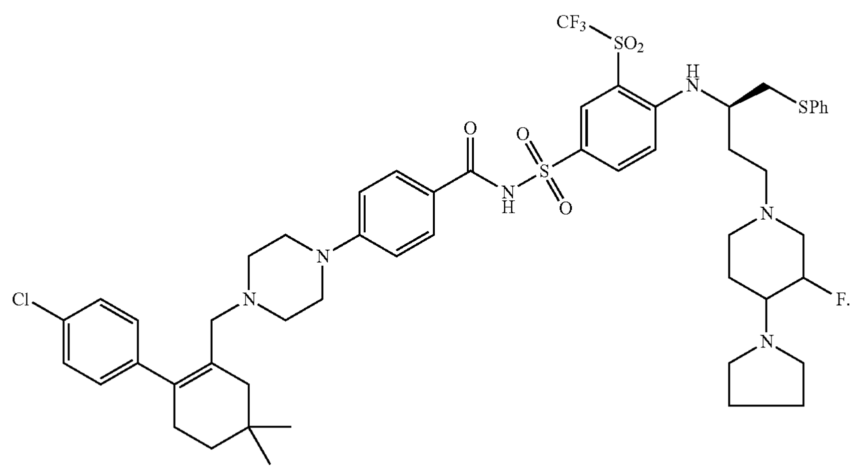

In some embodiments, the Bcl inhibitor is
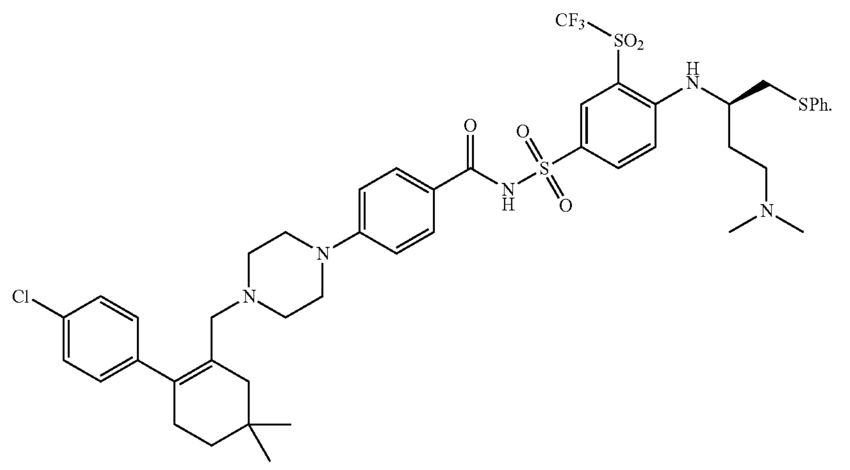
In some embodiments, the Bcl inhibitor is
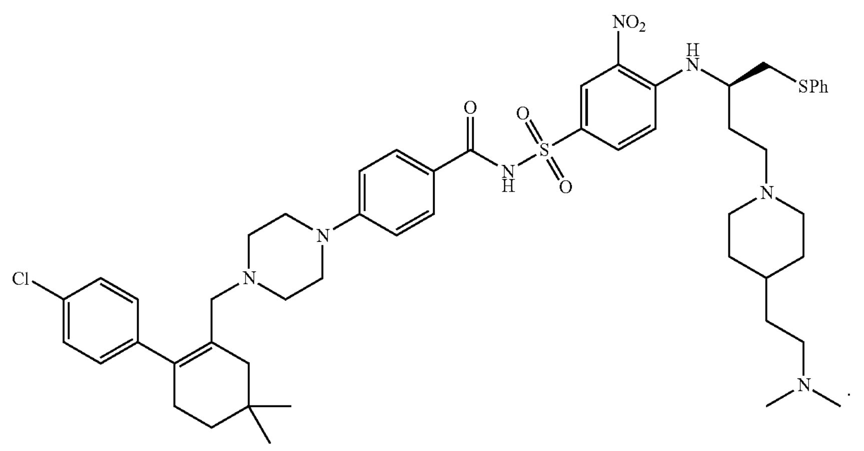
In some embodiments, the Bcl inhibitor is
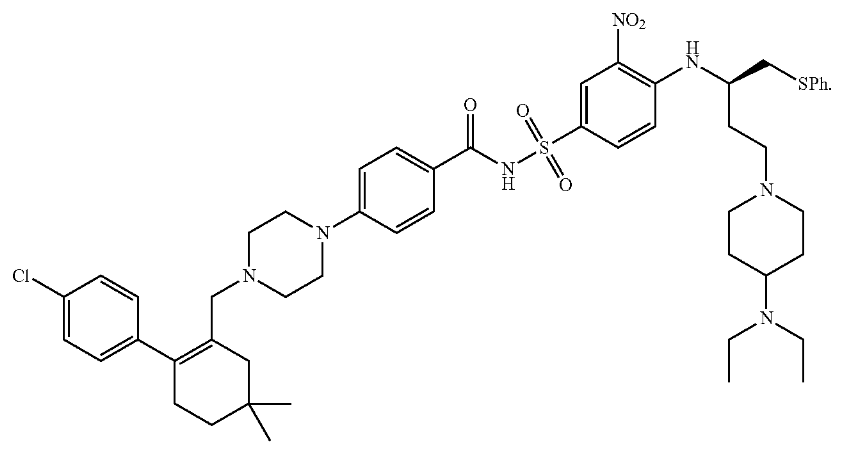

In some embodiments, the Bcl inhibitor is
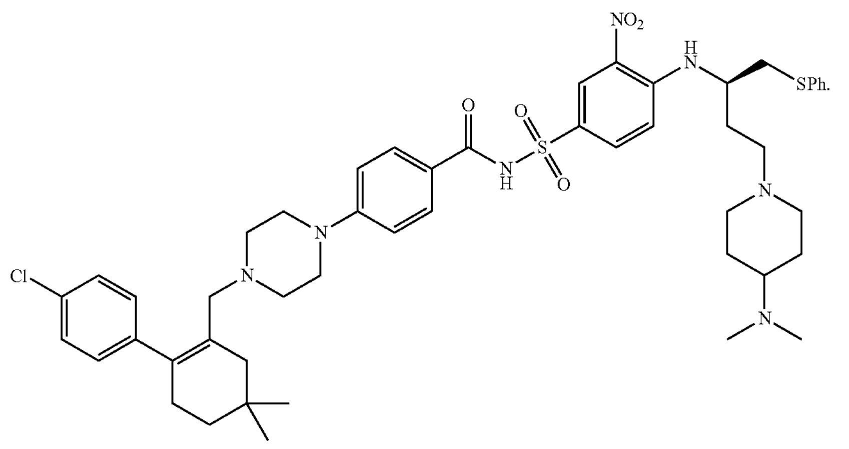
In some embodiments, the Bcl inhibitor is
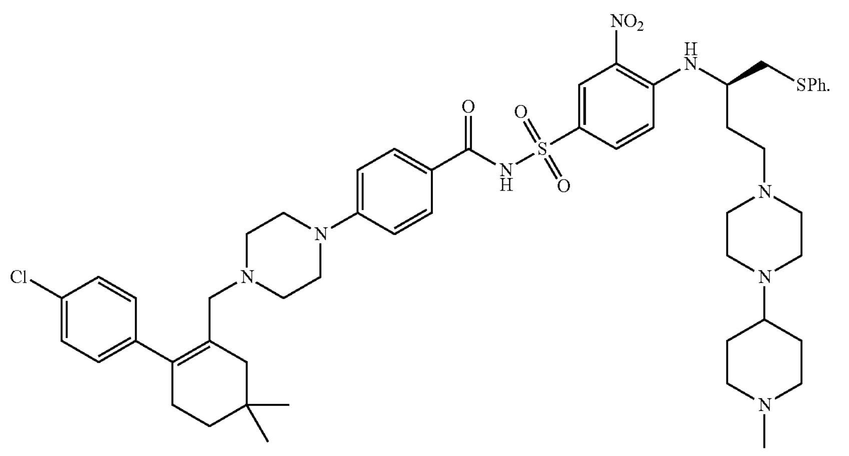
In some embodiments, the Bcl inhibitor is
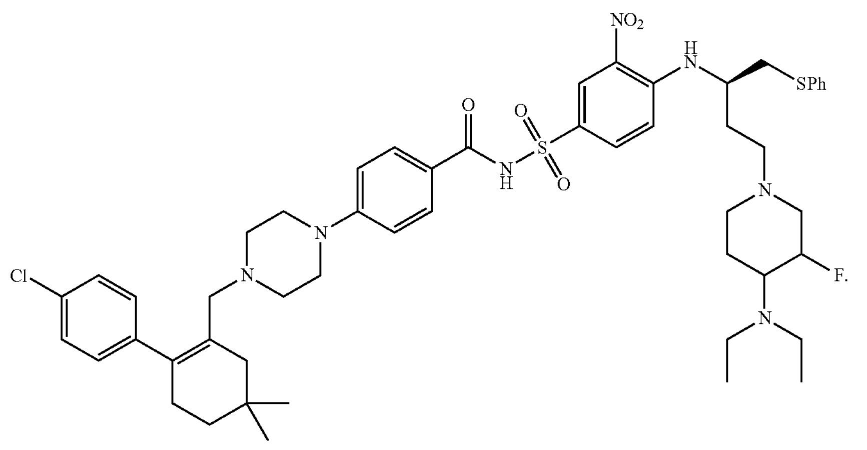

In some embodiments, the Bcl inhibitor is
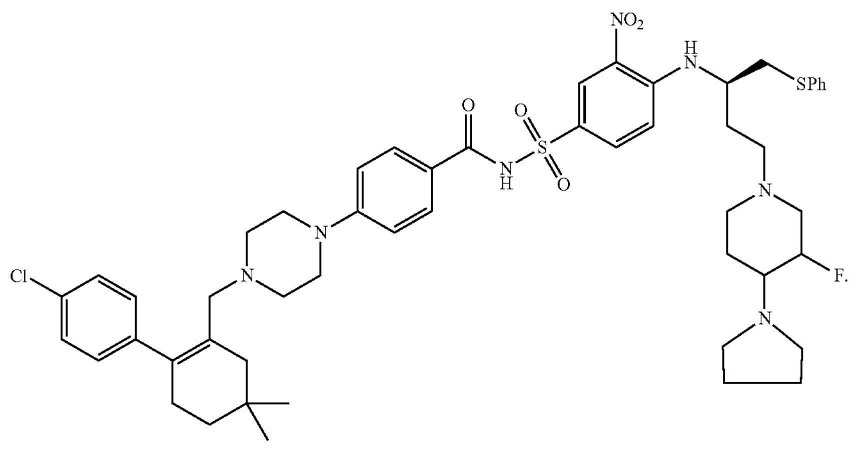
In some embodiments, the Bcl inhibitor is
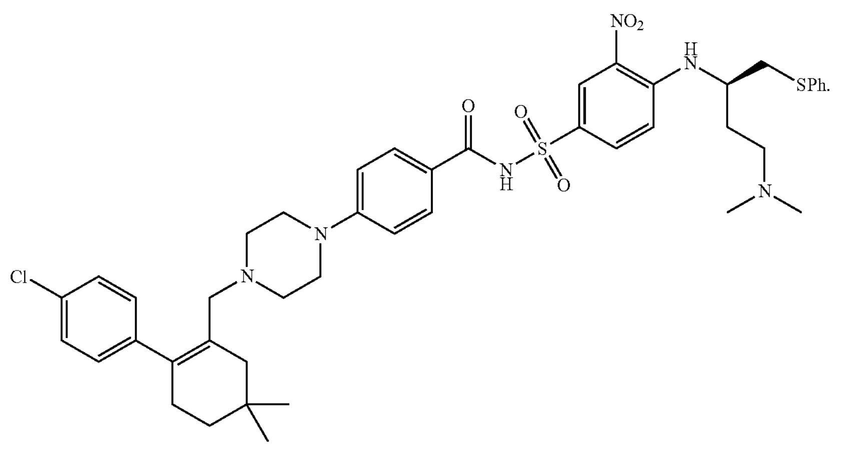
In some embodiments, the Bcl inhibitor is
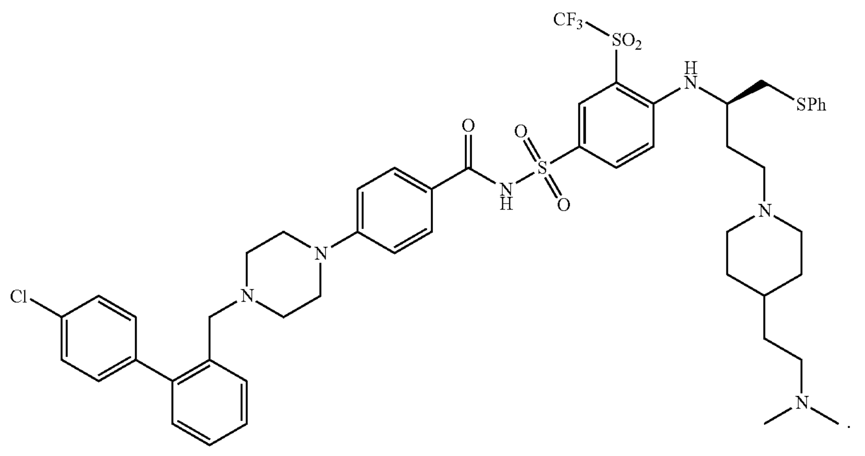

In some embodiments, the Bcl inhibitor is
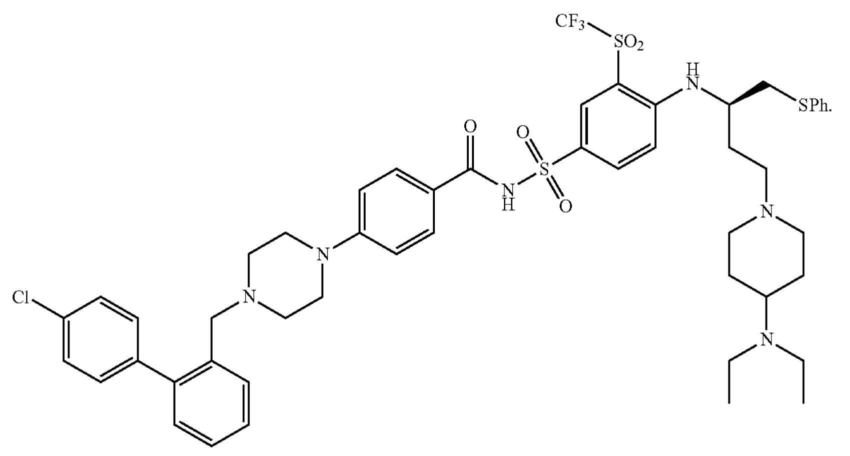
In some embodiments, the Bcl inhibitor is
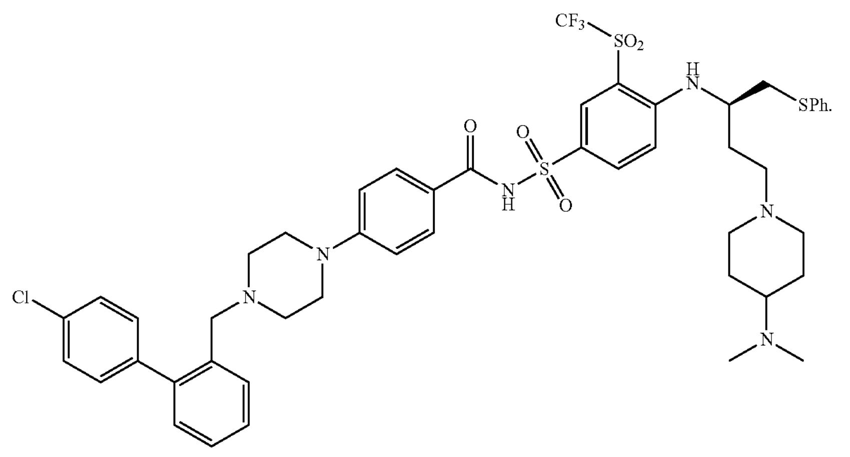
In some embodiments, the Bcl inhibitor is
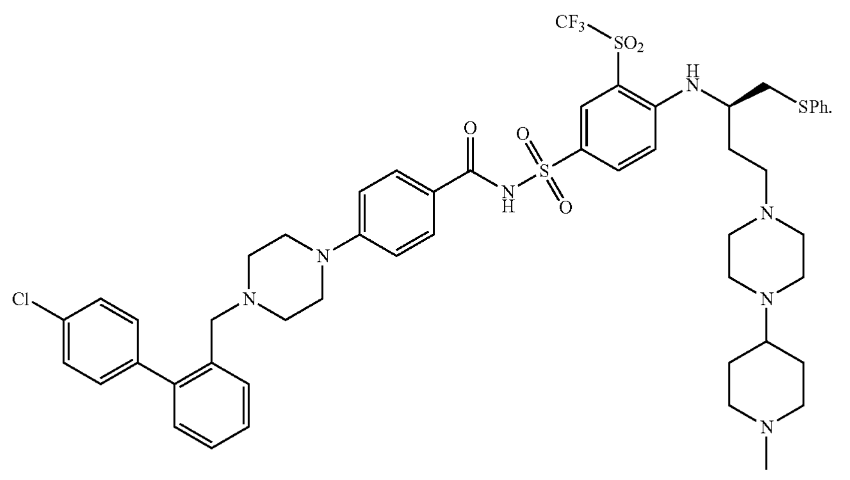

In some embodiments, the Bcl inhibitor is
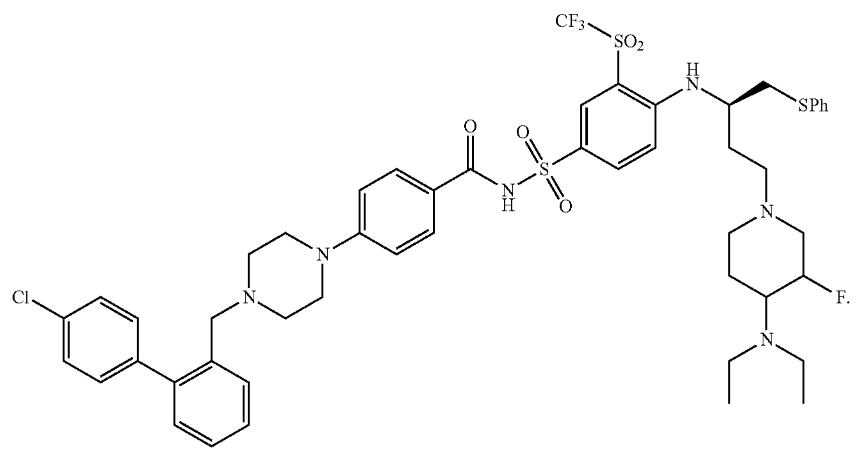
In some embodiments, the Bcl inhibitor is
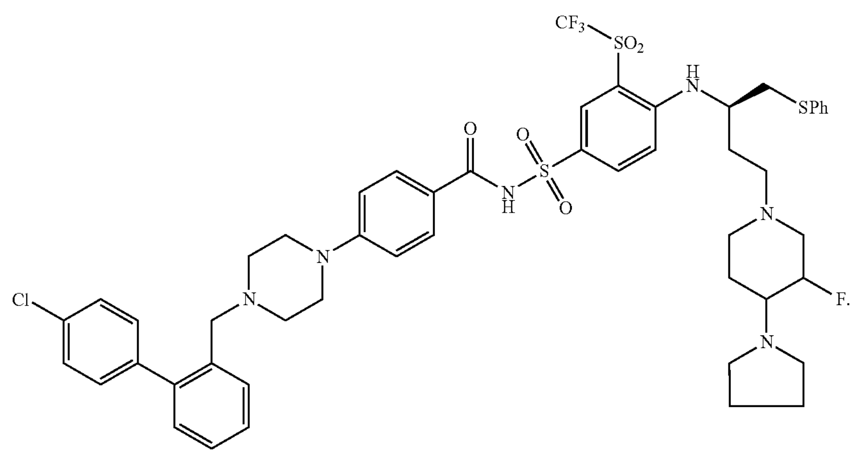
In some embodiments, the Bcl inhibitor is
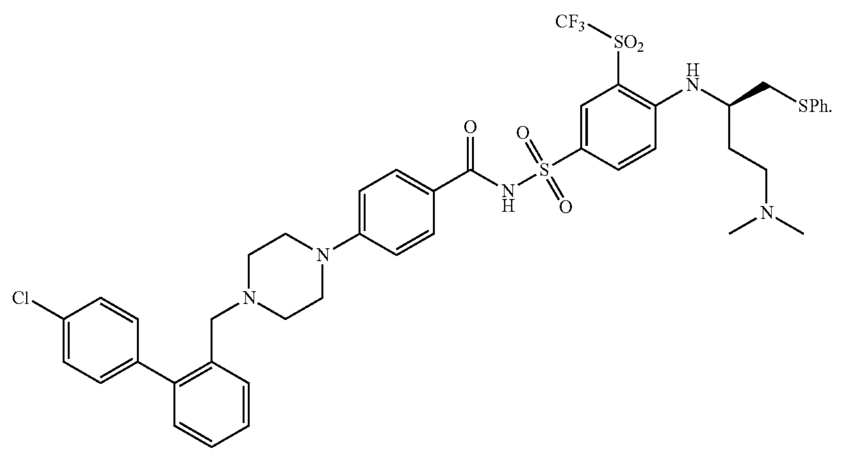
In some embodiments, the Bcl inhibitor is venetoclax. In some embodiments, the Bcl inhibitor is navitoclax.
In some embodiments, the liposomal compositions provided therein comprise a therapeutic agent. In some embodiments, the therapeutic agent is a hydrophobic therapeutic agent. In some embodiments, the therapeutic agent is encapsulated in the liposomes. In some embodiments, the therapeutic agent is external to the liposomes. In some embodiments of all the aforementioned aspects, the liposome further comprises a therapeutic agent. In some embodiments, the therapeutic agent is encapsulated in the liposome. In some embodiments, the liposomal compositions provided therein comprise a therapeutic agent. In some embodiments, the therapeutic agent is a hydrophobic therapeutic agent. In some embodiments, the therapeutic agent has a c Log P of greater than about 2. In some embodiments, the therapeutic agent has a c Log P between about 2 and about 12. In some embodiments, the therapeutic agent has a c Log P between about 3 and about 12. In some embodiments, the therapeutic agent has a c Log P between about 2 and about 4. In some embodiments, the therapeutic agent has a c Log P between about 2 and about 8. In some embodiments, the therapeutic agent has a c Log P between about 4 and about 12. In some embodiments, the therapeutic agent has a c Log P between about 4 and about 8. In some embodiments, the therapeutic agent has a c Log P between about 8 and about 12. In some embodiments, the therapeutic agent has a c Log P between about 10 and about 12.

In some embodiments, the therapeutic agent can be protonated and its protonated form has a $pK_a$ of greater than about 2. In some embodiments, the therapeutic agent can be protonated and its protonated form has a $pK_a$ between about 3 and about 11. In some embodiments, the therapeutic agent can be protonated and its protonated form has a $pK_a$ between about 6 and about 11. In some embodiments, the therapeutic agent can be protonated and its protonated form has a $pK_a$ between about 8 and about 11. In some embodiments, the therapeutic agent can be protonated and its protonated form has a $pK_a$ between about 3 and about 6. In some embodiments, the therapeutic agent can be protonated and its protonated form has a $pK_a$ between about 6 and about 8. In some embodiments, the therapeutic agent can be protonated and its protonated form has a $pK_a$ between about 3 and about 8. In some embodiments, the therapeutic agent can be protonated and its protonated form has a $pK_a$ between about 2 and about 12. In some embodiments, the therapeutic agent can be protonated and its protonated form has a $pK_a$ between about 2 and about 8. In some embodiments, the therapeutic agent can be protonated and its protonated form has a $pK_a$ between about 2 and about 4. In some embodiments, the therapeutic agent can be protonated and its protonated form has a $pK_a$ between about 4 and about 12. In some embodiments, the therapeutic agent can be protonated and its protonated form has a $pK_a$ between about 4 and about 8. In some embodiments, the therapeutic agent can be protonated and its protonated form has a $pK_a$ between about 8 and about 12. In some embodiments, the therapeutic agent can be protonated and its protonated form has a $pK_a$ between about 10 and about 12.

In some embodiments, the liposomal compositions provided therein comprise an additional therapeutic agent. In some embodiments, the additional therapeutic agent is a hydrophobic therapeutic agent. In some embodiments, the additional therapeutic agent is a hydrophilic therapeutic agent. In some embodiments, the additional therapeutic agent is encapsulated in the liposomes. In some embodiments, the additional therapeutic agent is external to the liposomes. In some embodiments of all the aforementioned aspects, the liposome further comprises an additional therapeutic agent. In some embodiments, the additional therapeutic agent is encapsulated in the liposome.

In some embodiments, the additional therapeutic agent is an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, or a proteasome inhibitor.

In some embodiments, the additional therapeutic agent is an HSP90 inhibitor. In some embodiments, the HSP90 inhibitor is Luminespib.

In some embodiments, the additional therapeutic agent is an alkylating agent. In some embodiments, the additional therapeutic agent is an alkylating agent selected from the group consisting of Bendamustine and Chlorambucil.

In some embodiments, the additional therapeutic agent is an antitubulin agent. In some embodiments, the additional therapeutic agent is an antitubulin agent selected from the group consisting of Vincristine, Vinorelbine, and docetaxel.

In some embodiments, the additional therapeutic agent is an ATR inhibitor.

In some embodiments, the additional therapeutic agent is a RAF inhibitor. In some embodiments, the RAF inhibitor is Dabrafenib. In some embodiments, the additional therapeutic agent is a BRAF inhibitor. In some embodiments, the BRAF inhibitor is Vemurafenib.

In some embodiments, the additional therapeutic agent is a BTK inhibitor. In some embodiments, the BTK inhibitor is Ibrutinib.

In some embodiments, the additional therapeutic agent is an HDAC inhibitor. In some embodiments, the HDAC inhibitor is Panobinostat.

In some embodiments, the additional therapeutic agent is a JAK inhibitor. In some embodiments, the JAK inhibitor is Ruxolitinib.

In some embodiments, the additional therapeutic agent is an MEK inhibitor. In some embodiments, the additional therapeutic agent is an MEK inhibitor selected from the group consisting of Selumetinib and Cobimetinib.

In some embodiments, the additional therapeutic agent is a PARP inhibitor. In some embodiments, the additional therapeutic agent is a PARP inhibitor selected from the group consisting of Talazoparib, Niraparib, and Rucaparib.

In some embodiments, the additional therapeutic agent is a PI3K inhibitor. In some embodiments, the PI3K inhibitor is Idelalisib.

In some embodiments, the additional therapeutic agent is a proteasome inhibitor. In some embodiments, the proteasome inhibitor is Carfilzomib.

In some embodiments, the additional therapeutic agent is an SMO inhibitor. In some embodiments, the additional therapeutic agent is an SMO inhibitor selected from the group consisting of Sonidegib and Vismodegib.

In some embodiments, the additional therapeutic agent is a tyrosine kinase inhibitor. In some embodiments, the additional therapeutic agent is a tyrosine kinase inhibitor selected from the group consisting of Brigatinib, Lenvatinib, Afatinib, Axitinib, Cabozantinib, Ponatinib, Sorafenib, Osimertinib, Regorafenib, Bosutinib, Crizotinib, Vandetanib, Nilotinib, Alectinib, Ceritinib, Dasatinib, Pazopanib, Sunitinib, Erlotinib, Imatinib, Gefitinib, Lapatinib.

In some embodiments, the additional therapeutic agent is a topoisomerase inhibitor. In some embodiments, the additional therapeutic agent is a topoisomerase I inhibitor. In some embodiments, the topoisomerase inhibitor is Irinotecan.

In some embodiments, the additional therapeutic agent is a Bcl inhibitor such as those described above. In some embodiments, the additional therapeutic agent is an antineoplastic agent. Suitable antineoplastic agents are for non-limiting example:

- "Signal transduction inhibitors" which interfere with or prevents signals that cause cancer cells to grow or divide;
- "Cytotoxic agents";
- "Cell cycle inhibitors" or "cell cycle control inhibitors" which interfere with the progress of a cell through its normal cell cycle, the life span of a cell, from the mitosis that gives it origin to the events following mitosis that divides it into daughter cells;
- "Checkpoint inhibitors" which interfere with the normal function of cell cycle checkpoints, e.g., the S/G2 checkpoint, G2/M checkpoint and GUS checkpoint, such as S/G2 or G2/M checkpoint inhibitors such as bleomycin, docetaxel, doxorubicin, etoposide, paclitaxel, vinblastine, vincristine, vindesine and vinorelbine; G1/early-S checkpoint inhibitors; and G2/M checkpoint inhibitors;
- "Topoisomerase inhibitors", which interfere with topoisomerase I or II activity, enzymes necessary for DNA replication and transcription, such as camptothecins, irinotecan and topotecan;
- "Receptor tyrosine kinase inhibitors" which interfere with the activity of growth factor receptors that possess tyrosine kinase activity, such as genistein, trastuzumab, ZD1839;
- "Apoptosis inducing agents" which promote programmed cell death;
- "Antimetabolites," such as cytidine analogs such as cytarabine, 5-Azacytidine, and gemcitabine (2',2'-Difluorodeoxycytidine), or Hydroxyurea, which closely resemble an essential metabolite and therefore interfere with physiological reactions involving it;
- "Telomerase inhibitors" which interfere with the activity of a telomerase, an enzyme that extends telomere length and extends the lifetime of the cell and its replicative capacity;
- "Cyclin-dependent kinase inhibitors" which interfere with cyclin-dependent kinases that control the major steps between different phases of the cell cycle through phosphorylation of cell proteins such as histones, cytoskeletal proteins, transcription factors, tumor suppresser genes and the like;
- "DNA damaging agents" such as carboplatin, cisplatin, cyclophosphamide, doxorubicin, daunorubicin, epirubicin, mitomycin C, mitoxantrone;
- "DNA repair inhibitors" including 5-fluorouracil (5-FU) or FUDR, gemcitabine and methotrexate;
- "Immunomodulating agents" which stimulate or suppress the immune system and may help the body fight cancer, infection, or other diseases; for example specific immunomodulating agents, such as monoclonal antibodies, cytokines, and vaccines, affect specific parts of the immune system; and nonspecific immunomodulating agents, such as BCG and levamisole, affect the immune system in a general way;
- "Anti-angiogenic agents" which interfere with the generation of new blood vessels or growth of existing blood vessels that occurs during tumor growth; and
- "Mitochondrial poisons" which directly or indirectly disrupt mitochondrial respiratory chain function.

The mechanism of action of one or more of the agents may not be known or may be incorrectly identified.

Other anti-neoplastic agents include paclitaxel, an etoposide-compound, a camptothecin-compound, idarubicin, carboplatin, oxaliplatin, adriamycin, mitomycin, ansamitocin, bleomycin, cytosine arabinoside, arabinosyl adenine, mercaptopolylysine, vincristine, busulfan, chlorambucil, melphalan, mercaptopurine, mitotane, procarbazine hydrochloride, dactinomycin, mitomycin, plicamycin, aminoglutethimide, estramustine phosphate sodium, flutamide, leuprolide acetate, megestrol acetate, tamoxifen citrate, testolactone, trilostane, amsacrine, asparaginase, interferon, teniposide, vinblastine sulfate, vincristine sulfate, bleomycin, methotrexate, valrubicin, carzelesin, paclitaxel, taxotane, camptothecin, doxorubicin, daunomycin, cisplatin, 5 fluorouracil, methotrexate; anti-inflammatory agents such as indomethacin, ibuprofen, ketoprofen, flubiprofen, dichlofenac, piroxicam, tenoxicam, naproxen, aspirin, and acetaminophen; sex hormones such as testosterone, estrogen, progestone, estradiol; antihypertensive agents such as captopril, ramipril, terazosin, minoxidil, and parazosin; antiemetics such as ondansetron and granisetron; antibiotics such as metronidazole, and fusidic acid; cyclosporine; prostaglandins; biphenyl dimethyl dicarboxylic acid, carboplatin; antifungal agents such as itraconazole, ketoconazole, and amphotericin; steroids such as triamcinolone acetonide, hydrocortisone, dexamethasone, prednisolone, and betamethasone; cyclosporine, and functionally equivalent analogues, derivatives or combinations thereof.

In some embodiments, the liposomal compositions provided therein comprise an additional therapeutic agent. In some embodiments, the additional therapeutic agent is a hydrophobic therapeutic agent. In some embodiments, the additional therapeutic agent is encapsulated in the liposomes. In some embodiments, the additional therapeutic agent is external to the liposomes. In some embodiments of all the aforementioned aspects, the liposome further comprises an additional therapeutic agent. In some embodiments, the additional therapeutic agent is encapsulated in the liposome. In some embodiments, the additional therapeutic agent has a c Log P of greater than about 2. In some embodiments, the additional therapeutic agent has a c Log P between about −6 and about 12. In some embodiments, the additional therapeutic agent has a c Log P between about −6 and about 0. In some embodiments, the additional therapeutic agent has a c Log P between about −3 and about 0. In some embodiments, the additional therapeutic agent has a c Log P between about 0 and about 2. In some embodiments, the additional therapeutic agent has a c Log P between about −1 and about 12. In some embodiments, the additional therapeutic agent has a c Log P between about 3 and about 12. In some embodiments, the additional therapeutic agent has a c Log P between about −6 and about −1. In some embodiments, the additional therapeutic agent has a c Log P between about −1 and about 3. In some embodiments, the additional therapeutic agent has a c Log P between about 2 and about 12. In some embodiments, the additional therapeutic agent has a c Log P between about 2 and about 4. In some embodiments, the additional therapeutic agent has a c Log P between about 2 and about 8. In some embodiments, the additional therapeutic agent has a c Log P between about 4 and about 12. In some embodiments, the additional therapeutic agent has a c Log P between about 4 and about 8. In some embodiments, the additional therapeutic agent has a c Log P between about 8 and about 12. In some embodiments, the additional therapeutic agent has a c Log P between about 10 and about 12.

In some embodiments, the additional therapeutic agent can be protonated and its protonated form has a $pK_a$ of greater than about 2. In some embodiments, the additional therapeutic agent can be protonated and its protonated form has a $pK_a$ between about −6 and about 12. In some embodiments, the additional therapeutic agent can be protonated and its protonated form has a $pK_a$ between about −6 and about 11. In some embodiments, the additional therapeutic agent can be protonated and its protonated form has a $pK_a$ between about 3 and about 11. In some embodiments, the additional therapeutic agent can be protonated and its protonated form has a $pK_a$ between about 6 and about 11. In some embodiments, the additional therapeutic agent can be protonated and its protonated form has a $pK_a$ between about 8 and about 11. In some embodiments, the additional therapeutic agent can be protonated and its protonated form has a $pK_a$ between about −6 and about 3. In some embodiments, the additional therapeutic agent can be protonated and its protonated form has a $pK_a$ between about 3 and about 6. In some embodiments, the additional therapeutic agent can be protonated and its protonated form has a $pK_a$ between about 6 and about 8. In some embodiments, the additional therapeutic agent can be protonated and its protonated form has a $pK_a$ between about −6 and about 8. In some embodiments, the additional therapeutic agent can be protonated and its protonated form has a $pK_a$ between about 3 and about 8. In some embodiments, the additional therapeutic agent can be protonated and its protonated form has a $pK_a$ between about −6 and about 6. In some embodiments, the additional therapeutic agent can be protonated and its protonated form has a $pK_a$ between about 2 and about 12. In some embodiments, the additional therapeutic agent can be protonated and its protonated form has a $pK_a$ between about 2 and about 8. In some embodiments, the additional therapeutic agent can be protonated and its protonated form has a $pK_a$ between about 2 and about 4. In some embodiments, the additional therapeutic agent can be protonated and its protonated form has a $pK_a$ between about 4 and about 12. In some embodiments, the additional therapeutic agent can be protonated and its protonated form has a $pK_a$ between about 4 and about 8. In some embodiments, the additional therapeutic agent can be protonated and its protonated form has a $pK_a$ between about 8 and about 12. In some embodiments, the additional therapeutic agent can be protonated and its protonated form has a $pK_a$ between about 10 and about 12.

Process for Making Liposomes and Liposomal Compositions

Liposomes can be prepared as described in "Liposomes: Rational Design" (A. S. Janoff, ed., Marcel Dekker, Inc., New York, NY), or by additional techniques known to those knowledgeable in the art. Suitable liposomes include large unilamellar vesicles (LUVs), multilamellar vesicles (MLVs), small unilamellar vesicles (SUVs) and interdigitating fusion liposomes.

Lipids

Liposomes may contain therapeutic lipids, which examples include ether lipids, phosphatidic acid, phosphonates, ceramide and ceramide analogs, sphingosine and sphingosine analogs and serine-containing lipids. Liposomes may also contain dialiphatic chain lipids, for example phospholipids, such as phosphtidic acid lipids, phosphatidyl glycerols, phosphatidylinositols, phosphatidylcholine lipids, phosphatidylethanolamine lipids, phosphatidylserine lipids, and phosphatidylglycerol lipids. Liposomes may also contain diglycerides, dialiphatic glycolipids, or single lipids. Liposomes may be prepared to contain a phosphatidylcholine lipid, such as distearoylphosphatidylcholine (DSPC). The phospholipid may be selected from the group consisting of a phosphatidylcholine, a sphingolipid, and a hydrogenated sphingolipid. For example, the phospholipid may be Egg phosphatidylcholine (Egg PC), 1-palmitoyl-2-oleoyl-sn-glycero-3-phosphocholine (POPC), 1,2-dipalmitoyl-sn-glycero-3-phosphocholine (DPPC), Egg sphingomyelin, 1,2-Dioleoyl-sn-glycero-3-phosphoethanolamine (DOPE), 1,2-Distearoyl-sn-glycero-3-phospho-L-serine (DSPS), 1,2-Distearoyl-sn-glycero-3-phospho-L-serine sodium salt (DSPS-Na), 2-Oleoyl-1-palmitoyl-sn-glycero-3-phospho-L-serine (POPS), and 2-Oleoyl-1-palmitoyl-sn-glycero-3-phospho-L-serine sodium salt (POPS—Na).

Liposomes may also be prepared with surface stabilizing hydrophilic polymer-lipid conjugates. Hydrophilic polymer-lipid conjugates comprise a polymeric moiety and a lipid moiety. The polymeric moiety can be a PEG moiety. The lipid moiety can be based on a phospholipid. The phospholipid may be selected from the group consisting of a phosphatidylcholine, a sphingolipid, and a hydrogenated sphingolipid. For example, the phospholipid may be Egg phosphatidylcholine (Egg PC), 1-palmitoyl-2-oleoyl-sn-glycero-3-phosphocholine (POPC), 1,2-dipalmitoyl-sn-glycero-3-phosphocholine (DPPC), Egg sphingomyelin, 1,2-Dioleoyl-sn-glycero-3-phosphoethanolamine (DOPE), 1,2-Distearoyl-sn-glycero-3-phospho-L-serine (DSPS), 1,2-Distearoyl-sn-glycero-3-phospho-L-serine sodium salt (DSPS-Na), 2-Oleoyl-1-palmitoyl-sn-glycero-3-phospho-L-serine (POPS), and 2-Oleoyl-1-palmitoyl-sn-glycero-3-phospho-L-serine sodium salt (POPS—Na). Exemplary polymer-lipid conjugates may be 1,2-distearoyl-rac-glycero-3-methoxypoly(ethylene glycol) (such as DSG-PEG2000 or DSG-PEG1000), 1,2-dimyristoyl-rac-glycero-3-methoxypoly(ethylene glycol) (such as DMG-PEG2000 or DMG-PEG1000), 1,2-dipalmitoyl-rac-glycero-3-methoxypoly (ehtlyene glycol) (such as DPG-PEG2000 or DPG-PEG1000), 1,2-distearoyl-sn-glycero-3-phosphoethanolamine-poly(ethylene glycol) (such as DSPE-PEG2000 or DSPE-PEG1000), N-palmitoyl-sphingosine-1-{succinyl[methoxy(polyethylene glycol)]} (such as C16 PEG2000 ceramide), PEG-derivatized cholesterol (such as mPEG cholesterol), sphingomyelin, or dihydrosphingomyelin. The average molecular weight of the polymeric moiety of the polymer-lipid conjugates may vary from about 1000 g/mol to about 5000 g/mol. The average molecular weight of the polymeric moiety of the polymer-lipid conjugates may vary from about 1000 g/mol to about 2000 g/mol. The average molecular weight of the polymeric moiety of the polymer-lipid conjugates may be about 1000 g/mol. The average molecular weight of the polymeric moiety of the polymer-lipid conjugates may be about 2000 g/mol. The average molecular weight of the polymeric moiety of the polymer-lipid conjugates may be about 5000 g/mol.

The incorporation of negatively charged lipids such as phosphatidylglycerol (PG) and phosphatidylinositol (PI) may also be added to liposome formulations to increase the circulation longevity of the carrier. These lipids may be employed to replace hydrophilic polymer-lipid conjugates as surface stabilizing agents or employed in combination with hydrophilic polymer-lipid conjugates.

Sterols

Liposomes may also contain a sterol, such as cholesterol, a cholesterol derivative, or a phytosterol (such as 0-sitosterol).

Process for Loading Liposomes

Various methods may be utilized to encapsulate active agents in liposomes. "Encapsulation," includes covalent or non-covalent association of an agent with the liposomes. For example, this can be by interaction of the agent with the outer layer or layers of the liposome or entrapment of an agent within the liposome, equilibrium being achieved between different portions of the liposome. Thus encapsulation of an agent can be by association of the agent by interaction with the bilayer of the liposomes through covalent or non-covalent interaction with the lipid components or entrapment in the aqueous interior of the liposome, or in equilibrium between the internal aqueous phase and the bilayer. "Loading" refers to the act of encapsulating one or more agents into a delivery vehicle.

When a combination of therapeutic agents is sought, it will be apparent to those skilled in the art that encapsulation of the desired combination can be achieved either through encapsulation in separate delivery vehicles or within the same delivery vehicle. Where encapsulation into separate liposomes is desired, the lipid composition of each liposome may be quite different to allow for coordinated pharmacokinetics. By altering the vehicle composition, release rates of encapsulated drugs can be matched to allow desired ratios of the drugs to be delivered to the tumor site. Means of altering release rates include increasing the acyl-chain length of vesicle forming lipids to improve drug retention, controlling the exchange of surface grafted hydrophilic polymers such as PEG out of the liposome membrane and incorporating membrane-rigidifying agents such as sterols into the membrane. It should be apparent to those skilled in the art that if a first and second drug are desired to be administered at a specific drug ratio and if the second drug is retained poorly within the liposome composition of the first drug, that improved pharmacokinetics may be achieved by encapsulating the second drug in a second liposome composition. Alternatively, two or more agents may be encapsulated within the same liposome.

Techniques for encapsulation are dependent on the nature of the delivery vehicles and on the nature of the therapeutic agent to be encapsulated. For example, therapeutic agents may be loaded into liposomes using both passive and active loading methods. Passive methods of encapsulating active agents in liposomes involve encapsulating the agent during the preparation of the liposomes. This includes a passive entrapment method described by Bangham, et al. (*J. Mol. Biol.* (1965) 12:238). This technique results in the formation of multilamellar vesicles (MLVs) that can be converted to large unilamellar vesicles (LUVs) or small unilamellar vesicles (SUVs) upon extrusion. Another suitable method of passive encapsulation includes an ether injection technique described by Deamer and Bangham (*Biochim. Biophys. Acta* (1976) 443:629) and the Reverse Phase Evaporation technique as described by Szoka and Paphadjopoulos (*P.N.A.S.* (1978) 75:4194). In addition, another suitable method of passive encapsulation involves passive equilibration after the formation of liposomes. This process involves incubating pre-formed liposomes under altered or non-ambient (based on temperature, pressure, etc.) conditions and adding a therapeutic agent to the exterior of the liposomes. The therapeutic agent then equilibrates into the interior of the liposomes, across the liposomal membrane. The liposomes are then returned to ambient conditions and unencapsulated therapeutic agent, if present, is removed via dialysis or another suitable method.

Active methods of encapsulation include the pH gradient loading technique described in U.S. Pat. Nos. 5,616,341, 5,736,155 and 5,785,987 and active metal-loading. One method of pH gradient loading is the citrate-base loading method utilizing citrate as the internal buffer at a pH of 4.0 and a neutral exterior buffer. Other methods employed to establish and maintain a pH gradient across a liposome involve the use of an ionophore that can insert into the liposome membrane and transport ions across membranes in exchange for protons (see U.S. Pat. No. 5,837,282). Another technique utilizing transition metals to drive the uptake of drugs into liposomes via complexation in the absence of an ionophore may also be used. This technique relies on the formation of a drug-metal complex rather than the establishment of a pH gradient to drive uptake of drug.

Preferred methods of encapsulation of poorly water-soluble compounds are known to those skilled in the art and are described for example in U.S. Pat. Nos. 9,737,485, 10,507,182, and 10,722,467. In such methods, the agent to be encapsulated is dissolved in a loading solvent and the resulting solution is added to a suspension of liposomes comprising a loading aid resulting in a mixture comprising the agent to be loaded as an amorphous solid, or is provided as an amorphous solid form and added to a suspension of liposomes comprising a loading aid. Other preferred methods of encapsulation of poorly water-soluble compounds are described in Li et al., Pharmaceutics (2019), 11, 465.

Passive and active methods of entrapment may also be coupled in order to prepare a liposome formulation containing more than one encapsulated agent.

Purification of Liposomes

In one aspect, provided is a method of preparing a purified liposomal composition comprising:

liposomes comprising:

(a) a lipid bilayer;

(b) an internal medium; and (c) a therapeutic agent encapsulated in the internal medium of the liposomes, wherein the therapeutic agent has low water solubility and can be protonated to a protonated form;

said method comprising:

(i) providing a crude liposomal composition; and (ii) purifying the crude liposomal composition with an acidified aqueous solution.

In some embodiments, the acidified aqueous solution comprises a sugar. In some embodiments, the acidified aqueous solution comprises dextrose or sucrose. In some embodiments, the acidified aqueous solution comprises dextrose. In some embodiments, the acidified aqueous solution comprises between about 5 wt % and about 20 wt % dextrose. In some embodiments, the acidified aqueous solution comprises 5 wt % dextrose. In some embodiments, the acidified aqueous solution comprises 9 wt % dextrose. In some embodiments, the acidified aqueous solution comprises sucrose. In some embodiments, the acidified aqueous solution comprises between about 5 wt % and about 20 wt % sucrose. In some embodiments, the acidified aqueous solution comprises 5 wt % sucrose. In some embodiments, the acidified aqueous solution comprises 9 wt % sucrose.

In some embodiments, the acidified aqueous solution comprises an inorganic acid, such as a mineral acid. In some embodiments, the acidified aqueous solution comprises hydrochloric acid. In some embodiments, the acidified aqueous solution comprises between about 1 mM and 100 mM hydrochloric acid. In some embodiments, the acidified aqueous solution comprises an organic acid, such as a sulfonic acid or a carboxylic acid. In some embodiments, the acidified aqueous solution comprises methanesulfonic acid. In some embodiments, the acidified aqueous solution comprises between about 1 mM and 100 mM organic acid. In some embodiments, the acidified aqueous solution comprises between about 1 mM and 100 mM methanesulfonic acid. In some embodiments, the acidified aqueous solution comprises about 1 mM methanesulfonic acid. In some embodiments, the acidified aqueous solution comprises about 5 mM methanesulfonic acid. In some embodiments, the acidified aqueous solution comprises about 10 mM methanesulfonic acid. In some embodiments, the acidified aqueous solution comprises acetic acid. In some embodiments, the acidified aqueous solution comprises between about 1 mM and 100 mM acetic acid. In some embodiments, the acidified aqueous solution comprises about 25 mM acetic acid. In some embodiments, the acidified aqueous solution comprises sodium acetate. In some embodiments, the acidified aqueous solution comprises between about 1 mM and 100 mM sodium acetate. In some embodiments, the acidified aqueous solution comprises about 25 mM sodium acetate. In some embodiments, the acidified aqueous solution comprises acetate. In some embodiments, the acidified aqueous solution comprises between about 1 mM and 100 mM acetate. In some embodiments, the acidified aqueous solution comprises about 25 mM acetate.

In some embodiments, the acidified aqueous solution comprises a salt. In some embodiments, the acidified aqueous solution comprises a salt, wherein the salt comprises an alkali metal or an alkaline-earth metal. In some embodiments, the acidified aqueous solution comprises a sodium salt. In some embodiments, the acidified aqueous solution comprises NaF, NaCl, NaBr, or NaI. In some embodiments, the acidified aqueous solution comprises NaCl. In some embodiments, the acidified aqueous solution comprises a potassium salt. In some embodiments, the acidified aqueous solution comprises a lithium salt. In some embodiments, the acidified aqueous solution comprises a magnesium salt. In some embodiments, the acidified aqueous solution comprises a calcium salt.

In some embodiments, the pH of the acidified aqueous solution is between about 1 and about 6. In some embodiments, the pH of the acidified aqueous solution is between about 2 and about 5. In some embodiments, the pH of the acidified aqueous solution is about 2.3. In some embodiments, the pH of the acidified aqueous solution is about 3. In some embodiments, the pH of the acidified aqueous solution is about 4.

In some embodiments, purifying the crude liposomal composition with an acidified aqueous solution is performed multiple times. In some embodiments, purifying the crude liposomal composition with an acidified aqueous solution is performed between 8 and 24 times. In some embodiments, purifying the crude liposomal composition with an acidified aqueous solution is performed between 8 and 12 times. In some embodiments, purifying the crude liposomal composition with an acidified aqueous solution is performed between 12 and 24 times. In some embodiments, purifying the crude liposomal composition with an acidified aqueous solution is performed at least 8 times. In some embodiments, purifying the crude liposomal composition with an acidified aqueous solution is performed 8 times. In some embodiments, purifying the crude liposomal composition with an acidified aqueous solution is performed at least 12 times. In some embodiments, purifying the crude liposomal composition with an acidified aqueous solution is performed 12 times.

Methods of Use

Also provided is a method for delivering a therapeutically effective amount of a therapeutic agent comprising administering to a subject a liposomal composition prepared as described herein, comprising one or more liposomes, wherein each of the one or more liposomes comprises:

(a) a lipid bilayer comprising a first lipid and a first sterol;
(b) an internal medium comprising a first loading aid and a first solvent; and
(c) a therapeutic agent encapsulated in the internal medium of said liposome.

Compositions of the present invention may be administered to warm-blooded animals, including humans as well as to domestic and/or avian species. In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs. For treatment of human ailments, a qualified physician will determine how the compositions of the present invention should be utilized with respect to dose, schedule and route of administration using established protocols. Such applications may also utilize dose escalation should agents encapsulated in delivery vehicle compositions of the present invention exhibit reduced toxicity to healthy tissues of the subject.

Preferably, the pharmaceutical compositions of the present invention are administered parenterally, i.e., intraarterially, intravenously, intraperitoneally, subcutaneously, or intramuscularly. More preferably, the pharmaceutical compositions are administered intravenously or intraperitoneally by a bolus injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

In other methods, the pharmaceutical preparations of the present invention can be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

Pharmaceutical compositions comprising delivery vehicles of the invention are prepared according to standard techniques and may comprise water, buffered water, 0.9% saline, 0.3% glycine, 5% dextrose and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

Preferably, the pharmaceutical compositions of the present invention are administered intravenously. Dosage for the delivery vehicle formulations will depend on the ratio of drug to lipid and the administrating physician's opinion based on age, weight, and condition of the patient.

In addition to pharmaceutical compositions, suitable formulations for veterinary use may be prepared and administered in a manner suitable to the subject. Preferred veterinary subjects include mammalian species, for example, non-human primates, dogs, cats, cattle, horses, sheep, and domesticated fowl. Subjects may also include laboratory animals, for example, in particular, rats, rabbits, mice, and guinea pigs.

In the instance where a single composition containing more than one active agent is included, the above procedures are followed per se. Where the agents are administered in separate delivery vehicle compositions, the administration should be timed in such a manner that the desired ratio is maintained. Typically, this can accomplished by simultaneously administering the compositions in the calculated proportions.

Kits

The therapeutic agents in the invention compositions may be formulated separately in individual compositions wherein each therapeutic agent is stably associated with appropriate delivery vehicles. These compositions can be administered separately to subjects as long as the pharmacokinetics of the delivery vehicles are coordinated so that the ratio of therapeutic agents administered is maintained at the target for treatment. Thus, it is useful to construct kits which include, in separate containers, a first composition comprising delivery vehicles stably associated with at least a first therapeutic agent and, in a second container, a second composition comprising delivery vehicles stably associated with at least one second therapeutic agent. The containers can then be packaged into the kit.

The kit will also include instructions as to the mode of administration of the compositions to a subject, at least including a description of the ratio of amounts of each composition to be administered. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration; for example, the kit might contain the appropriate amounts of each composition in separate syringes. Formulations which comprise the pre-formulated correct ratio of therapeutic agents may also be packaged in this way so that the formulation is administered directly from a syringe prepackaged in the kit.

EXAMPLES

The following examples illustrate some embodiments of the invention. The examples and preparations that follow are provided to enable those skilled in the art to more clearly understand and to practice these and other embodiments of the present invention. They should not be considered as limiting the scope of the invention, but merely as being illustrative and representative thereof.

Example 1A. General Procedure A for Liposome Formulation

Liposomes containing drug compounds were generated by remotely loading drug compounds into DSPC/Cholesterol/PEG-DSG liposomes containing ammonium sulfate (AS), ammonium sucrose octasulfate (NH4SOS), triethylammonium sucrose octasulfate (TEASOS), or triethanolammonium sucrose octasulfate (TEA(OH)SOS), or ammonium citrate as a loading aid.

A. Preparation of Loading Aids 250 mM ammonium sulfate loading aid solution was prepared by dissolving solid ammonium sulfate into deionized (DI) water to reach the target concentration of 250 mM. This gave a solution with a pH of 5.2. The solution was filtered through a 0.2 μm membrane.

300 mM ammonium citrate loading aid solution was prepared by dissolving solid ammonium dibasic citrate into DI water to reach the target concentration of 300 mM. This gave a solution with a pH of 4.9. The solution was filtered through 0.2 μm membrane.

0.5-1.0 N triethylamine-SOS loading aid solution was prepared from potassium SOS. For small batches, 5 g of potassium SOS was dissolved in 12 mL of DI water at 65° C. and filtered with a glass fiber membrane. The warm solution was then loaded to top of a Dowex column containing ~30 mL of packed 50W-X8 beads pretreated with 3 M HCl and thoroughly washed with DI water. After depletion, DI water was loaded to elute the SOS solution. Through a flow conductivity meter connected the bottom of the column, a fraction of eluate solution was collected with a conductivity greater than 150 mS/cm. The resulting H—SOS solution was immediately titrated with triethylamine until the pH reached 6.5±0.5. The trimethylamine-SOS solution was filtered with a 0.2 μm membrane. The SOS concentration was determined by sulfur elemental analysis with ICP-OES (5800 VDV, Agilent). The filtered solution was stored at 4° C.

0.5-1.0 N ammonium SOS loading aid solution was prepared in the same way as above, except that the eluted H—SOS solution was immediately titrated with concentrated ammonia to reach the target pH of 6.5±0.5.

0.5-1.0 N triethanolamine SOS loading aid solution was prepared in the same way as above except that the eluted H—SOS solution was immediately titrated with triethanolamine to reach the target pH of 6.5±0.5.

The preparation of all SOS solutions can be scaled-up 25-100 fold proportionally.

B. Lipid Foam Preparation and Liposome Extrusion

DSPC, Cholesterol, and a polymer-conjugated lipid were weighed and dissolved in chloroform in a sealed glass vial or bottle.

Upon forming the viscous chloroform solution of concentrated lipids, vacuum was applied to generate lipid foams in seconds. The chloroform was thoroughly removed by placing the lipid foam in a Buchi vacuum pump system (V-512, Buchi) with heating or overnight at ambient temperature. The dried foam was stored at −20° C. if not used immediately.

The lipid foam was hydrated by adding an aqueous solution of loading aid pre-heated to 65° C. in a water bath. The heated solution was added to the lipid foam. Multilamellar vesicles (MLVs) were created by vortexing for cycles of 20-30 seconds, followed by heating for 2-3 minutes.

Depending on the loading aid used, the 250 mM ammonium sulfate can be substituted for 300 mM ammonium citrate, or 0.5-1 N triethylamine-SOS, or 0.5-1 N Ammonium-SOS or 0.5-1 N triethanolamine-SOS.

The MLVs were extruded once through a 200 nm PCTE (polycarbonate track etched) membrane at 20-100 psi using a 10 mL jacketed liposome extruder (LIPEX®) maintained at 65° C. The resulting MLVs were then extruded 7 times through a 100 nm PCTE membrane at 50-200 psi using a 10 mL jacketed liposome extruder maintained at 65° C. If liposome formulations require handling and storage at low temperatures, liposomes can be extruded with loading aid and sucrose as cryoprotectant.

For small scale volumes (i.e. <20 ml), extruded liposomes containing 250 mM ammonium sulphate or 300 mM ammonium citrate were buffer exchanged into 9% w/v dextrose by loading in Sephadex G25 columns (PD-10 Column, Cytiva) at a ratio of 1 mL/8.3 mL bed volume and collecting the liposome eluate fraction with a conductivity<50 μS/cm, thereby removing any unencapsulated loading aid.

For small scale volumes, extruded liposomes containing 0.5-1 N triethylamine-SOS, or 0.5-1 N ammonium-SOS or 0.5-1 N triethanolamine-SOS were buffer exchanged into 9-18% w/v dextrose (depending on the normality of the loading aid to balance osmotic pressure) by loading in Sepharose CL4B columns at a ratio of 1 mL/10 mL bed volume and collecting the liposome eluate fraction with a conductivity<20 μS/cm, thereby removing any unencapsulated loading aid.

For larger scale volumes, extruded liposomes containing 250 mM ammonium sulphate, or 300 mM ammonium citrate, or 0.5-1 N triethylamine-SOS, or 0.5-1 N Ammonium-SOS or 0.5-1 N triethanolamine-SOS were buffer exchanged with 18 volume exchanges of 9-18% w/v dextrose using tangential flow filtration (Sartorius Slice 200) with a 100 kDa MWCO Hydrosart PES membrane.

C. Encapsulation of Drug Compounds into Liposomes

Drug compounds were dissolved in DMSO at a concentration of 20-100 mg/mL and added dropwise to the prepared liposomes under stirring and heated to 65° C. such that the final drug concentration in the solution was in the range of 0.2 to 6.0 mg/mL and the final D/L ratio was in the range 0.1 to 0.8 mol/mol. The final organic solvent concentration was between 2 to 30%.

The sample was incubated under constant stirring at 65° C. or room temperature to facilitate loading of the drug into the liposomes. After loading, the sample was cooled on an ice bath.

D. Purification of Drug-loaded Liposomes

Purification of the formulations were carried using tangential flow filtration (Slice 200, Sartorius) equipped with 100-300 k MWCO (Hydrosart, Sartorius) PES membranes. The formulation was first concentrated to 50 mL, than purified with 12-24 volume exchanges of acidified (0.01 M HCl or $MeSO_3H$) dextrose of similar concentration as during the loading procedure in order to remove unencapsulated drug. Thereafter, the formulation was purified with another 12 volume exchanges of 5% dextrose. Alternatively, if low temperature storage of the liposome formulation is required, sucrose may be used instead of dextrose. Finally, the formulation was concentrated to 10-20 mg/ml lipids, collected and filtered through a 0.22 μm PES syringe filter.

Example 1B. General Procedure B for Liposome Formulation

Liposomes containing drug compounds were generated by remotely loading drug compounds into DSPC/Cholesterol/PEG-DSG liposomes containing ammonium sulfate (AS), ammonium sucrose octasulfate (NH4SOS), triethylammonium sucrose octasulfate (TEASOS), or triethanolammonium sucrose octasulfate (TEA(OH)SOS), or ammonium citrate as a loading aid.

A. Preparation of Loading Aids 250 mM ammonium sulfate loading aid solution was prepared by dissolving solid ammonium sulfate into deionized (DI) water to reach the target concentration of 250 mM. This gave a solution with a pH of 5.2. The solution was filtered through a 0.2 μm membrane.

300 mM ammonium citrate loading aid solution was prepared by dissolving solid ammonium dibasic citrate into DI water to reach the target concentration of 300 mM. This gave a solution with a pH of 4.9. The solution was filtered through 0.2 μm membrane.

0.5-1.0 N triethylamine-SOS loading aid solution was prepared from potassium SOS. For small batches, 5 g of potassium SOS was dissolved in 12 mL of DI water at 65° C. and filtered with a glass fiber membrane. The warm solution was then loaded to top of a Dowex column containing ~30 mL of packed 50W-X8 beads pretreated with 3 M HCl and thoroughly washed with DI water. After depletion, DI water was loaded to elute the SOS solution. Through a flow conductivity meter connected the bottom of the column, a fraction of eluate solution was collected with a conductivity greater than 150 mS/cm. The resulting H—SOS solution was immediately titrated with triethylamine until the pH reached 6.5±0.5. The trimethylamine-SOS solution was filtered with a 0.2 μm membrane. The SOS concentration was determined by sulfur elemental analysis with ICP-OES (5800 VDV, Agilent). The filtered solution was stored at 4° C.

0.5-1.0 N ammonium SOS loading aid solution was prepared in the same way as above, except that the eluted H—SOS solution was immediately titrated with concentrated ammonia to reach the target pH of 6.5±0.5.

0.5-1.0 N triethanolamine SOS loading aid solution was prepared in the same way as above except that the eluted H—SOS solution was immediately titrated with triethanolamine to reach the target pH of 6.5±0.5.

The preparation of all SOS solutions can be scaled-up 25-100 fold proportionally.

B. Lipid Foam Preparation and Liposome Extrusion

DSPC, Cholesterol, and a polymer-conjugated lipid were weighed and dissolved in chloroform in a sealed glass vial or bottle.

Upon forming the viscous chloroform solution of concentrated lipids, vacuum was applied to generate lipid foams in seconds. The chloroform was thoroughly removed by placing the lipid foam in a Buchi vacuum pump system (V-512, Buchi) with heating or overnight at ambient temperature. The dried foam was stored at −20° C. if not used immediately.

The lipid foam was hydrated by adding an aqueous solution of loading aid pre-heated to 65° C. in a water bath. The heated solution was added to the lipid foam. Multilamellar vesicles (MLVs) were created by vortexing for cycles of 20-30 seconds, followed by heating for 2-3 minutes.

Depending on the loading aid used, the 250 mM ammonium sulfate can be substituted for 300 mM ammonium citrate, or 0.5-1 N triethylamine-SOS, or 0.5-1 N Ammonium-SOS or 0.5-1 N triethanolamine-SOS.

The MLVs were extruded once through a 200 nm PCTE (polycarbonate track etched) membrane at 20-100 psi using a 10 mL jacketed liposome extruder (LIPEX®) maintained at 65° C. The resulting MLVs were then extruded 7 times through a 100 nm PCTE membrane at 50-200 psi using a 10 mL jacketed liposome extruder maintained at 65° C. If liposome formulations require handling and storage at low temperatures, liposomes can be extruded with loading aid and sucrose as cryoprotectant.

For small scale volumes (i.e. <20 ml), extruded liposomes containing 250 mM ammonium sulphate or 300 mM ammonium citrate were buffer exchanged into 9% w/v dextrose by loading in Sephadex G25 columns (PD-10 Column, Cytiva) at a ratio of 1 mL/8.3 mL bed volume and collecting the liposome eluate fraction with a conductivity<50 μS/cm, thereby removing any unencapsulated loading aid.

For small scale volumes, extruded liposomes containing 0.5-1 N triethylamine-SOS, or 0.5-1 N ammonium-SOS or 0.5-1 N triethanolamine-SOS were buffer exchanged into 9-18% w/v dextrose (depending on the normality of the loading aid to balance osmotic pressure) by loading in Sepharose CL4B columns at a ratio of 1 mL/10 mL bed volume and collecting the liposome eluate fraction with a conductivity<20 μS/cm, thereby removing any unencapsulated loading aid.

For larger scale volumes, extruded liposomes containing 250 mM ammonium sulphate, or 300 mM ammonium citrate, or 0.5-1 N triethylamine-SOS, or 0.5-1 N Ammonium-SOS or 0.5-1 N triethanolamine-SOS were buffer exchanged with 10-18 volume exchanges of 9-18% w/v dextrose using tangential flow filtration (Sartorius Slice 200) with a 100 kDa MWCO Hydrosart PES membrane. The final conductivity of the purified liposomes prepared according to this process is between about 10 and 200 μS/cm. Ideally, the final conductivity is between about 20 and 100 μS/cm, or between about 50 and 100 μS/cm.

C. Encapsulation of Drug Compounds into Liposomes

Drug compounds were dissolved in DMSO at a concentration of 20-100 mg/mL and added dropwise to the prepared liposomes under stirring and heated to 65° C. such that the final drug concentration in the solution was in the range of 0.2 to 6.0 mg/mL and the final D/L ratio was in the range 0.1 to 0.8 mol/mol. The final organic solvent concentration was between 2 to 30%.

The sample was incubated under constant stirring at 65° C. or room temperature to facilitate loading of the drug into the liposomes. After loading, the sample was cooled on an ice bath.

D. Purification of Drug-loaded Liposomes

Purification of the formulations were carried using tangential flow filtration (Slice 200, Sartorius) equipped with 100-300 k MWCO (Hydrosart, Sartorius) PES membranes. The formulation was first concentrated to 5 or 10 mL, then purified with 12 volume exchanges of acidified sugar solution in order to remove unencapsulated drug. The acidified sugar solution contained 5 wt % dextrose, 9 wt % dextrose, or 9 wt % sucrose. The acid in the acidified sugar solution was methanesulfonic acid. The concentration of methanesulfonic acid in the acidified sugar solution was 1 mM, 5 mM, or 10 mM. Alternatively, the acidified sugar solution contained 25 mM sodium acetate at a pH of about 4.0. Thereafter, the formulation was purified with another 12 volume exchanges of 5% dextrose or 9% sucrose. Finally, the formulation was concentrated to 10-20 mg/ml lipids, collected and filtered through a 0.22 μm PES syringe filter.

Liposomes prepared according to this procedure could be characterized by transmission electron microscopy (TEM), among other standard methods in the fields of nanoparticles and liposomal drug delivery.

Example 1C. General Procedure for Purifying Liposomal Formulations

Purification of the formulations is carried using tangential flow filtration (Slice 200, Sartorius) equipped with 100-300 k MWCO (Hydrosart, Sartorius) PES membranes. The formulation is first concentrated, then purified with 12-24 volume exchanges of acidified aqueous solution of similar concentration as during the loading procedure in order to remove unencapsulated drug. The acidified aqueous solution is dextrose or sucrose. The concentration of sugar in the acidified aqueous solution is between about 5 wt % and 20 wt %. The acid in the acidified aqueous solution is hydrochloric acid or methanesulfonic acid. The concentration of hydrochloric acid or methanesulfonic acid in the acidified aqueous solution is between about 1 mM and 100 mM. The acidified aqueous solution can alternatively contain sodium acetate at a pH of about 4.0. The concentration of sodium acetate in the acidified aqueous solution is between about 5 mM and 100 mM. Thereafter, the formulation is purified with another 8-24 volume exchanges of aqueous solution. Finally, the formulation is concentrated to 10-20 mg/ml lipids, collected and filtered through a 0.22 μm PES syringe filter.

Liposomes prepared according to this procedure are characterized by transmission electron microscopy (TEM), among other standard methods in the fields of nanoparticles and liposomal drug delivery.

Example 2. Formulation of Compound 9 into Liposomes

Liposomes containing Compound 9 were generated by remotely loading into DSPC/Cholesterol/PEG-DSG (3:2:0.3 mole ratio) liposomes containing ammonium sulfate (AS), ammonium sucrose octasulfate (NH4SOS), triethylammonium sucrose octasulfate (TEASOS), triethanolammonium sucrose octasulfate (TEA(OH)SOS), or ammonium citrate as a loading aid.

A. Preparation of Loading Aids

Loading aid solutions were prepared as described in Example 1A.

B. Lipid Foam Preparation and Liposome Extrusion

DSPC/Cholesterol/PEG-DSG (3:2:0.3 mole ratio) was weighed and dissolved in chloroform at a concentration of 1 g lipid/mL of chloroform using heat at ~60° C. in a sealed glass vial or bottle.

Upon forming the viscous chloroform solution of concentrated lipids, vacuum was applied to generate lipids foam in seconds. The chloroform was thoroughly removed by placing the lipid foam in a Buchi vacuum pump system (V-512, Buchi) for either 0.5 hour with heating or overnight at ambient temperature. The dried foam was stored at −20° C. if not used immediately.

The lipid foam was hydrated by adding an aqueous solution of 250 mM ammonium sulphate pre-heated to 65° C. in a water bath. The heated solution was added to the lipid foam at a concentration of 50 mg lipid/mL of 250 mM ammonium sulphate solution. Multilamellar vesicles (MLVs) were created by vortexing for cycles of 20-30 seconds, followed by heating for 2-3 minutes.

Depending on the loading aid used, the 250 mM ammonium sulphate can be substituted for 300 mM ammonium citrate, or 0.5-1 N triethylamine-SOS, or 0.5-1 N Ammonium-SOS or 0.5-1 N triethanolamine-SOS.

The MLVs were extruded once through a 200 nm PCTE (polycarbonate track etched) membrane at 20-100 psi using a 10 mL jacketed liposome extruder (LIPEX®) maintained at 65° C. The resulting MLVs were then extruded 7 times through a 100 nm PCTE membrane at 50-200 psi using a 10 mL jacketed liposome extruder maintained at 65° C. If liposome formulations require handling and storage at low temperatures, liposomes can be extruded with loading aid and sucrose as cryoprotectant.

The extruded liposomes had a mean hydrodynamic diameter of 110 nm +/−20 nm as determined by dynamic light scattering (Malvern Nano ZS) using 0.9% saline as the diluent.

For small scale volumes (i.e. <20 ml), extruded liposomes containing 250 mM ammonium sulphate or 300 mM ammonium citrate were buffer exchanged into 9% w/v dextrose by loading in Sephadex G25 columns (PD-10 Column, Cytiva) at a ratio of 1 mL/8.3 mL bed volume and collecting the liposome eluate fraction with a conductivity<50 μS/cm, thereby removing any unencapsulated loading aid.

For small scale volumes, extruded liposomes containing 0.5-1 N triethylamine-SOS, or 0.5-1 N ammonium-SOS or 0.5-1 N triethanolamine-SOS were buffer exchanged into 9-18% w/v dextrose (depending on the normality of the loading aid to balance osmotic pressure) by loading in Sepharose CL4B columns at a ratio of 1 mL/10 mL bed volume and collecting the liposome eluate fraction with a conductivity<20 μS/cm, thereby removing any unencapsulated loading aid.

For larger scale volumes, extruded liposomes containing 250 mM ammonium sulphate, or 300 mM ammonium citrate, or 0.5-1 N triethylamine-SOS, or 0.5-1 N Ammonium-SOS or 0.5-1 N triethanolamine-SOS were buffer exchanged with 18 volume exchanges of 9-18% w/v dextrose using tangential flow filtration (Sartorius Slice 200) with a 100 kDa MWCO Hydrosart PES membrane.

C. Encapsulation of Compound 9 into Liposomes

For 250 mM ammonium sulphate as a loading aid, Compound 9 was dissolved in DMSO at a concentration of 20-100 mg/mL and added dropwise to the prepared liposomes under stirring and heated to 65° C. such that the final drug concentration in the solution was in the range of 0.2 to 0.8 mg/mL and the final D/L ratio was in the range 0.1 to 0.8 mol/mol. The final DMSO concentration was between 2 to 30%.

The sample was incubated under constant stirring at 65° C. for 45 minutes to facilitate loading of the drug into the liposomes. After loading, the sample was cooled on an ice bath.

D. Purification of Compound 9-loaded Liposomes

Purification of the formulations were carried using tangential flow filtration (Slice 200, Sartorius) equipped with 100-300 k MWCO (Hydrosart, Sartorius) PES membranes. The formulation was first concentrated to 50 mL, than purified with 12-24 volume exchanges of acidified (0.01 M HCl or $MeSO_3H$) dextrose of similar concentration as during the loading procedure in order to remove unencapsulated drug. Thereafter, the formulation was purified with another 12 volume exchanges of 5% dextrose. Alternatively, if low temperature storage of the liposome formulation is required, sucrose may be used instead of dextrose. Finally, the formulation was concentrated to 10-20 mg/ml lipids, collected and filtered through a 0.22 μm PES syringe filter.

Example 3. Drug and Lipid Assays

Formulations of liposomes containing various drugs were prepared as described in Examples 1A. Lipid contents were analyzed using phospholipids C and cholesterol assay kits (Fujifilm) and a UV spectrometer (Cytation 5, BioTek Instruments Inc.).

To determine the drug content, the drug-loaded liposomes were first solubilized in a solubilizing mixture containing 70% ethanol and 100 mM HCl. A calibration curve was prepared with Compound 9 powder and the same solubilizing mixture. The drug was detected using a UV spectrometer (Cytation 5, BioTek Instruments Inc.) measuring absorbance at 310 nm.

The drug yield is the drug recovery after purification of the formulation (i.e. without taking the lipids into consideration). It was calculated as follows:

Drug yield (%)=Drug concentration final formulation/drug concentration in the control*100

The control was the same formulation but without purification (i.e. recovery is 100%).

The encapsulation efficiency (EE) is calculated as follows:

EE (%)=Drug-to-Lipid ratio in final formulation/Drug-to-Lipid ratio in the control*100

For example, if the Drug-to-Lipid ratio is to be 0.10 (control) and the final formulation presents a Drug-to-Lipid ratio of 0.05 after purification, EE will be 50% (0.05/0.1*100).

The composition of these formulations is provided in Table 1. Characterization of these lipids (e.g., encapsulation efficiency, liposome size) is presented below in Table 2.

TABLE 1

| Formulations of liposomes. | | | | | | | |
|---|---|---|---|---|---|---|---|
| Liposome | Phospholipid (mol %) | Sterol (mol %) | PCL (mol %) | Loading Aid | External Buffer (% w/v) | Loading Temp. (° C.) | DMSO (mol %) |
| 1a | DSPC (57%) | Chol (38%) | PEGylated (5.6%) | AS (250 mM) | Dextrose (9%) | 65 | 10 |
| 1b | DSPC (57%) | Chol (38%) | PEGylated (5.6%) | AS (250 mM) | Dextrose (9%) | 65 | 4 |
| 2a | DSPC (57%) | Chol (38%) | PEGylated (5.6%) | AS (250 mM) | Dextrose (9%) | 65 | 20 |
| 2b | DSPC (57%) | Chol (38%) | PEGylated (5.6%) | KSOS (0.43N)/ Na-Citrate (300 mM) | 10 mM MES/ Dextrose (9%) | 65 | 0 |
| 2c | DSPC (57%) | Chol (38%) | PEGylated (5.6%) | KSOS (0.43N)/ Na-Citrate (300 mM) | 10 mM $MeSO_3H$/ Dextrose (9%) | 65 | 0 |
| 3a | DSPC (57%) | Chol (38%) | PEGylated (5.6%) | AS (250 mM) | Dextrose (9%) | 65 | 2 |
| 3b | DSPC (57%) | Chol (38%) | PEGylated (5.6%) | TEASOS (0.5N) | Dextrose (7.5%) | 65 | 2 |
| 4a | DSPC (57%) | Chol (38%) | PEGylated (5.6%) | TEASOS (1.1N) | Dextrose (18%) | 65 | 4 |
| 5a | DSPC (57%) | Chol (38%) | PEGylated (5.6%) | TEASOS (1.1N) | Dextrose (18%) | 65 | 2 |
| 5b | DSPC (57%) | Chol (38%) | PEGylated (5.6%) | AS (500 mM) | Dextrose (18%) | 65 | 2 |

DSPC = Distearoylphosphatidylglycerol.
PCL = polymer-conjugated lipid.
Chol = Cholesterol.
PEGylated = 1,2-distearoyl-rac-glycero-3-methoxypoly(ethylene glycol-2000) (also known as DSG-PEG2000 and PEG(2000)-distearoylglycerol).
AS = ammonium sulfate.
KSOS = potassium sucrose octasulfate.
MES = 2-(N-morpholino)ethanesulfonic acid.
TEASOS = triethylammonium sucrose octasulfate.
$MeSO_3H$ = methanesulfonic acid.

TABLE 2

| Characterization of drug-loaded liposomes. | | | | | | |
|---|---|---|---|---|---|---|
| | | | Drug | | Liposome size | |
| Liposome | Drug | [D] (mg/mL) | Yield (%) | EE (%) | Z-ave (nm) | PDI |
| 1a | Compound 2 | 0.31 | 81 | 126 | 136 | 0.05 |
| 1b | Compound 2 | 0.26 | 65 | 77 | 132 | 0.06 |
| 2a | Compound 9 | 1.42 | 95 | 80 | 139 | 0.12 |
| 2b | Compound 9 | 0.23 | N.D. | 65 | 210 | 0.35 |
| 2c | Compound 9 | 1.29 | N.D. | 73 | 182 | 0.27 |
| 3a | Compound 7 | 0.25 | 68 | 93 | 151 | 0.05 |
| 3b | Compound 7 | 0.26 | 69 | 97 | 131 | 0.06 |
| 4a | Venetoclax | 0.60 | 76 | 81 | 176 | 0.22 |
| 5a | Navitoclax | 0.28 | 68 | 85 | 135 | 0.09 |
| 5b | Navitoclax | 0.16 | 38 | 28 | 145 | 0.10 |

EE = encapsulation efficiency.
PDI = polydispersity index.
Z-ave = average diameter.
N.D. = not determined.

Example 4. Formulations and Pharmacokinetic Characterization of Drug-Loaded Liposomes Experimental Design Female B6D2F1/J mice were purchased from Jackson Laboratory and acclimated 7 days prior to study start. Mice were caged in autoclaved Allentown ventilated caging at a capacity of 3 animals/cage during the course of the experiment. Cages were changed bi-weekly. Environmental enrichment that was supplied for cages were Nestlets from Ancare, transparent tinted polycarbonate Mouse Igloos from Bio-Serv on Envigo 7097 ¼" corn cob bedding. All enrichment was added to the cage prior to the cages being autoclaved. Mice were fed Envigo Teklad Global Rodent Diet 2018. The rodent food was kept in the hoppers of the wire lids and was changed bi-weekly. Reverse osmosis water was supplied through Avidity Science automatic watering valves at a flow rate of 25-50 ml/min. Environmental control of the lights and monitoring of temperature, humidity and airflow was done by WatchDog. Light cycles in the animal holding rooms was set for 12 hours on and 12 hours off. Temperature, humidity and airflow were maintained and controlled by BCCRC facilities.

Storage of Test/Control Articles

All Test/Control Articles (TAs/CAs) were provided as ready to inject and stored at 2-8° C.

Dose Administration

Mice were injected with the required volume to administer the prescribed dose (10 mg/kg) to the animals based on individual mouse weights using a 28G needle. The injection volume was 200 μL/20 g mouse. The mice were briefly (less than 30 sec.) restrained during i.v. injections. Dilation of the vein was achieved by holding the animals under a heat lamp for a period of between 1-2 minutes (current revision of SOP-AF-018).

Data Collection

Pharmacokinetic Sampling

Mice were individually weighed. Mice were injected with the Test Article/Control Article and blood were collected as per the study grouping table. For blood collection, mice were terminated by isoflurane followed by $CO_2$ inhalation (SOP-AF-042). Blood was collected by cardiac puncture (current revision of SOP-AF-002). For cardiac puncture, upon last breath, mice were removed from inhalation chamber and approximately 500 μL of blood was collected by cardiac puncture with a 25 G needle and placed into the appropriate microtainer tube (K2EDTA). Plasma was separated by centrifuging samples at 1300 g for 15 minutes, then pipetted off and placed into labelled vials. The plasma was frozen at −20° C. and the remaining dosing material was stored at ca. 4° C. until samples were shipped.

Determination of Drug Plasma Concentrations

Plasma samples were diluted in acidified methanol and vortexed vigorously. The plasma/methanol samples were then centrifuged at 10000 rcf for 10 min at 8° C. The supernatant was injected onto a Phenomenex Synergi Fusion-RP 2.5 μm 50×3 mm column running a gradient with 10 mM ammonium acetate buffer and acetonitrile. Drug was detected using a diode array detector at wavelength of 300 nm. The plasma drug concentrations were calculated against a linear calibration curve range from 1-40 μg/mL.

Liposome Formulations

All liposomes used in the pharmacokinetic studies described herein comprised DPSC/Cholesterol/PEGylated (56/38/5.6 mol %) and were prepared according to Examples 1A, 1B, and 2.

TABLE 3

Formulations of liposomes used in pharmacokinetic (PK) studies.

| Liposome | Drug | PCL (mol %) | Loading Aid | External Buffer (% w/v) | Loading Temp. (° C.) | DMSO (mol %) |
|---|---|---|---|---|---|---|
| 7a | Compound 9 | PEGylated (5.6%) | AS (250 mM) | Dextrose (9%) | 65 | 2 |
| 7b | Compound 9 | PEGylated (5.6%) | AS (500 mM) | Dextrose (17%) | 65 | 2 |
| 7c | Compound 9 | PEGylated (5.6%) | $NH_4$SOS (1.1N) | Dextrose (18%) | 65 | 2 |
| 7d | Compound 9 | PEGylated (5.6%) | TEASOS (1.1N) | Dextrose (18%) | 65 | 2 |
| 8a | Compound 2 | PEGylated (5.6%) | AS (250 mM) | Dextrose (9%) | 65 | 10 |
| 8b | Compound 2 | PEGylated (5.6%) | AS (250 mM) | Dextrose (9%) | 65 | 2 |
| 8c | Compound 2 | PEGylated (5.6%) | AS (500 mM) | Dextrose (17%) | 65 | 2 |
| 9a | Compound 7 | PEGylated (5.6%) | AS (500 mM) | Dextrose (18%) | 65 | 2 |

PEGylated = PEG(2000)-distearoylglycerol.
AS = ammonium sulfate.
TEASOS = triethylammonium sucrose octasulfate.
$NH_4$SOS = ammonium sucrose octasulfate.

TABLE 4

Characterization of drug-loaded liposomes.

| Liposome | EE (%) | Liposome size Z-ave (nm) | PDI | $T_{1/2}$ (h) |
|---|---|---|---|---|
| 7a | 37.7 | 127 | 0.04 | 18 |
| 7b | 69.7 | 125 | 0.02 | 17 |
| 7c | 94.5 | 133 | 0.08 | 9.5 |
| 7d | 91.2 | 128 | 0.05 | 10 |
| 8a | 92.2 | 137 | 0.06 | 14.4 |
| 8b | 39.9 | 124 | 0.06 | 15.8 |
| 8c | 55.7 | 118 | 0.04 | 18 |
| 9a | 59.0 | 136 | 0.01 | 17.5 |

D/L ratio = drug/phospholipid ratio.
EE = encapsulation efficiency.
PDI = polydispersity index.
Z-ave = average diameter.
N.D. = not determined.

Example 5. Determination of Plasma Stability of Compound 2 Liposome Formulations Plasma stability was determined by measuring the concentration of Compound 2 at various time points in plasma collected as described in Example 4. All liposome formulations comprised DSPC/Cholesterol/PEGylated (56/38/5.6 mol %) as described in Examples 1A, 1B, and 2. Formulations 1-4 were prepared using 250 mM AS as the loading aid. Formulation 5 was prepared using 500 mM AS as the loading aid. Compound 2 was loaded into the liposomes of formulations 1, 4, and 5 using 2% DMSO. Compound 2 was loaded into the liposomes of formulations 2 and 3 using 10% DMSO.

FIG. 1A shows the evolution of normalized plasma concentration of Compound 2 over time using various liposomal formulations compared to using the free drug.

Figure 1B:
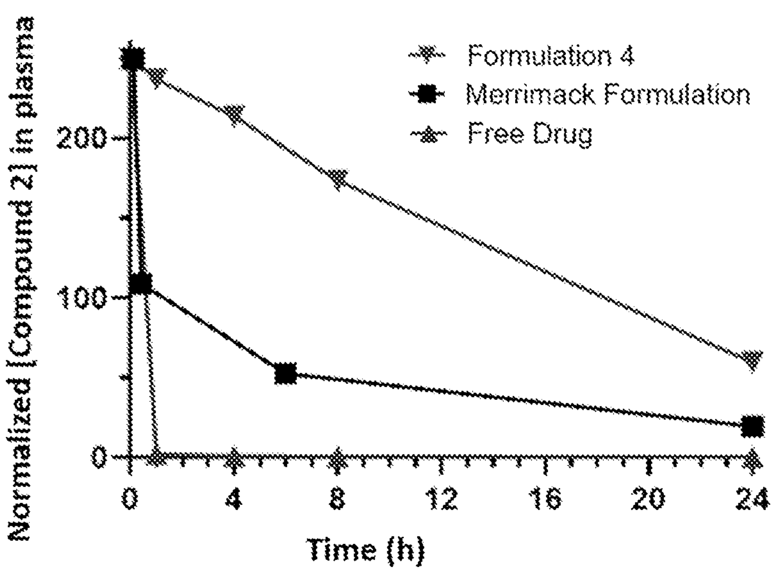
FIG. 1B shows the evolution of normalized plasma concentration of Compound 2 over time using an exemplary liposomal formulation of the present disclosure compared to using a liposomal formulation prepared according to previously published methods, and compared to using the free drug.

FIG. 1B shows the evolution of normalized plasma concentration of Compound 2 over time using an exemplary liposomal formulation of the present disclosure compared to using a liposomal formulation prepared according to previously published methods, and compared to using the free drug. The formulations labeled "Merrimack" comprised liposomes comprising DSPC/Cholesterol/PEGylated (56/38/5.6 mol %) that were loaded without DMSO using TEASOS (0.43 N) as the loading aid, according to the procedure recited in WO 2017/123616. In contrast to Formulations 1-4, the "Merrimack" formulations were not purified with an acidified aqueous solution.

Example 6. Determination of Plasma Stability of Compound 9 Liposome Formulations Plasma stability was determined by measuring the concentration of Compound 9 at various time points in plasma collected as described in Example 4. All liposome formulations comprised DSPC/Cholesterol/PEGylated (56/38/5.6 mol %) as described in Examples 1A, 1B, and 2. Formulation 1 used 250 mM AS as the loading aid. Formulation 2 used 500 mM AS as the loading aid. Formulation 3 used 0.5 N TEASOS as the loading aid. Formulation 4 used 0.5 N NH4SOS as the loading aid.

Figure 2A:
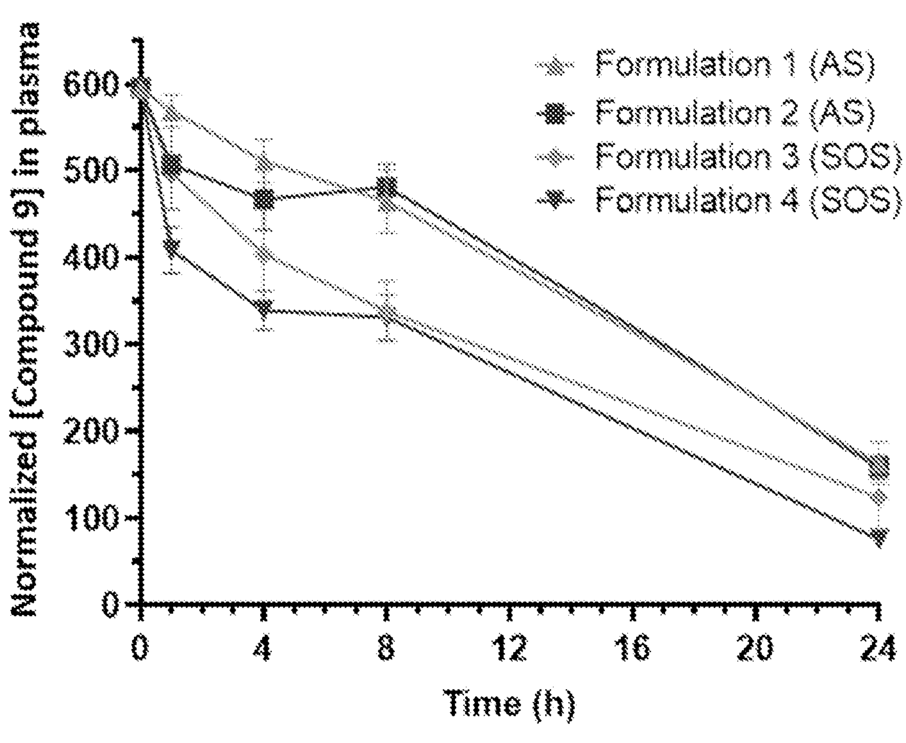
FIG. 2A shows the evolution of normalized plasma concentration of Compound 9 over time using various liposomal formulations.

FIG. 2A shows the evolution of normalized plasma concentration of Compound 9 over time using various liposomal formulations.

Figure 2B:
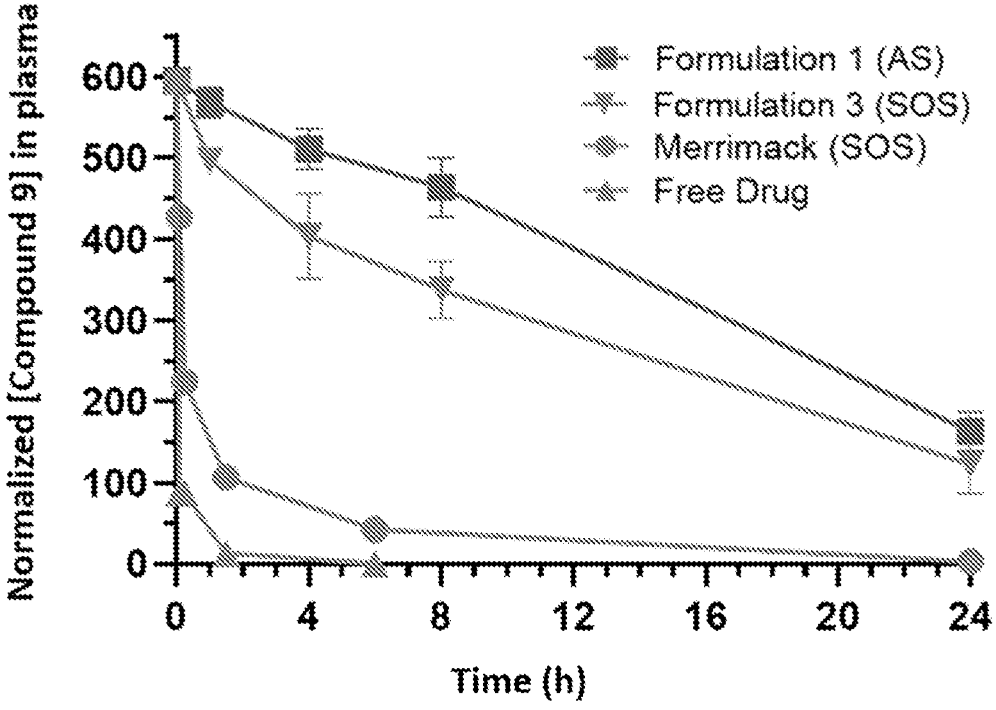
FIG. 2B shows the evolution of normalized plasma concentration of Compound 9 over time using exemplary liposomal formulations of the present disclosure compared to using a liposomal formulation prepared according to previously published methods, and compared to using the free drug.

FIG. 2B shows the evolution of normalized plasma concentration of Compound 9 over time using exemplary liposomal formulations of the present disclosure compared to using a liposomal formulation prepared according to previously published methods, and compared to using the free drug. The formulations labeled "Merrimack" comprised liposomes comprising DSPC/Cholesterol/PEGylated (56/38/5.6 mol %) that were loaded without DMSO using TEASOS (0.43 N) as the loading aid, according to the procedure recited in WO 2017/123616. In contrast to Formulations 1-4, the "Merrimack" formulations were not purified with an acidified aqueous solution.

Example 7. Removal of Free Drug During Purification with Acidified Sugar Solution A formulation of liposomes containing Compound 9 was prepared and purified as described in Examples 1A, 1B, and 2. The liposome formulation comprised DSPC/Cholesterol/PEGylated (58/40/2 mol %) and used 250 mM AS as the loading aid.

During the purification of the formulation using tangential flow filtration, the concentration of Compound 9 in the permeate was measured, as shown below in Table 7. FIG. 3 depicts the concentration of Compound 9 in the permeate vs. the washing volume.

TABLE 7

Concentration of Compound 9 in the permeate. Washing volumes are expressed as multiples of the sample volume - e.g., for 50 mL of liposome solution, 3× washing volume corresponds to 150 mL of permeate washing volume.

| Washing Volume | Concentration of Compound x (mg/mL) |
|---|---|
| 0× | N.D. |
| 1× | 0.0071 |
| 3× | 0.0159 |
| 6× | 0.0035 |
| 9× | 0.0014 |
| 12× | 0.0010 |

N.D. = not detected.

Example 8. Effect of Acid Wash Purification on the Plasma Stability of Compound 7 Liposome Formulations Plasma stability was determined by measuring the concentration of Compound 7 at various time points in plasma collected as described in Example 4. Both liposome formulations comprised DSPC/Cholesterol/PEGylated (59/39/2 mol %) as described in Examples 1A and 1B. The loading aid was 500 mM AS, and the D/L ratio was 0.4 for both liposome formulations.

The Acid Wash formulation was purified according to the procedure generally described in Example 1A and 1B, with the specific parameters described herein. Purification of the formulation was carried using tangential flow filtration (Slice 200, Sartorius) equipped with 100-300 k MWCO (Hydrosart, Sartorius) PES membranes. The formulation was first concentrated to 50 mL, then purified with 12 volume exchanges of 10 mM methanesulfonic acid in a 5 wt % aqueous dextrose solution. Thereafter, the formulation was purified with another 12 volume exchanges of 5% dextrose. Finally, the formulation was concentrated to 10-20 mg/ml lipids, collected and filtered through a 0.22 μm PES syringe filter.

The No Acid Wash formulation was purified using tangential flow filtration (Slice 200, Sartorius) equipped with 100-300 k MWCO (Hydrosart, Sartorius) PES membranes. The formulation was first concentrated to 50 mL, then purified with 12 volume exchanges of 5% dextrose, concentrated to 10-20 mg/ml lipids, collected and filtered through a 0.22 μm PES syringe filter.

Figure 4:
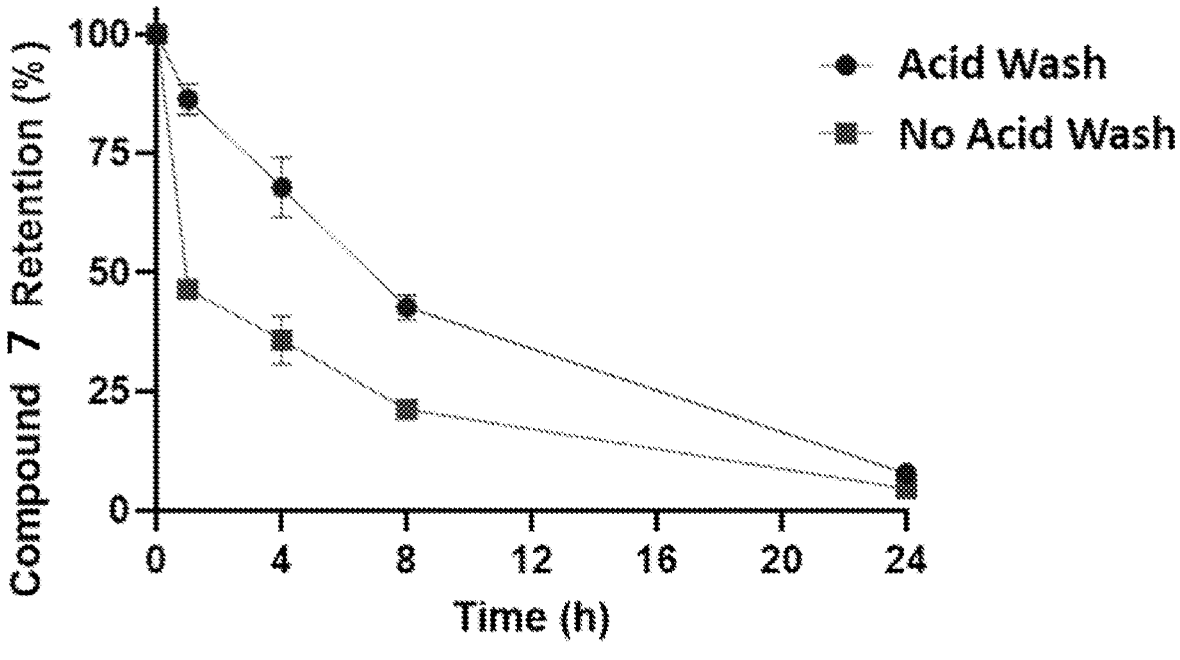
FIG. 4 shows the evolution of normalized plasma concentration of Compound 7 over time using an exemplary liposomal formulation of the present disclosure compared to using a liposomal formulation prepared according to previously published methods.

FIG. 4 shows the evolution of normalized plasma concentration of Compound 7 over time using an exemplary liposomal formulation of the present disclosure prepared with or without an acid wash step. FIG. 4 shows that liposomes in which there was an acid wash purification step exhibit superior pharmacokinetic properties (e.g., slower release of Compound 7) to those of liposomes in which there was no acid wash purification step. As shown in FIG. 4, liposomes in which there was no acid wash purification step resulted in a burst release of drug as seen by greater than 50% drug loss at the first time period. In contrast, those liposomes that had been pre-washed with acid exhibited the desired extended drug release over time.

Example 9. Impact of Different Acids in the Preparation of Liposome Formulations Formulations of liposomes containing Compound 9 were prepared as described in Examples 1A, 1B, and 2 in Steps A-C. All liposome formulations comprised DSPC/Cholesterol/PEGylated (58/40/2 mol %) and used 250 mM AS as the loading aid. In the present Example, the purification of drug-loaded liposomes was performed according to the parameters described herein.

Purification of the formulations were carried using tangential flow filtration (Slice 200, Sartorius) equipped with 100-300 k MWCO (Hydrosart, Sartorius) PES membranes. The formulation was first concentrated to 5 mL, than purified with 12 volume exchanges of acidified sugar (dextrose or sucrose) solution. The acid in the acidified sugar solution was methanesulfonic acid. The concentration of methanesulfonic acid in the acidified sugar solution was 1 mM or 5 mM. The acidified sugar solution alternatively contained sodium acetate at a pH of about 4.0. The concentration of sodium acetate in the acidified sugar solution was about 25 mM. Thereafter, the formulation was purified with another 12 volume exchanges of 9% dextrose.

Certain purification parameters (e.g., compositions of acidified sugar solutions) and characterization of liposome samples prepared according to this Example are presented below in Table 5.

TABLE 5

| Purification parameters and characterization of liposomes. | | | |
|---|---|---|---|
| | Sample 1 | Sample 2 | Sample 3 |
| Buffer | 9% sucrose 5 mM $MeSO_3H$ | 9% sucrose 1 mM $MeSO_3H$ | 9% sucrose 25 mM NaAc |
| pH | 2.3 | 3 | 4 |
| EE (%) | 90.3 | 86.2 | 89.2 |
| D/L ratio | 0.047 | 0.043 | 0.048 |
| Lyso-PC (%) | 4 | 5.7 | 2.6 |

Buffer = composition of acidified sugar solution.
pH = pH of acidified sugar solution.
EE = encapsulation efficiency.
D/L ratio = drug/phospholipid ratio.
Lyso-PC (%) = percent of lysolipid (DSPC degradation product) detected.

Example 10. Impact of Different Buffers in the Preparation of Liposome Formulations Formulations of liposomes containing Compound 9 were prepared as described in Examples 1A, 1B, and 2 in Steps A-C. All liposome formulations comprised DSPC/Cholesterol/PEGylated (58/40/2 mol %) and used 250 mM AS as the loading aid. In the present Example, the purification of drug-loaded liposomes was performed according to the parameters described herein.

Purification of the formulations were carried using tangential flow filtration (Slice 200, Sartorius) equipped with 100-300 k MWCO (Hydrosart, Sartorius) PES membranes. The formulation was first concentrated to 10 mL, than purified with 12 volume exchanges of acidified sugar (dextrose or sucrose) solution. The acid in the acidified sugar solution was 10 mM methanesulfonic acid. Thereafter, the formulation was purified with another 8 volume exchanges of 5% dextrose. Finally, the formulation was concentrated to 5 mL, collected and filtered through a 0.22 μm PES syringe filter.

Certain purification parameters (e.g., compositions of acidified sugar solutions) and characterization of liposome samples prepared according to this Example are presented below in Table 6.

TABLE 6

| Purification parameters and characterization of liposomes. | | | |
|---|---|---|---|
| | Sample 1 | Sample 2 | Sample 3 |
| Buffer | 9% dextrose 10 mM $MeSO_3H$ | 5% dextrose 10 mM $MeSO_3H$ | 9% sucrose 10 mM $MeSO_3H$ |
| EE (%) | 89 | 90 | 90 |
| D/L ratio | 0.05 | 0.06 | 0.05 |
| Lyso-PC (%) | 3.4 | 3.4 | 2.7 |

Buffer = composition of acidified sugar solution.
EE = encapsulation efficiency.
D/L ratio = drug/phospholipid ratio.
Lyso-PC (%) = percent of lysolipid (DSPC degradation product) detected.

The invention claimed is:

1. A method of purifying a crude liposome composition, the liposome comprising:

(a) a lipid bilayer;

(b) an internal medium; and (c) a first fraction of a therapeutic agent encapsulated in the internal medium of the liposome, wherein the therapeutic agent has low water solubility and is protonatable to a protonated form, and wherein a second fraction of the therapeutic agent is entrained in the lipid bilayer;

wherein the method comprises:

washing the crude liposome composition with an acidified aqueous solution having a pH from 1 to 6.

2. The method of claim 1, wherein:

the lipid bilayer comprises a first lipid and a first sterol; and the internal medium comprises a first loading aid.

3. The method of claim 2, wherein the first lipid is a polymer-conjugated lipid selected from 1,2-distearoyl-rac-glycero-3-methoxypoly(ethylene glycol), 1,2-dimyristoyl rac-glycero-3-methoxypoly(ethylene glycol), 1,2-dipalmitoyl-rac-glycero-3-methoxypoly(ethylene glycol), and 1,2-distearoyl-sn-glycero-3-phosphoethanolamine-poly(ethylene glycol).

4. The method of claim 2, wherein the first lipid is DSG-PEG2000.

5. The method of claim 2, wherein the lipid bilayer further comprises a second lipid, wherein the second lipid is a phospholipid selected from distearoyl phosphatidyl choline (DSPC) and hydrogenated sphingomyelin.

6. The method of claim 1, wherein the internal medium is an acidic aqueous internal medium.

7. The method of claim 1, wherein the internal medium further comprises an additional solvent, wherein the additional solvent is an organic solvent.

8. The method of claim 7, wherein the additional solvent is dimethylsulfoxide (DMSO).

9. The method of claim 2, wherein the first loading aid is an ionic loading aid selected from ammonium sulfate (AS), ammonium sucrose octasulfate (NH4SOS), potassium sucrose octasulfate (KSOS), triethanolammonium sucrose octasulfate (TEA (OH) SOS), triethylammonium sucrose octasulfate (TEASOS), and sodium citrate.

10. The method of claim 2, wherein the internal medium further comprises a second loading aid, wherein the second loading aid is an ionic loading aid selected from ammonium sulfate (AS), ammonium sucrose octasulfate (NH4SOS), potassium sucrose octasulfate (KSOS), triethylammonium sucrose octasulfate (TEASOS), and sodium citrate.

11. The method of claim 2, wherein the first sterol is cholesterol or beta-sitosterol.

12. The method of claim 1, wherein the therapeutic agent has a cLogP of greater than about 2 and the protonated form has a pKa of greater than about 2.

13. The method of claim 12, wherein the therapeutic agent is selected from an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, and a proteasome inhibitor.

14. The method of claim 13, wherein the therapeutic agent is a Bcl inhibitor selected from a Bcl-2 inhibitor, a Bcl-$X_L$ inhibitor, and a Bc1-2/Bcl-$X_L$ dual inhibitor.

15. The method of claim 1, wherein the liposomes further comprise an additional therapeutic agent which is encapsulated in the liposome, wherein the additional therapeutic agent is selected from an anti-angiogenic agent, an antimetabolite, an apoptosis inducing agent, a cell cycle inhibitor, a cell cycle control inhibitor, a checkpoint inhibitor, a cyclin-dependent kinase inhibitor, a cytotoxic agent, a DNA damaging agent, a DNA repair inhibitor, a mitochondrial poison, a telomerase inhibitor, a signal transduction inhibitor, a transcription inhibitor, a Bcl inhibitor, a PARP inhibitor, a PI3K inhibitor, an HSP90 inhibitor, a JAK inhibitor, an ATR inhibitor, an HDAC inhibitor, a tyrosine kinase inhibitor, a receptor tyrosine kinase inhibitor, a BTK inhibitor, an alkylating agent, an SMO inhibitor, an antitubulin agent, an MEK inhibitor, a topoisomerase inhibitor, a RAF inhibitor, a BRAF inhibitor, and a proteasome inhibitor.

16. The method of claim 1, wherein the acidified aqueous solution comprises a sugar.

17. The method of claim 16, wherein the acidified aqueous solution comprises dextrose and/or sucrose.

18. The method of claim 1, wherein the acidified aqueous solution comprises acid in a concentration of from about 1 mM to about 100 mM.

19. The method of claim 1, wherein the acidified aqueous solution comprises methanesulfonic acid.

20. The method of claim 1, wherein the method results in protonating the second fraction of the therapeutic agent and releasing it from the lipid bilayer.

21. The method of claim 20, wherein the method further comprises separating the released protonated therapeutic agent from the liposome, thereby purifying the crude liposome composition.

22. The method of claim 13, wherein the Bcl inhibitor is:

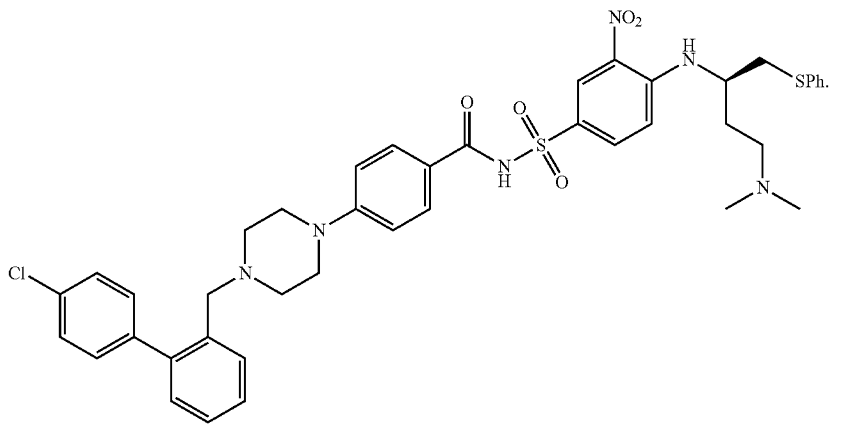

* * * * *